(12) United States Patent
Aebi et al.

(10) Patent No.: US 9,790,217 B2
(45) Date of Patent: Oct. 17, 2017

(54) PYRIDINYLOXY- AND PHENYLOXY-PYRAZOLYL COMPOUNDS

(71) Applicant: Hoffmann-La Roche Inc., Little Falls, NJ (US)

(72) Inventors: Johannes Aebi, Binningen (CH); Kurt Amrein, Itingen (CH); Benoit Hornsperger, Altkirch (FR); Bernd Kuhn, Reinach BL (CH); Dongbo Li, Shanghai (CN); Yongfu Liu, Shanghai (CN); Hans P. Maerki, Basel (CH); Rainer E. Martin, Basel (CH); Alexander V. Mayweg, Basel (CH); Xuefei Tan, Shanghai (CN); Lisha Wang, Basel (CH); Jun Wu, Shanghai (CN)

(73) Assignee: Hoffmann-La Roche Inc., Littel Falls, NJ (US)

( * ) Notice: Subject to any disclaimer, the term of this patent is extended or adjusted under 35 U.S.C. 154(b) by 0 days.

(21) Appl. No.: 15/498,977

(22) Filed: Apr. 27, 2017

(65) Prior Publication Data

US 2017/0226097 A1     Aug. 10, 2017

Related U.S. Application Data

(63) Continuation of application No. PCT/EP2015/074925, filed on Oct. 28, 2015.

(30) Foreign Application Priority Data

Oct. 31, 2014  (WO) ............... PCT/CN2014/090070

(51) Int. Cl.

| C07D 401/10 | (2006.01) |
|---|---|
| C07D 417/04 | (2006.01) |
| C07D 231/18 | (2006.01) |
| C07D 401/12 | (2006.01) |
| C07D 401/04 | (2006.01) |
| C07D 403/10 | (2006.01) |
| C07D 413/12 | (2006.01) |
| C07D 403/12 | (2006.01) |
| C07D 401/14 | (2006.01) |
| C07D 403/04 | (2006.01) |

(52) U.S. Cl.
CPC ......... *C07D 417/04* (2013.01); *C07D 231/18* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/12* (2013.01); *C07D 413/12* (2013.01)

(58) Field of Classification Search
CPC ... C07D 417/04; C07D 231/18; C07D 401/04
See application file for complete search history.

(56) References Cited

U.S. PATENT DOCUMENTS 7,435,728 B2 * 10/2008 Jones .................. C07D 231/12
                                                            514/211.05

* cited by examiner

*Primary Examiner* — Shawquia Jackson

(57) ABSTRACT

The invention provides novel compounds having the general formula (I)

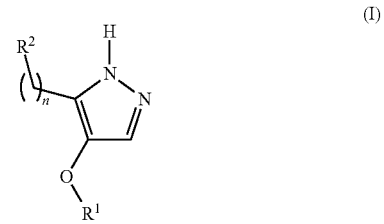

wherein $R^1$, $R^2$ and n are as described herein, compositions including the compounds and methods of using the compounds.

20 Claims, No Drawings

PYRIDINYLOXY- AND PHENYLOXY-PYRAZOLYL COMPOUNDS

CROSS REFERENCE TO RELATED APPLICATIONS

This application is a continuation of International Application No. PCT/EP2015/074925 having an international filing date of Oct. 28, 2015 and which claims benefit under 35 U.S.C. §119 to International Application PCT/CN2014/090070 filed Oct. 31, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Inhibitors of aldosterone synthase can potentially protect organs and/or tissues from damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

BRIEF SUMMARY OF THE INVENTION

The present invention provides novel compounds of formula (I)

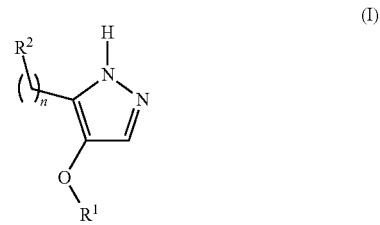

wherein $R^1$ is substituted phenyl or substituted pyridinyl, wherein substituted phenyl and substituted pyridinyl are substituted with one to three substituents independently selected from cyano, halogen, haloalkyl, alkoxy and alkyl;

$R^2$ is a ring system selected from group A, B, C, D, E, F, G and H.

$R^3$ and $R^7$ are independently selected from H, alkyl, alkoxy, halogen, haloalkoxy, carboxy, alkoxycarbonyl, substituted phenylalkoxy, substituted heteroarylalkoxy, substituted heteroarylalkyl, substituted heteroaryloxyalkyl and substituted heterocycloalkoxy, wherein substituted phenylalkoxy, substituted heteroarylalkoxy, substituted heteroarylalkyl, substituted heteroaryloxyalkyl and substituted heterocycloalkoxy are substituted with one to three substituents independently selected from H, alkyl or halogen;

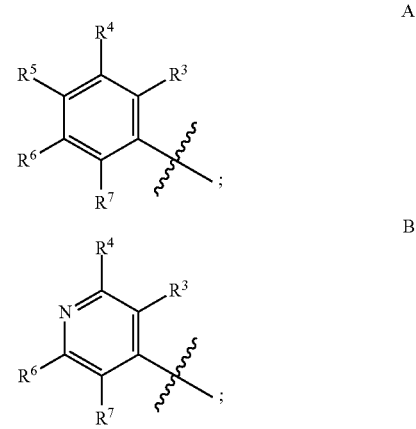

-continued

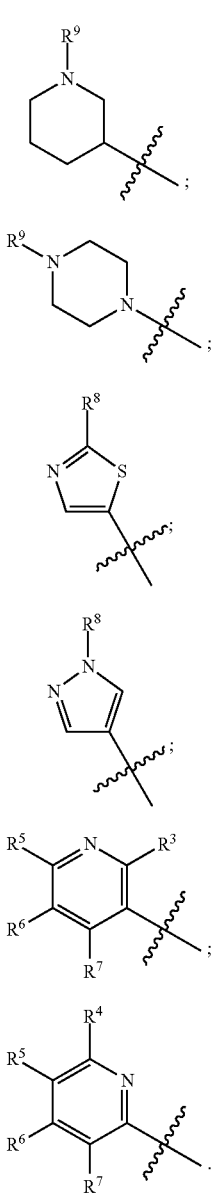

R⁴ is H, hydroxy, hydroxyalkyl, alkoxy, alkoxycarbonyl, halogen, phenylalkoxy, heterocycloalkylcarbonyl substituted by one to three substituents independently selected from H, alkylcarbonyl alkylsulfonyl and hydroxyalkyl, heteroarylalkoxy substituted by one to three substituents independently selected from H, alkyl and halogen, heteroaryloxyalkyl substituted by one to three substituents independently selected from H and halogen, heteroarylalkyl substituted by one to three substituents independently selected from H and hydroxy, heterocycloalkoxy substituted by one to three substituents independently selected from H and alkylcarbonyl, or heterocycloalkylalkyl substituted by one to three substituents independently selected from H, halogen and hydroxyalkyl;

R⁶ is H or halogen;

R⁵ is H, halogen, alkoxy, alkylsulfonyl, alkylsulfanyl or haloalkyl;

R⁸ is alkyl or phenylalkyl;

R⁹ is H, alkylcarbonyl or heteroarylcarbonyl substituted by one to three substituents independently selected from H and alkyl;

n is zero, 1 or 2;

and pharmaceutically acceptable salts thereof.

In another embodiment, the present inventions provide for pharmaceutical compositions comprising compounds of Formula I.

In another embodiment, the present invention provides aldosterone synthase inhibitors for therapy in a mammal useful for the treatment or prophylaxis of chronic kidney disease, congestive heart failure, hypertension, primary aldosteronism and Cushing syndrome.

DETAILED DESCRIPTION OF THE INVENTION

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

The compounds of the present invention according formula (I) are potent inhibitors of CYPB11B2 and present an improved selectivity towards CYP11B2 versus CYP11B1 combined with an improved metabolic stability.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

The term "alkoxy" denotes a group of the formula R'—O—, wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is methoxy or ethoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl and isopropyl, n-butyl, iso-butyl, sec-butyl and ter-butyl. Particular alkyl group is methyl.

The term "alkylcarbonyl" of the formula —C(O)—R', wherein R' is an alkyl group. Examples of alkylcarbonyl groups include groups of the formula —C(O)—R', wherein R' is methyl or ethyl. Particular alkylcarbonyl group is a group of the formula —C(O)—R', wherein R' is methyl.

The term "alkylsulfanyl" denotes a group of the formula R'—S—, wherein R' is an alkyl group. Examples of alkylsulfanyl are groups wherein R' is methyl, ethyl, propyl and isopropyl, n-butyl, iso-butyl, sec-butyl and ter-butyl. Particular alkylsulfanyl is group wherein R' is methyl.

The term "alkylsulfonyl" denotes a group of the formula R'—S(O)$_2$—, wherein R' is an alkyl group. Examples of alkylsulfonyl are groups wherein R' is methyl, ethyl, propyl and isopropyl, n-butyl, iso-butyl, sec-butyl and ter-butyl. Particular alkylsulfonyl is group wherein R' is methyl.

The term "carbonyl" denotes a —C(O)— group.

The term "cyano" denotes a —C≡N group.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are difluoromethoxy and trifluoromethoxy. Further particular haloalkoxy group is difluoromethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The terms "halogen" and "halo" are used interchangeably herein and denote fluoro, chloro, bromo, or iodo. Particular halogens are chloro and fluoro. Further particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl are triazolyl, pyrazolyl, imidazolyl, pyridinyl and pyrazolyl.

The term "heteroarylalkoxy" denotes an alkoxy group wherein one of the hydrogen atoms of the alkoxy group has been replaced a heteroaryl group. Particular heteroarylalkoxy group is heteroarylmethoxy wherein the heteroaryl group is pyrazolyl, triazolyl or pyridinyl.

The term "heteroarylalkyl" denotes an alkyl group wherein one of the hydrogen atoms of the alkyl group has been replaced an aryl group. Particular heteroarylalkyl group is heteroarylmethyl, wherein the heteroaryl group is pyridinonyl.

The term "heteroarylcarbonyl" of the formula —C(O)—R', wherein R' is a heteroaryl group. Particular heteroarylcarbonyl group is a group of the formula —C(O)—R', wherein R' is pyrazolyl or pyridinyl.

The term "heteroaryloxyalkyl" denotes a group of the formula R'—O-alkyl, wherein R' is a heteroaryl group. Particular heteroaryloxyalkyl is a group of formula R'—O-methyl, wherein R' is pyridinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl and thiazinanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, 3-thia-9-aza-bicyclo[3.3.1]nonyl and 2,6-diaza-spiro[3.3]heptanyl. Examples for partly unsaturated heterocycloalkyl are dihydrofuryl, imidazolinyl, dihydro-oxazolyl, tetrahydro-pyridinyl, or dihydropyranyl. More particular examples of heterocycloalkyl group are pyrrolidinyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, thiazinanyl and 2,6-diaza-spiro[3.3]heptanyl.

The term "heterocycloalkylalkyl" denotes an alkyl group wherein one of the hydrogen atoms of the alkyl group has been replaced a heterocycloalkyl group. Particular heterocycloalkylalkyl group is heteroarylmethyl, wherein the heterocycloalkyl group is azetidinyl or morpholinyl.

The term "heterocycloalkylcarbonyl" of the formula —C(O)—R', wherein R' is a heterocycloalkyl group. Particular heterocycloalkycarbonyl group is a group of the formula —C(O)—R', wherein R' is azetidinyl, morpholinyl or piperazinyl.

The term "heterocycloalkoxy" denotes a group of the formula R'—O—, wherein R' is a heterocycloalkyl group. Particular heterocycloalkoxy is a group of formula R'—O—, wherein R' is pyrrolidinyl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular example is hydroxymethyl.

The term "phenylalkoxy" denotes an alkoxy group wherein one of the hydrogen atoms of the alkoxy group has been replaced by a phenyl. Examples of phenylalkoxy are phenylmethoxy and phenylethoxy. Particular example of phenylalkoxy is phenylmethoxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. µAdditionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol µM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$ ("T"), $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^{2}H$ atom are also an embodiment of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Also a particular embodiment of the present invention are compounds according to formula (I) as described herein wherein $R^1$ is phenyl substituted with substituted with one to three substituents independently selected from cyano and halogen.

Another particular embodiment of the present invention are compounds according to formula (I) as described herein wherein $R^2$ is a ring system selected from group A, B, C, D, E and F.

A further particular embodiment of the present invention are compounds according to formula (I) as described herein, wherein $R^2$ is a ring system selected from group A, B and C.

A more particular embodiment of the present invention are compounds according to formula (I) as described herein, wherein $R^2$ is the ring system group A.

A still more particular embodiment of the present invention are compounds according to formula (I) as described herein, wherein $R^1$ is optionally substituted phenyl and $R^2$ is the ring system group A.

A still more particular embodiment of the present invention are compounds according to formula (I) as described herein, wherein $R^1$ is optionally substituted pyridinyl and $R^2$ is the ring system group A.

A still more particular embodiment of the present invention are compounds according to formula (I) as described herein, wherein $R^1$ is optionally substituted phenyl and $R^2$ is the optionally substituted ring system group A optionally substituted with (a) phenylalkoxy, (b) heteroarylalkoxy optionally substituted by one to three substituents independently selected from alkyl and halogen, (c) heteroaryloxyalkyl optionally substituted by one to three halogen(s), (d) heteroarylalkyl optionally substituted by one to three substituents hydroxy and (e) heterocycloalkoxy optionally substituted by one to three alkylcarbonyl A still more particular embodiment of the present invention are compounds according to formula (I) as described herein, wherein $R^1$ is optionally substituted phenyl and $R^2$ is the optionally substituted ring system group A optionally substituted with alkyl, alkoxy, halogen, haloalkoxy, carboxy, alkoxycarbonyl.

A still more particular embodiment of the present invention are compounds according to formula (I) as described herein, wherein $R^1$ is optionally substituted phenyl and $R^2$ is the optionally substituted ring system group A optionally substituted with heterocycloalkylalkyl optionally substituted by one to three substituents independently selected from halogen, alkyl and hydroxyalkyl A more particular embodiment of the present invention are compounds according to formula (I) as described herein, wherein $R^2$ is the ring system group B.

A more particular embodiment of the present invention are compounds according to formula (I) as described herein, wherein $R^2$ is the ring system group C.

A more particular embodiment of the present invention are compounds according to formula (I) as described herein, wherein $R^2$ is the ring system group D.

A more particular embodiment of the present invention are compounds according to formula (I) as described herein, wherein $R^2$ is the ring system group E.

A more particular embodiment of the present invention are compounds according to formula (I) as described herein, wherein $R^2$ is the ring system group F.

A more particular embodiment of the present invention are compounds according to formula (I) as described herein, wherein $R^2$ is the ring system group G.

A more particular embodiment of the present invention are compounds according to formula (I) as described herein, wherein $R^2$ is the ring system group H.

Also an embodiment of the present invention are compounds according to formula (I) as described herein, wherein n is zero.

Also an embodiment of the present invention are compounds according to formula (I) as described herein, wherein $R^7$ is H.

Another particular embodiment of the present invention are compounds according to formula (I) as described herein, wherein $R^3$ is H, alkoxy, halogen, haloalkoxy or heteroarylalkoxy substituted with one to three substituents independently selected from H and alkyl.

Also a particular embodiment of the present invention are compounds according to formula (I) as described herein, wherein $R^4$ is H, hydroxy, heteroarylalkoxy or heterocycloalkylalkyl.

A further particular embodiment of the present invention are compounds according to formula (I) as described herein, wherein $R^4$ is H.

Another embodiment of the present invention are compounds according to formula (I) as described herein, wherein $R^5$ is H.

Another particular embodiment of the present invention are compounds according to formula (I) as described herein, wherein $R^6$ is H.

Another particular embodiment of the present invention are compounds according to formula (I) as described herein, wherein $R^7$ is H.

Another embodiment of the present invention are compounds according to formula (I) as described herein, wherein $R^9$ is heteroarylcarbonyl substituted by one alkyl.

Particular examples of compounds of formula (I) as described herein are selected from 4-(4-Chlorophenoxy)-5-(2,3-difluorophenyl)-1H-pyrazole;
3-(4-Chlorophenyl)-4-(4-methoxyphenoxy)-1H-pyrazole;
4-(4-Chlorophenoxy)-3-(4-chlorophenyl)-1H-pyrazole;
4-(4-Chlorophenoxy)-3-(2-methoxyphenyl)-1H-pyrazole;
4-(4-Chlorophenoxy)-3-(2,4-dimethoxyphenyl)-1H-pyrazole;
4-(4-Chlorophenoxy)-5-(2-chlorophenyl)-1H-pyrazole;
4-(4-Chlorophenoxy)-5-[2-(trifluoromethoxy)phenyl]-1H-pyrazole;
4-(4-Chlorophenoxy)-5-[2-(difluoromethoxy)phenyl]-1H-pyrazole;
4-(4-Chlorophenoxy)-5-(2-fluorophenyl)-1H-pyrazole;
3-(5-Chloro-2-methoxyphenyl)-4-(4-chlorophenoxy)-1H-pyrazole;
5-(4-Chloro-2-fluorophenyl)-4-(4-chlorophenoxy)-1H-pyrazole;
4-(4-Chlorophenoxy)-5-(4-methyl sulfonylphenyl)-1H-pyrazole;
4-(4-Chlorophenoxy)-5-[2-fluoro-4-(trifluoromethyl)phenyl]-1H-pyrazole;
4-(4-Chlorophenoxy)-5-[4-(trifluoromethyl)phenyl]-1H-pyrazole;
4-(4-Chlorophenoxy)-5-(2,4-difluorophenyl)-1H-pyrazole;
5-(4-Methylsulfonylphenyl)-4-[4-(trifluoromethyl)phenoxy]-1H-pyrazole;
5-(2-Chloro-4-methyl sulfanylphenyl)-4-(4-chlorophenoxy)-1H-pyrazole;
4-[[5-(4-Methyl sulfonylphenyl)-1H-pyrazol-4-yl]oxy]benzonitrile;
2-Chloro-5-[[5-(2-chlorophenyl)-1H-pyrazol-4-yl]oxy]pyridine;
5-[[5-(2-Chlorophenyl)-1H-pyrazol-4-yl]oxy]-2-methylpyridine;
2-[[5-(2,4-Dichlorophenyl)-1H-pyrazol-4-yl]oxy]-6-fluoropyridine;
2-[[3-(2,4-Dichlorophenyl)-1H-pyrazol-4-yl]oxy]-6-methylpyridine;

5-(2-Chlorophenyl)-4-[4-(trifluoromethyl)phenoxy]-1H-pyrazole;
4-(4-Chloro-2-fluorophenoxy)-5-(2-chlorophenyl)-1H-pyrazole;
4-[[5-(2-Chlorophenyl)-1H-pyrazol-4-yl]oxy]benzonitrile;
4-[[5-(2-Chloro-4-methyl sulfanylphenyl)-1H-pyrazol-4-yl]oxy]benzonitrile;
5-(4-Chloro-2-fluorophenyl)-4-[4-(trifluoromethyl)phenoxy]-1H-pyrazole;
4-[[5-(2-Chlorophenyl)-1H-pyrazol-4-yl]oxy]-3-fluorobenzonitrile;
4-[[5-(2,3-Difluorophenyl)-1H-pyrazol-4-yl]oxy]benzonitrile;
4-[[5-(3-Chloro-2-fluorophenyl)-1H-pyrazol-4-yl]oxy]benzonitrile;
5-(3-Chloro-2-fluorophenyl)-4-(4-chlorophenoxy)-1H-pyrazole;
4-[[5-(3-Chlorophenyl)-1H-pyrazol-4-yl]oxy]benzonitrile;
Methyl 3-[4-(4-cyanophenoxy)-1H-pyrazol-3-yl]benzoate;
5-(2-Chloro-3-fluorophenyl)-4-(4-chlorophenoxy)-1H-pyrazole;
4-[[5-(2-Chloro-3-fluorophenyl)-1H-pyrazol-4-yl]oxy]benzonitrile;
4-[[5-(3-Phenylmethoxyphenyl)-1H-pyrazol-4-yl]oxy]benzonitrile;
4-[[5-(2-Chloropyridin-4-yl)-1H-pyrazol-4-yl]oxy]benzonitrile;
Methyl 3-[4-(4-cyano-2-fluorophenoxy)-1H-pyrazol-3-yl]benzoate;
Ethyl 2-[4-(4-cyanophenoxy)-1H-pyrazol-3-yl]benzoate;
2-[4-(4-Cyanophenoxy)-1H-pyrazol-3-yl]benzoic acid;
4-[[5-(2-Phenylmethoxyphenyl)-1H-pyrazol-4-yl]oxy]benzonitrile;
5-(2-Chloro-4-methylsulfonylphenyl)-4-(4-chlorophenoxy)-1H-pyrazole;
4-[[5-(2-Chloro-4-methylsulfonylphenyl)-1H-pyrazol-4-yl]oxy]benzonitrile;
4-[[3-[3-(4-Acetylpiperazine-1-carbonyl)phenyl]-1H-pyrazol-4-yl]oxy]benzonitrile;
4-[[3-[3-(Morpholine-4-carbonyl)phenyl]-1H-pyrazol-4-yl]oxy]benzonitrile;
4-[[3-[3-(4-Methylsulfonylpiperazine-1-carbonyl)phenyl]-1H-pyrazol-4-yl]oxy]benzonitrile;
4-[[3-[3-[3-(Hydroxymethyl)azetidine-1-carbonyl]phenyl]-1H-pyrazol-4-yl]oxy]benzonitrile;
4-[[3-(3-Hydroxyphenyl)-1H-pyrazol-4-yl]oxy]benzonitrile;
4-[[3-[3-(Hydroxymethyl)phenyl]-1H-pyrazol-4-yl]oxy]benzonitrile;
4-[[3-[3-(Pyridin-2-ylmethoxy)phenyl]-1H-pyrazol-4-yl]oxy]benzonitrile;
4-[[3-[3-(Pyridin-3-ylmethoxy)phenyl]-1H-pyrazol-4-yl]oxy]benzonitrile;
4-[[3-[3-[(3-Methyl-1,2-oxazol-5-yl)methoxy]phenyl]-1H-pyrazol-4-yl]oxy]benzonitrile;
4-[[3-[3-[(3-Methyltriazol-4-yl)methoxy]phenyl]-1H-pyrazol-4-yl]oxy]benzonitrile;
4-[[3-[3-(Pyridin-4-ylmethoxy)phenyl]-1H-pyrazol-4-yl]oxy]benzonitrile;
4-[[3-[3-[(2-Chloropyridin-4-yl)methoxy]phenyl]-1H-pyrazol-4-yl]oxy]benzonitrile;
4-[[3-[3-[(1-Methylpyrazol-4-yl)methoxy]phenyl]-1H-pyrazol-4-yl]oxy]benzonitrile;
(rac)-4-[[3-(3-Pyrrolidin-3-yloxyphenyl)-1H-pyrazol-4-yl]oxy]benzonitrile;
(rac)-4-[[3-[3-(1-Acetylpyrrolidin-3-yl)oxyphenyl]-1H-pyrazol-4-yl]oxy]benzonitrile;
4-[[3-(3-Butoxyphenyl)-1H-pyrazol-4-yl]oxy]benzonitrile;
4-[[3-[2-(2-Methoxyphenyl)ethyl]-1H-pyrazol-4-yl]oxy]benzonitrile;
(rac)-4-[[5-(3-Piperidyl)-1H-pyrazol-4-yl]oxy]benzonitrile;
(rac)-4-[[3-(1-Acetylpiperidin-3-yl)-1H-pyrazol-4-yl]oxy]benzonitrile;
(rac)-4-[[3-[1-(1-Methylpyrazole-4-carbonyl)piperidin-3-yl]-1H-pyrazol-4-yl]oxy]benzonitrile;
(rac)-4-[[3-[1-(Pyridine-3-carbonyl)piperidin-3-yl]-1H-pyrazol-4-yl]oxy]benzonitrile;
(rac)-4-[[3-[1-(Pyridine-2-carbonyl)piperidin-3-yl]-1H-pyrazol-4-yl]oxy]benzonitrile;
4-[[3-(2-Methyl-1,3-thiazol-5-yl)-1H-pyrazol-4-yl]oxy]benzonitrile;
4-[[3-(1-Methylpyrazol-4-yl)-1H-pyrazol-4-yl]oxy]benzonitrile;
4-[[3-(1-Benzylpyrazol-4-yl)-1H-pyrazol-4-yl]oxy]benzonitrile;
4-[[3-[3-[(6-Fluoropyridin-2-yl)oxymethyl]phenyl]-1H-pyrazol-4-yl]oxy]benzonitrile;
4-[[3-[3-(Pyridin-3-yloxymethyl)phenyl]-1H-pyrazol-4-yl]oxy]benzonitrile;
1-[[3-[4-(4-Cyanophenoxy)-1H-pyrazol-3-yl]phenyl]methyl]pyridin-1-ium-3-olate;
4-[[3-[3-[(4-Oxopyridin-1-yl)methyl]phenyl]-1H-pyrazol-4-yl]oxy]benzonitrile;
4-[[3-[3-[(6-Chloropyridin-2-yl)oxymethyl]phenyl]-1H-pyrazol-4-yl]oxy]benzonitrile;
4-[[3-[3-[[3-Fluoro-3-(hydroxymethyl)azetidin-1-yl]methyl]phenyl]-1H-pyrazol-4-yl]oxy]benzonitrile;
4-[[3-[3-(Morpholin-4-ylmethyl)phenyl]-1H-pyrazol-4-yl]oxy]benzonitrile;
4-[[3-[2-(Pyridin-4-ylmethoxy)phenyl]-1H-pyrazol-4-yl]oxy]benzonitrile;
4-[[3-[2-(Pyridin-3-ylmethoxy)phenyl]-1H-pyrazol-4-yl]oxy]benzonitrile;
4-[[3-(2-Hydroxyphenyl)-1H-pyrazol-4-yl]oxy]benzonitrile;
4-[[3-[2-(Pyridin-2-ylmethoxy)phenyl]-1H-pyrazol-4-yl]oxy]benzonitrile;
4-[[3-[2-[(1-Methylpyrazol-4-yl)methoxy]phenyl]-1H-pyrazol-4-yl]oxy]benzonitrile;
4-[[3-[2-[(3-Methyltriazol-4-yl)methoxy]phenyl]-1H-pyrazol-4-yl]oxy]benzonitrile;
4-[[3-[2-(Pyridin-3-yloxymethyl)phenyl]-1H-pyrazol-4-yl]oxy]benzonitrile;
4-[[3-[2-[(4-Oxopyridin-1-yl)methyl]phenyl]-1H-pyrazol-4-yl]oxy]benzonitrile;
4-[[3-(2-Fluoro-3-hydroxyphenyl)-1H-pyrazol-4-yl]oxy]benzonitrile;
4-[[3-[2-Fluoro-3-(pyridin-4-ylmethoxy)phenyl]-1H-pyrazol-4-yl]oxy]benzonitrile;
4-[[3-[3-[(2-Chloropyridin-4-yl)methoxy]-2-fluorophenyl]-1H-pyrazol-4-yl]oxy]benzonitrile;
4-[[5-(Piperazin-1-ylmethyl)-1H-pyrazol-4-yl]oxy]benzonitrile;
4-[[5-[[4-(1-Methylpyrazole-4-carbonyl)piperazin-1-yl]methyl]-1H-pyrazol-4-yl]oxy]benzonitrile;
(rac)-3-Fluoro-4-[[5-[1-(1-methylpyrazole-4-carbonyl)piperidin-3-yl]-1H-pyrazol-4-yl]oxy]benzonitrile;
4-[[3-[3-Chloro-2-[(3-methyltriazol-4-yl)methoxy]phenyl]-1H-pyrazol-4-yl]oxy]benzonitrile;
(rac)-3-Fluoro-4-(3-(1-nicotinoylpiperidin-3-yl)-1H-pyrazol-4-yloxy)benzonitrile;
and pharmaceutically acceptable salts thereof.

More particular examples of compounds of formula (I) as described herein are selected from
4-(4-Chlorophenoxy)-3-(2-methoxyphenyl)-1H-pyrazole;
4-(4-Chlorophenoxy)-5-[2-(difluoromethoxy)phenyl]-1H-pyrazole;
4-[[5-(2-Chlorophenyl)-1H-pyrazol-4-yl]oxy]benzonitrile;
4-[[5-(2-Chlorophenyl)-1H-pyrazol-4-yl]oxy]-3-fluorobenzonitrile;
4-[[3-[2-(2-Methoxyphenyl)ethyl]-1H-pyrazol-4-yl]oxy]benzonitrile;

(rac)-4-[[3-[1-(1-Methylpyrazole-4-carbonyl)piperidin-3-yl]-1H-pyrazol-4-yl]oxy]benzonitrile;
4-[[3-[3-(Morpholin-4-ylmethyl)phenyl]-1H-pyrazol-4-yl]oxy]benzonitrile;
4-[[3-[2-[(3-Methyltriazol-4-yl)methoxy]phenyl]-1H-pyrazol-4-yl]oxy]benzonitrile;
4-[[3-(2-Fluoro-3-hydroxyphenyl)-1H-pyrazol-4-yl]oxy]benzonitrile;
4-[[3-[2-Fluoro-3-(pyridin-4-ylmethoxy)phenyl]-1H-pyrazol-4-yl]oxy]benzonitrile;
4-[[5-[[4-(1-Methylpyrazole-4-carbonyl)piperazin-1-yl]methyl]-1H-pyrazol-4-yl]oxy]benzonitrile;
(rac)-3-Fluoro-4-[[5-[1-(1-methylpyrazole-4-carbonyl)piperidin-3-yl]-1H-pyrazol-4-yl]oxy]benzonitrile;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the persons skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDI=1,1-carbonyldiimidazole, DCM=dichloromethane, DBU=2,3,4,6,7,8,9,10-octahydropyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=$iPr_2NEt$=N-ethyl diisopropylamine, IPC=in process control, LAH=lithium aluminium hydride, LDA=lithium diisopropylamide, $LiBH_4$=lithium borohydride, MeOH=methanol, $NaBH_3CN$, sodium cyanoborohydride, $NaBH_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Dimethylamino-alkene 1 or hydroxy-alkene compounds 2 (Scheme 1) react with hydrazine hydrate in the presence of an acid like e.g. aqueous hydrochloric acid in solvents like tetrahydrofuran, dioxane, methanol, ethanol or mixtures thereof at elevated temperatures e.g. between about 50° C. and the reflux temperature of the solvents to form pyrazole compounds 3 (step a).

Scheme 1

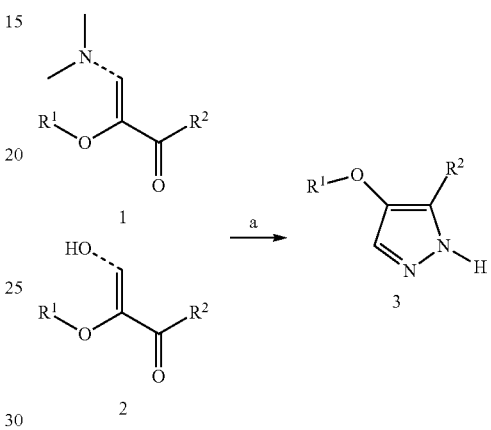

Protected pyrazole compounds 51 (Scheme 2) carrying a triflate, a bromo or iodo function react with boronic acid or ester compounds 52 or 56 using Suzuki conditions, e.g. in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130° C. leading to pyrazoles 54 or 57 (steps a).

Scheme 2

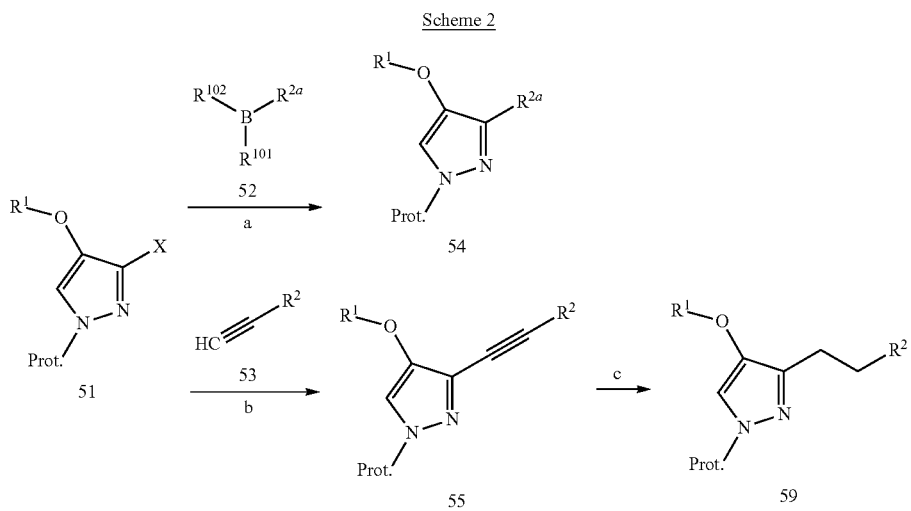

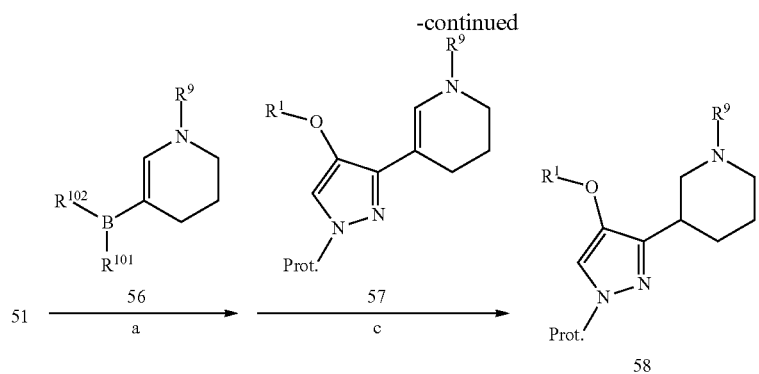

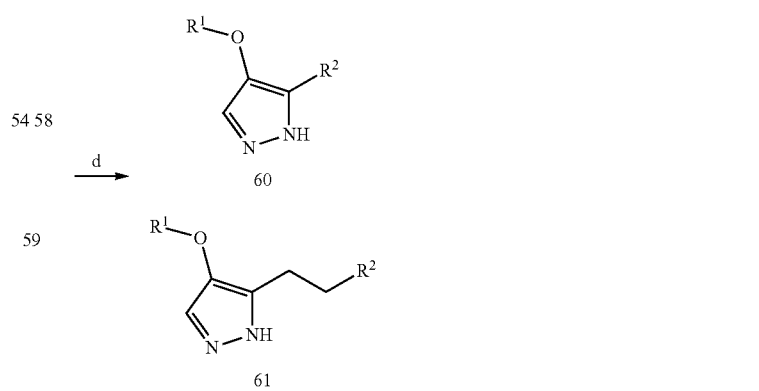

X is Halogen or OSO₂CF₃

R²ᵃ being aryl or heteroaryl

R¹⁰¹ and R¹⁰² are both OH or, e.g. together with the boron atom to which they are attached form 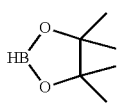

Alternatively, protected pyrazole compounds 51 (Scheme 2) carrying a triflate, a bromo or iodo function react with an alk-1-yne compound 53 under Sonagashira reaction conditions when treated with copper (I) iodide and tetrakis-(triphenylphosphine)-palladium(O) in piperidine between room temperature and about 100° C. giving alkyne pyrazole compounds 55 (step b). Catalytic hydrogenation transforms compounds 55 and 57 into pyrazoles 59 and 58 (step c). Subsequent removal of the protecting group in compounds 54, 58 and 59 gives free pyrazoles 60 and 61 (e.g. treatment with trifluoroacetic acid under microwave conditions at temperatures around 100° C. can be used for removal of a p-methoxy-benzyl protecting group, treatment with 4M HCl in dioxane in MeOH around room temperature can be used for removal of a THP protecting group, step d).

Scheme 3

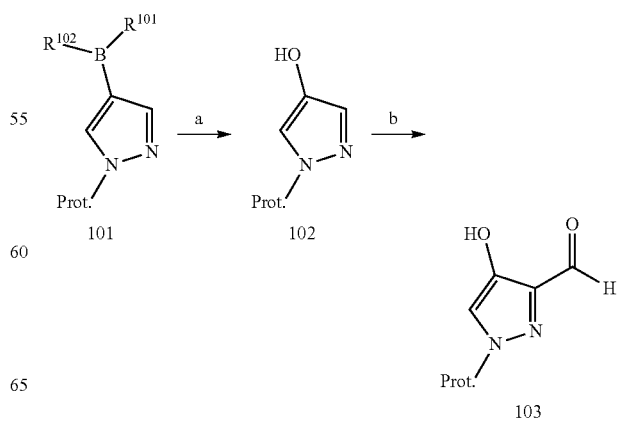

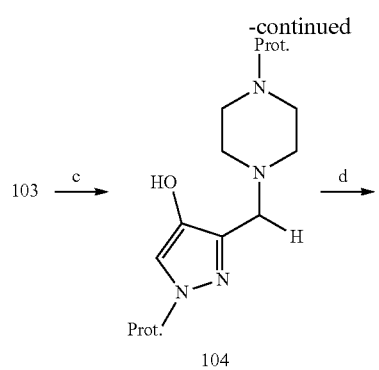

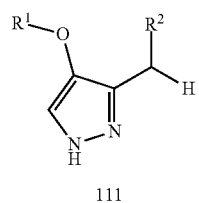

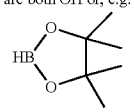

X is Halogen or OSO$_2$CF$_3$

R$^{101}$ and R$^{102}$ are both OH or, e.g. together with the boron atom to which they are attached form

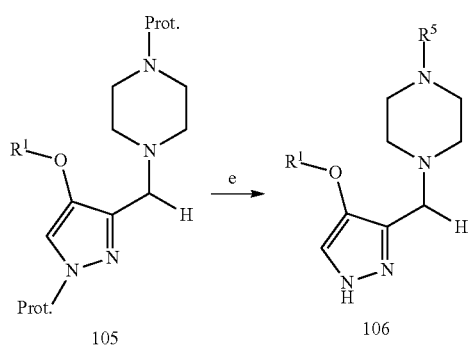

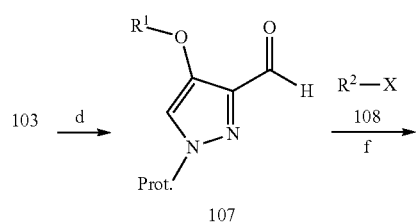

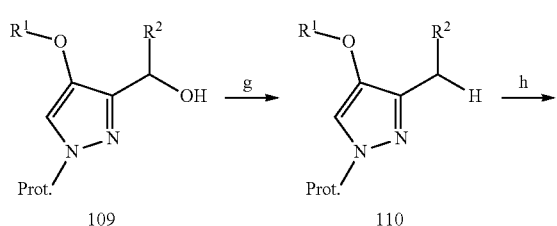

Hydroxy pyrazoles 102 can be prepared from pyrazole-boronic acid or ester compounds 101 carrying a suitable protecting group by oxidation with hydrogen peroxide in the presence of an acid like acetic acid in a solvent like THF preferably around 0° C. (step a, Scheme 3). Formylation of hydroxy pyrazoles 102 can be achieved e.g. by reaction with paraformaldehyde, manganese (II) chloride, TEA, in a solvent like acetonitrile at temperatures around 80° C. (step b). Reductive amination with suitable piperazine derivatives using e.g. sodium triacetoxyborohydride, acetic acid, in a solvent like dichloroethane around room temperature gives piperazinomethyl substituted hydroxy pyrazoles 104 (step c).

Reaction of piperazinomethyl substituted hydroxy pyrazoles 104 with suitable halo aryl compounds in the presence of potassium carbonate in a solvent like N-methyl pyrrolidone at elevated temperatures (up to 150° C.) and optionally with microwave irradiation give aryloxy-pyrazoles 105 (step d); alternatively aryloxy-pyrazoles 105 can be prepared from hydroxy pyrazoles 104 and halo aryl compounds in solvents like 1,4-dioxane, in the presence of copper (I) iodide, potassium or cesium carbonate, a chelating 1,2-diamino compound like N,N'-dimethylethylenediamine or trans-1,2-diamino-hexane, at elevated temperatures, preferable with the aid of microwave heating. Removal of the protecting function leads then to pyrazoles 106 (step e.).

Carbon linked halo-aromatic, halo-heteroaromatic or halo-heterocyclic compounds 108, preferably with X equal bromine or iodine can undergo halogen-metal exchange when treated with metals like magnesium or lithium in solvents like tetrahydrofuran in a temperature range between −78° C. and 0° C. and react subsequently with aldehydes 107 (prepared from hydroxy pyrazoles 103 as described for step d) preferably in a temperature range between −78° C. and room temperature to give hydroxy compounds 109 (Scheme 3, step f). Hydroxy groups in compounds 109 can be removed and replaced by hydrogen by treatment e.g. with a reagent like triethylsilane in a solvent like trifluoroacetic acid preferably between 0° C. and room temperature giving pyrazoles 110 (step g) and removal of the protecting group pyrazoles 111 (step h).

Dimethylamino-alkene 1 or hydroxy-alkene compounds 2 are known or can e.g. be prepared as described in Scheme 4:

Scheme 4

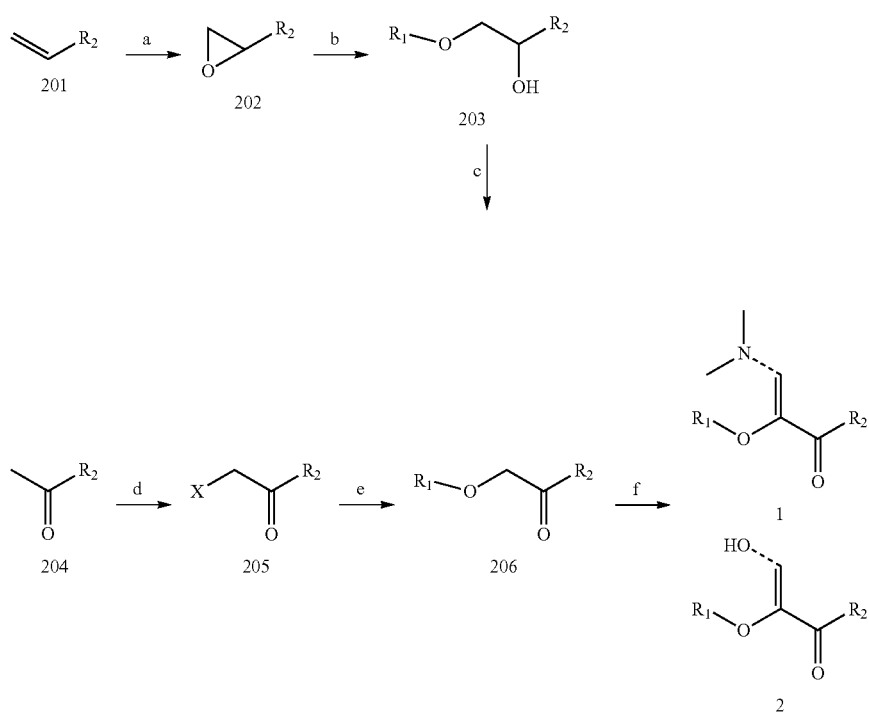

X is Halogen
R² being aryl or heteroaryl

Oxirane compounds 202 (Scheme 4), are known or can be prepared by epoxidation of olefin precursors 201 by methods well known in the art, as e.g. use of m-chloro perbenzoic acids in solvents like dichloromethane (step a). Reaction of suitable hydroxy-heterocycles with oxiranes 202 in the presence of a base like sodium, potassium or cesium carbonate or sodium hydride in solvents like tetrahydrofuran, dimethyl sulfoxide, N,N-dimethylformamide or 1,3-dimethyl-3,4,5,6-tetrahydro-2(1H)-pyrimidinone (DMPU) at temperatures between room temperature and about 100° C. gives adducts 203 (step b). Adducts 203 can be oxidized to keto compounds 206 e.g. using Swern conditions (oxalyl chloride, dimethyl sulfoxide, triethyl amine in dichloromethane between −78° C. and RT, step c). Alternatively, keto compounds 206 can be prepared from aryl acetyl compounds 204 by i) halogenation at the CH₃—CO moiety (e.g. by reaction with trimethylphenylammoniumtribromide in dichloromethane at RT) followed ii) by reaction with suitable hydroxy-heterocycles in the presence of a base like sodium, potassium or cesium carbonate or sodium hydride in solvents like tetrahydrofuran, dimethyl sulfoxide, N,N-dimethylformamide or 1,3-dimethyl-3,4,5,6-tetrahydro-2 (1H)-pyrimidinone (DMPU) at temperatures between room temperature and about 100° C. (steps, d, e). Aryloxy-ketones 206 react i) with 1,1-dimethoxy-N,N-dimethyl-methanamine in N,N-dimethylformamide at temperatures between about 50° C. and about 180° C. preferably with microwave heating to form dimethylamino adducts 1 or ii) with a formic acid alkyl ester and a base like a sodium alkylate in an alcoholic solvent at temperatures between about 0° C. and room temperature to give hydroxy-alkene compounds 2 (step f).

Scheme 5

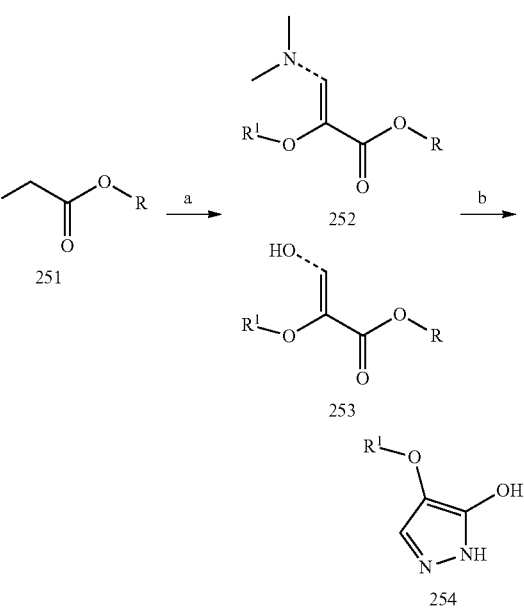

-continued

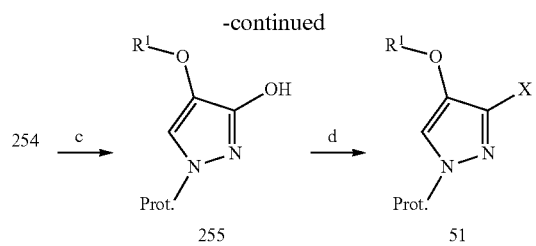

X is Halogen or OSO$_2$CF$_3$

R being alkyl

Pyrazoles 51 carrying a halogen or a triflate moiety are known, can be prepared by methods well known in the art or as described in Scheme 5. Aryloxy-ester compounds 251 react i) with 1,1-dimethoxy-N,N-dimethyl-methanamine in N,N-dimethylformamide at temperatures between about 50° C. and about 180° C. preferably with microwave heating to form dimethylamino adducts 252 or ii) with a formic acid alkyl ester and a base like a sodium alkylate in an alcoholic solvent at temperatures between about 0° C. and room temperature to give hydroxy-alkene compounds 253 (Scheme 5, step a). Dimethylamino-alkene compounds 252 or hydroxy-alkene compounds 253 react with hydrazine hydrate in the presence of an acid like e.g. aqueous hydrochloric acid in solvents like tetrahydrofuran, dioxane, methanol, ethanol or mixtures thereof at elevated temperatures e.g. between about 50° C. and the reflux temperature of the solvents to form pyrazole compounds 254 (step b). Introduction of a protecting group in pyrazole compounds 254, e.g. a THP group (treatment with 3,4-dihydro-2H-pyran and p-toluenesulfonic acid monohydrate in DCM at room temperature) gives protected pyrazoles 255 (step c). Hydroxy-pyrazoles 255 can be converted into pyrazoles 51 carrying a halogen or a triflate moiety e.g. by treatment with trifluoromethanesulfonic anhydride in DCM in the presence of trietylamine preferably at room temperature or by reaction by phosphoroxychloride in a solvent like pyridine preferably at elevated temperature (step d).

Also an embodiment of the present invention is a process to prepare a compound of formula (I) as defined above comprising the reaction of a compound of formula (II) or (III) in the presence of hydrazine hydrate;

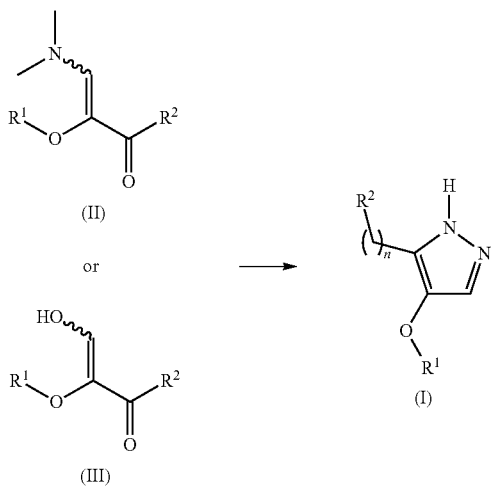

wherein R$^1$ and R$^2$ are described herein and n is zero.

In particular, in the presence of an acid, particularly aqueous hydrochloric acid, in solvents like tetrahydrofuran, dioxane, methanol, ethanol or mixtures thereof at elevated temperatures, particularly between about 50° C. and the reflux temperature of the solvents.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC (CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

| Example | EC50 human CYP11B2 nM | EC50 human CYP11B1 nM |
|---|---|---|
| 1 | 0.0298 | 1.0342 |
| 2 | 0.4629 | 1.9692 |

| Example | EC50 human CYP11B2 nM | EC50 human CYP11B1 nM |
|---|---|---|
| 3 | 0.3231 | 1.375 |
| 4 | 0.0001 | 0.0013 |
| 5 | 0.0025 | 0.0116 |
| 6 | 0.0026 | 0.0518 |
| 7 | 0.0244 | 0.8611 |
| 8 | 0.004 | 0.0757 |
| 9 | 0.0079 | 0.1669 |
| 10 | 0.0608 | 0.8345 |
| 11 | 0.0458 | 0.4331 |
| 12 | 0.0264 | 0.6004 |
| 13 | 0.4081 | 2.4679 |
| 14 | 2.0278 | 2.6661 |
| 15 | 0.0186 | 0.1592 |
| 16 | 0.0845 | 1.969 |
| 17 | 0.0608 | 0.5219 |
| 18 | 0.0239 | 0.4619 |
| 19 | 0.1134 | 0.3867 |
| 20 | 0.3113 | 3.3861 |
| 21 | 0.1005 | 0.8415 |
| 22 | 0.0421 | 0.6108 |
| 23 | 0.0268 | 0.723 |
| 24 | 0.0102 | 0.3504 |
| 25 | 0.0002 | 0.0185 |
| 27 | 0.575 | 3.319 |
| 28 | 0.0015 | 0.1343 |
| 29 | 0.0075 | 0.1605 |
| 30 | 0.008 | 0.1905 |
| 31 | 0.1913 | 1.8211 |
| 32 | 0.0458 | 0.5423 |
| 33 | 0.0175 | 0.0313 |
| 34 | 0.0392 | 0.2616 |
| 35 | 0.0015 | 0.0686 |
| 36 | 0.0168 | 0.0529 |
| 37 | 0.3174 | 10.5232 |
| 38 | 0.0319 | 0.3213 |
| 39 | 0.0342 | 1.1563 |
| 40 | 1.4989 | >30 |
| 41 | 0.0001 | 0.0005 |
| 42 | 0.0298 | 0.3446 |
| 43 | 0.0416 | 0.5581 |
| 44 | 0.3129 | >30 |
| 45 | 0.3966 | 2.3971 |
| 46 | 1.0512 | 10.7263 |
| 47 | 0.2811 | 0.1587 |
| 48 | 0.0204 | 0.0834 |
| 49 | 0.0132 | 0.085 |
| 50 | 0.0104 | 0.0516 |
| 51 | 0.0095 | 0.0513 |
| 52 | 0.0148 | 0.0323 |
| 53 | 0.0238 | 0.1981 |
| 54 | 0.0035 | 0.0465 |
| 55 | 0.0331 | 0.2882 |
| 56 | 0.0095 | 0.0936 |
| 58 | 0.215 | 1.5088 |
| 59 | 0.0109 | 0.102 |
| 60 | 0.054 | 1.0021 |
| 62 | 0.3696 | 2.2815 |
| 63 | 0.1502 | 6.4697 |
| 64 | 0.4047 | 8.1579 |
| 65 | 1.4137 | 5.9082 |
| 66 | 0.0685 | 2.0585 |
| 67 | 0.2506 | 3.2715 |
| 68 | 0.4388 | 2.4038 |
| 69 | 0.0169 | 0.0477 |
| 70 | 0.0106 | 0.0383 |
| 71 | 0.6557 | 5.8757 |
| 72 | 1.6305 | 19.2693 |
| 73 | 0.1035 | 0.4114 |
| 74 | 0.0197 | 0.0362 |
| 75 | 0.0085 | 0.1386 |
| 76 | 0.0002 | 0.0068 |
| 77 | 0.0003 | 0.0114 |
| 78 | 0.0003 | 0.0107 |
| 79 | 0.0002 | 0.0025 |
| 80 | 0.0003 | 0.0069 |
| 81 | 0.0025 | 0.1706 |
| 82 | 0.5201 | 4.301 |
| 83 | 0.3209 | 2.8774 |
| 84 | 0.0004 | 0.0173 |
| 85 | 0.0003 | 0.0052 |
| 86 | 0.0043 | 0.028 |
| 88 | 0.1473 | 25.912 |
| 89 | 0.2305 | 7.7551 |
| 90 | 0.1589 | 1.5788 |
| 91 | 1.2603 | 9.0144 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitors of CYP11B2. The compounds of formula (I) or their pharmaceutically acceptable salts and esters herein display also variable inhibition of CYP11B1 but present an improved selectivity towards CYP11B2 versus CYP11B1. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestion and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the persons skilled in the art, such as e.g. chiral chromatography or crystallization.

EXAMPLES

All examples and intermediates were prepared under argon atmosphere if not specified otherwise.
Pyrazoles carrying a hydrogen substituent at any of the two nitrogen atoms and not symmetrical substituents at the 3 carbon atoms always exist in two tautomeric forms. Formulas and names describe any of the two forms.

Intermediate A-1

(Z and/or E)-2-(4-Chlorophenoxy)-1-(2,3-difluorophenyl)-3-(dimethylamino)prop-2-en-1-one

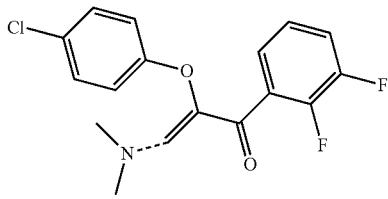

[A] 2-Bromo-1-(2,3-difluorophenyl)ethanone

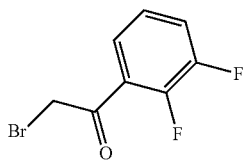 [SMILES: O=C(CBr)c1cccc(F)c1F]

To a solution of 2,3-difluoroacetophenone (0.6 g, 3.84 mmol) in DCM (10 mL) was added trimethylphenylammoniumtribromide (1.59 g, 4.23 mmol) portion wise and the reaction mixture was then stirred at room temperature overnight. The mixture was diluted with DCM, poured into water (10 mL) and the aqueous layer was extracted with DCM (2×20 mL). The combined organics were washed with brine, dried over Na$_2$SO$_4$, filtered and evaporated. The residue was purified by silica gel flash chromatography eluting with a 0 to 20% EtOAc-heptane gradient to give the title compound (0.868 g, 96%) as a colorless oil.

[B] 2-(4-Chlorophenoxy)-1-(2,3-difluorophenyl)ethanone

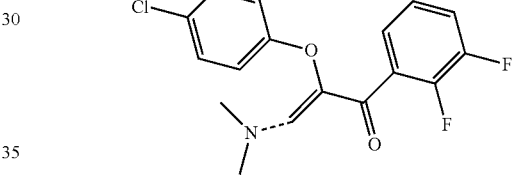

To a solution of 2-bromo-1-(2,3-difluorophenyl)ethanone (0.1 g, 0.425 mmol) in DMF (1 mL) was added 4-chlorophenol (0.055 g, 0.425 mmol) followed by K$_2$CO$_3$ (0.147 g, 1.06 mmol) and the reaction mixture was then stirred at room temperature for 2.5 h. The mixture was diluted with EtOAc, poured into 1N aqueous HCl solution (2 mL) and the aqueous layer was extracted with EtOAc (2×10 mL). The combined organics were washed with brine, dried over Na$_2$SO$_4$, filtered and evaporated. The residue was purified by silica gel flash chromatography eluting with a 0 to 30% EtOAc-heptane gradient to give the title compound (0.055 g, 44%) as an off white solid.

[C] (Z and/or E)-2-(4-Chlorophenoxy)-1-(2,3-difluorophenyl)-3-(dimethylamino)prop-2-en-1-one In a microwave vial, 2-(4-chlorophenoxy)-1-(2,3-difluorophenyl)ethanone (0.055 g, 0.195 mmol) and DMF-DMA (0.046 g, 0.389 mmol) were dissolved in DMF (1 mL) and the reaction mixture was then heated to 80° C. for 15 min under microwave irradiation. The mixture was evaporated to dryness and the residue purified by silica gel flash chromatography eluting with a 10 to 60% EtOAc-heptane gradient to give the title compound (0.034 g, 52%) as an off white solid. MS: 338.1 (M+H$^+$).

The following intermediates listed in Table 1 were prepared in analogy to the procedures described for the preparation of intermediate A-1 by using appropriate starting materials:

TABLE 1

| Intermediate | Name Aspect | Reactants | MS (M + H$^+$) |
|---|---|---|---|
| A-2 | (Z and/or E)-1-(4-Chlorophenyl)-3-(dimethylamino)-2-(4-methoxyphenoxy)prop-2-en-1-one<br><br>yellow oil | 2-bromo-1-(4-chlorophenyl)ethanone, 4-methoxyphenol | 332.4 |

TABLE 1-continued

| Intermediate | Name<br>Aspect | Reactants | MS<br>(M + H+) |
|---|---|---|---|
| A-3 | (Z and/or E)-2-(4-Chlorophenoxy)-1-(4-chlorophenyl)-3-(dimethylamino)prop-2-en-1-one<br>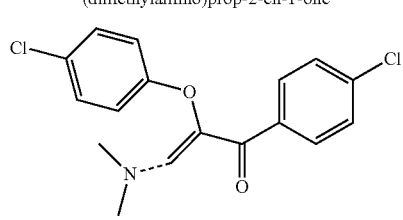<br>orange oil | 2-bromo-1-(4-chlorophenyl)ethanone, 4-chlorophenol | 336.4 |
| A-4 | (Z and/or E)-2-(4-Chlorophenoxy)-3-(dimethylamino)-1-(2-methoxyphenyl)prop-2-en-1-one<br>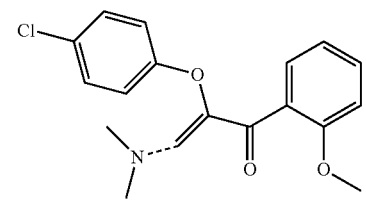<br>colorless amorphous solid | 2-bromo-1-(2-methoxyphenyl)ethanone, 4-chlorophenol | 332.4 |
| A-5 | (Z and/or E)-2-(4-Chlorophenoxy)-1-(2,4-dimethoxyphenyl)-3-(dimethylamino)prop-2-en-1-one<br>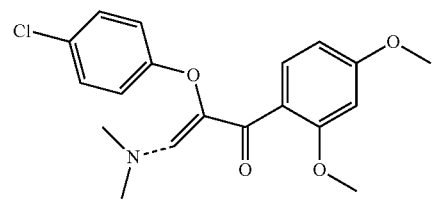<br>colorless amorphous solid | 2-bromo-1-(2,4-dimethoxyphenyl)ethanone, 4-chlorophenol | 362.4 |
| A-6 | (Z and/or E)-2-(4-Chlorophenoxy)-1-(2-chlorophenyl)-3-(dimethylamino)prop-2-en-1-one<br>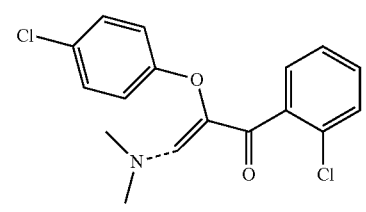<br>light yellow solid | 2-bromo-1-(2-chlorophenyl)ethanone, 4-chlorophenol | 336.4 |
| A-7 | (Z and/or E)-2-(4-Chlorophenoxy)-3-(dimethylamino)-1-[2-(trifluoromethoxy)phenyl]prop-2-en-1-one<br>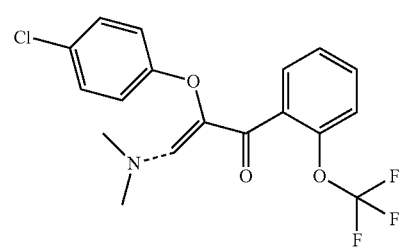<br>light yellow oil | 2-bromo-1-[2-(trifluoromethoxy)phenyl]ethanone, 4-chlorophenol | 386.4 |

TABLE 1-continued

| Intermediate | Name / Aspect | Reactants | MS (M + H⁺) |
|---|---|---|---|
| A-8 | (Z and/or E)-2-(4-Chlorophenoxy)-1-[2-(difluoromethoxy)phenyl]-3-(dimethylamino)prop-2-en-1-one<br>orange oil | 2-bromo-1-[2-(difluoromethoxy)phenyl]ethanone, 4-chlorophenol | 368.4 |
| A-9 | (Z and/or E)-2-(4-Chlorophenoxy)-3-(dimethylamino)-1-(2-fluorophenyl)prop-2-en-1-one<br>orange oil | 2-bromo-1-(2-fluorophenyl)ethanone, 4-chlorophenol | 320.4 |
| A-10 | (Z and/or E)-1-(5-Chloro-2-methoxy-phenyl)-2-(4-chlorophenoxy)-3-(dimethylamino)prop-2-en-1-one<br>light yellow amorphous solid | 2-bromo-1-(5-chloro-2-methoxy-phenyl)ethanone, 4-chlorophenol | 366.5 |
| A-11 | (Z and/or E)-1-(4-Chloro-2-fluoro-phenyl)-2-(4-chlorophenoxy)-3-(dimethylamino)prop-2-en-1-one<br>yellow solid | 2-bromo-1-(4-chloro-2-fluoro-phenyl)ethanone, 4-chlorophenol | 354.3 |

TABLE 1-continued

| Intermediate | Name Aspect | Reactants | MS (M + H+) |
|---|---|---|---|
| A-12 | (Z and/or E)-2-(4-Chlorophenoxy)-3-(dimethylamino)-1-(4-methylsulfonylphenyl)prop-2-en-1-one<br />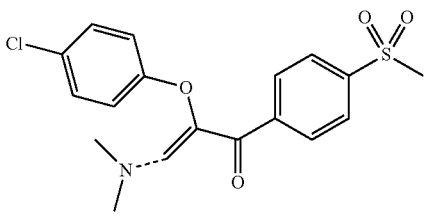<br />yellow solid | 1-(4-methylsulfonylphenyl)ethanone, 4-chlorophenol | 380.4 |
| A-13 | (Z and/or E)-2-(4-Chlorophenoxy)-3-(dimethylamino)-1-[2-fluoro-4-(trifluoromethyl)phenyl]prop-2-en-1-one<br />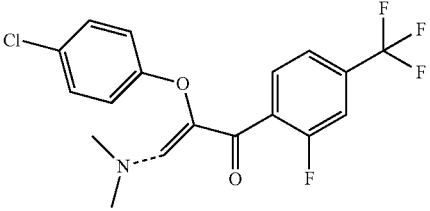<br />brown amorphous solid | 2-bromo-1-[2-fluoro-4-(trifluoromethyl)phenyl]ethanone, 4-chlorophenol | 388.4 |
| A-14 | (Z and/or E)-2-(4-Chlorophenoxy)-3-(dimethylamino)-1-[4-(trifluoromethyl)phenyl]prop-2-en-1-one<br />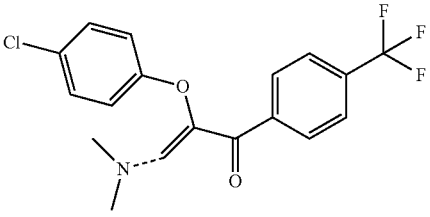<br />yellow oil | 2-bromo-1-[4-(trifluoromethyl)phenyl]ethanone, 4-chlorophenol | 370.5 |
| A-15 | (Z and/or E)-2-(4-Chlorophenoxy)-1-(2,4-difluorophenyl)-3-(dimethylamino)prop-2-en-1-one<br />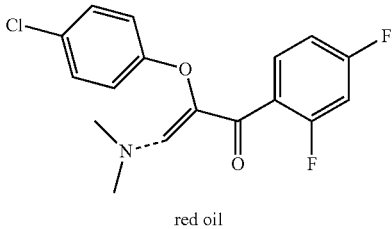<br />red oil | 2-bromo-1-(2,4-difluorophenyl)ethanone, 4-chlorophenol | 338.5 |
| A-16 | (Z and/or E)-3-(Dimethylamino)-1-(4-methylsulfonylphenyl)-2-[4-(trifluoromethyl)phenoxy]prop-2-en-1-one<br />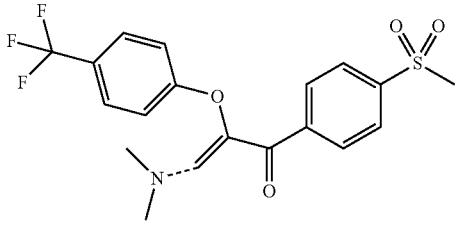<br />light red solid | 1-(4-methylsulfonylphenyl)ethanone, 4-(trifluoromethyl)phenol | 414.4 |

TABLE 1-continued

| Intermediate | Name / Aspect | Reactants | MS (M + H+) |
|---|---|---|---|
| A-17 | (Z and/or E)-1-(2-Chloro-4-methylsulfanyl-phenyl)-2-(4-chlorophenoxy)-3-(dimethylamino)prop-2-en-1-one<br>light yellow solid | 1-(2-chloro-4-methylsulfanyl-phenyl)ethanone, 4-chlorophenol | 382.3 |
| A-18 | 4-[(Z and/or E)-2-(Dimethylamino)-1-(4-methylsulfonylbenzoyl)vinyloxy]benzonitrile<br>light brown solid | 1-(4-methylsulfonylphenyl)ethanone, 4-hydroxybenzonitrile | 371.5 |
| A-19 | (Z and/or E)-1-(2-Chlorophenyl)-2-[(6-chloro-3-pyridyl)oxy]-3-(dimethylamino)prop-2-en-1-one<br>brown amorphous solid | 2-bromo-1-(2-chlorophenyl)ethanone, 6-chloropyridin-3-ol | 337.4 |
| A-20 | (Z and/or E)-1-(2-Chlorophenyl)-3-(dimethylamino)-2-[(6-methyl-3-pyridyl)oxy]prop-2-en-1-one<br>brown amorphous solid | 2-bromo-1-(2-chlorophenyl)ethanone, 6-methylpyridin-3-ol | 317.4 |

TABLE 1-continued

| Intermediate | Name Aspect | Reactants | MS (M + H+) |
|---|---|---|---|
| A-21 | (Z and/or E)-1-(2,4-Dichlorophenyl)-3-(dimethylamino)-2-[(6-fluoro-2-pyridyl)oxy]prop-2-en-1-one<br />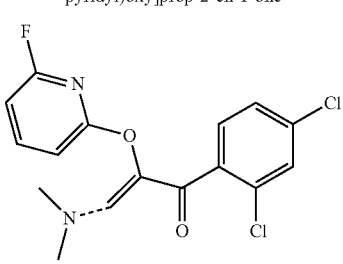<br />yellow amorphous solid | 2-bromo-1-(2,4-dichlorophenyl)ethanone, 6-fluoropyridin-2-ol | 355.3 |
| A-22 | (Z and/or E)-1-(2,4-Dichlorophenyl)-3-(dimethylamino)-2-[(6-methyl-2-pyridyl)oxy]prop-2-en-1-one<br />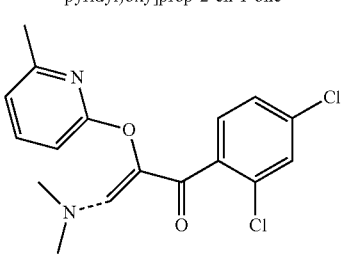<br />light brown amorphous solid | 2-bromo-1-(2,4-dichlorophenyl)ethanone, 6-methylpyridin-2-ol | 351.4 |
| A-23 | (Z and/or E)-1-(2-Chlorophenyl)-3-(dimethylamino)-2-[4-(trifluoromethyl)phenoxy]prop-2-en-1-one<br />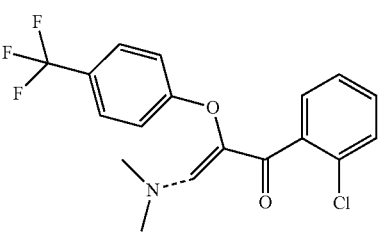<br />yellow amorphous solid | 2-bromo-1-(2-chlorophenyl)ethanone, 4-(trifluoromethyl)phenol | 370.1 |
| A-24 | (Z and/or E)-2-(4-Chloro-2-fluoro-phenoxy)-1-(2-chlorophenyl)-3-(dimethylamino)prop-2-en-1-one<br />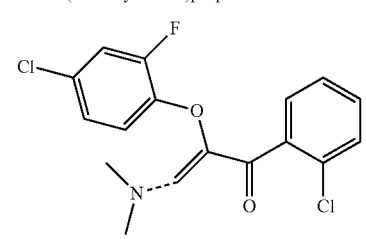<br />yellow amorphous solid | 2-bromo-1-(2-chlorophenyl)ethanone, 4-chloro-2-fluoro-phenol | 354.1 |

TABLE 1-continued

| Intermediate | Name Aspect | Reactants | MS (M + H+) |
|---|---|---|---|
| A-25 | 4-[(Z and/or E)-1-(2-Chlorobenzoyl)-2-(dimethylamino)vinyloxy]benzonitrile<br>yellow amorphous solid | 2-bromo-1-(2-chlorophenyl)ethanone, 4-hydroxybenzonitrile | 327.1 |
| A-26 | 4-[(Z and/or E)-1-(2-Chloro-4-methylsulfanyl-benzoyl)-2-(dimethylamino)vinyloxy]benzonitrile<br>orange solid | 1-(2-chloro-4-methylsulfanyl-phenyl)ethanone, 4-hydroxybenzonitrile | 373.5 |
| A-27 | (Z and/or E)-1-(4-Chloro-2-fluoro-phenyl)-3-(dimethylamino)-2-[4-(trifluoromethyl)phenoxy]prop-2-en-1-one<br>orange solid | 1-(4-chloro-2-fluoro-phenyl)ethanone, 4-(trifluoromethyl)phenol | 388.5 |
| A-28 | 4-[(Z and/or E)-1-(2-Chlorobenzoyl)-2-(dimethylamino)vinyloxy]-3-fluoro-benzonitrile<br>yellow amorphous solid | 2-bromo-1-(2-chlorophenyl)ethanone, 3-fluoro-4-hydroxy-benzonitrile | 345.2 |
| A-29 | 4-[(Z and/or E)-1-(2,3-Difluorobenzoyl)-2-(dimethylamino)vinyloxy]benzonitrile<br>light yellow solid | 2-bromo-1-(2,3-difluorophenyl)ethanone (intermediate A-1 [A]), 4-hydroxybenzonitrile | 329.2 |

TABLE 1-continued

| Intermediate | Name Aspect | Reactants | MS (M + H+) |
|---|---|---|---|
| A-30 | 4-[(Z and/or E)-1-(3-Chloro-2-fluoro-benzoyl)-2-(dimethylamino)vinyloxy]benzonitrile<br><br>light red solid | 1-(3-chloro-2-fluoro-phenyl)-ethanone, 4-hydroxy-benzonitrile | 345.1 |
| A-31 | (Z and/or E)-1-(3-Chloro-2-fluoro-phenyl)-2-(4-chlorophenoxy)-3-(dimethylamino)prop-2-en-1-one<br><br>light brown amorphous solid | 1-(3-chloro-2-fluoro-phenyl)-ethanone, 4-chlorophenol | 354.1 |
| A-32 | 4-[(Z and/or E)-1-(3-Chlorobenzoyl)-2-(dimethylamino)vinyloxy]benzonitrile<br><br>yellow oil | 1-(3-chloro-phenyl)-ethanone, 4-hydroxy-benzonitrile | 327.2 |
| A-33 | Methyl 3-[(Z and/or E)-2-(4-cyanophenoxy)-3-(dimethylamino)prop-2-enoyl]benzoate<br><br>yellow oil | methyl 3-acetylbenzoate, 4-hydroxy-benzonitrile | 351.2 |
| A-34 | (Z and/or E)-1-(2-Chloro-3-fluoro-phenyl)-2-(4-chlorophenoxy)-3-(dimethylamino)prop-2-en-1-one<br><br>light yellow amorphous solid | 1-(2-chloro-3-fluoro-phenyl)ethanone, 4-chlorophenol | 354.2 |

TABLE 1-continued

| Intermediate | Name Aspect | Reactants | MS (M + H+) |
|---|---|---|---|
| A-35 | 4-[(Z and/or E)-1-(2-Chloro-3-fluoro-benzoyl)-2-(dimethylamino)vinyloxy]benzonitrile<br>light brown amorphous solid | 1-(2-chloro-3-fluoro-phenyl)ethanone, 4-hydroxy-benzonitrile | 345.2 |
| A-36 | 4-[(Z and/or E)-1-(3-Benzyloxybenzoyl)-2-(dimethylamino)vinyloxy]benzonitrile<br>yellow amorphous solid | 1-(3-benzyloxyphenyl)-ethanone, 4-hydroxy-benzonitrile | 399.3 |
| A-37 | 4-[(Z and/or E)-1-(2-Chloropyridine-4-carbonyl)-2-(dimethylamino)vinyloxy]benzonitrile<br>yellow amorphous solid | 2-bromo-1-(2-chloro-4-pyridyl)-ethanone, 4-hydroxy-benzonitrile | 328.2 |
| A-38 | Methyl 3-[(Z and/or E)-2-(4-cyano-2-fluoro-phenoxy)-3-(dimethylamino)prop-2-enoyl]benzoate<br>brown amorphous solid | methyl 3-acetylbenzoate, 3-fluoro-4-hydroxy-benzonitrile | 369.2 |
| A-39 | Ethyl 2-[(Z and/or E)-2-(4-cyanophenoxy)-3-(dimethylamino)prop-2-enoyl]benzoate<br>red amorphous solid | ethyl 2-acetylbenzoate, 4-hydroxy-benzonitrile | 365.2 |

TABLE 1-continued

| Intermediate | Name Aspect | Reactants | MS (M + H⁺) |
|---|---|---|---|
| A-40 | 4-[(Z and/or E)-1-(2-Benzyloxybenzoyl)-2-(dimethylamino)vinyloxy]benzonitrile<br>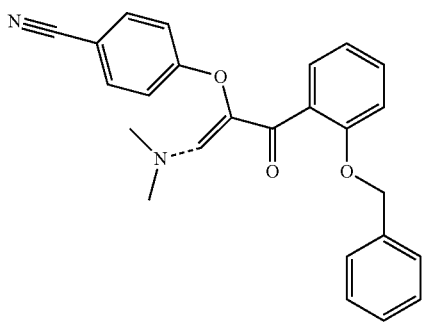<br>yellow amorphous solid | 1-(2-benzyloxyphenyl)-ethanone, 4-hydroxy-benzonitrile | 399.2 |

Intermediate B-1

(rac)-3-[4-(4-Cyanophenoxy)-1-tetrahydropyran-2-yl-pyrazol-3-yl]benzoic acid

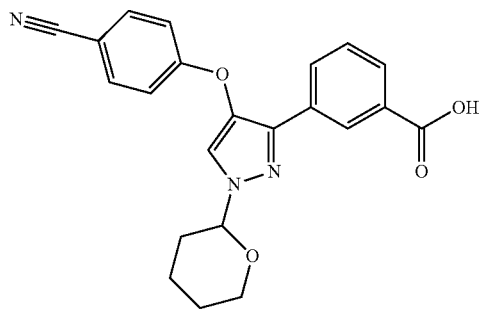 [SMILES: N#Cc1ccc(Oc2cn(C3CCCCO3)nc2-c2cccc(C(=O)O)c2)cc1]

[A] (rac)-Methyl 3-[4-(4-cyanophenoxy)-1-tetrahydropyran-2-yl-pyrazol-3-yl]benzoate

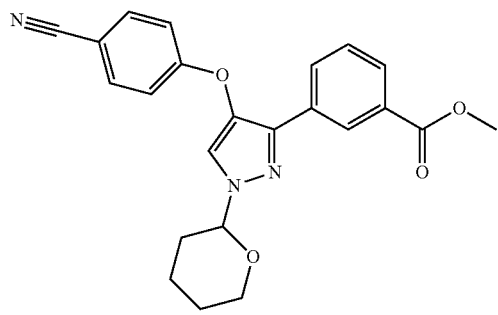 [SMILES: COC(=O)c1cccc(-c2nn(C3CCCCO3)cc2Oc2ccc(C#N)cc2)c1]

To a suspension of methyl 3-[4-(4-cyanophenoxy)-1H-pyrazol-3-yl]benzoate (example 33) (0.207 g, 0.616 mmol) in DCM (10 mL) was added 3,4-dihydro-2H-pyran (0.104 g, 1.23 mmol) followed by p-toluenesulfonic acid monohydrate (0.023 g, 0.123 mmol) and the reaction mixture was then stirred at room temperature for 48 h. The mixture was diluted with DCM, poured into water (20 mL) and the aqueous layer was extracted with DCM (2×40 mL). The combined organics were washed with brine, dried over Na₂SO₄, filtered and evaporated. The residue was then purified by silica gel flash chromatography eluting with a 0 to 40% EtOAc-heptane gradient to give the title compound (0.215 g, 82%) as light yellow amorphous solid. MS: 404.3 (M+H⁺).

[B] (rac)-3-[4-(4-Cyanophenoxy)-1-tetrahydropyran-2-yl-pyrazol-3-yl]benzoic acid

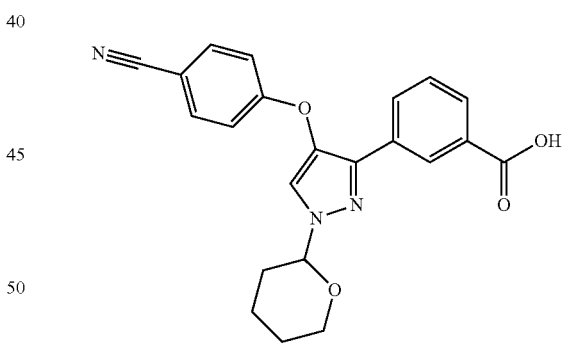

To a solution of (rac)-methyl 3-[4-(4-cyanophenoxy)-1-tetrahydropyran-2-yl-pyrazol-3-yl]benzoate (0.215 g, 0.532 mmol) in THF (10 mL)/water (5 mL) was added LiOH (0.038 g, 1.6 mmol) and the reaction mixture was stirred at room temperature for 18 h. The mixture was diluted with EtOAc, poured into a 1M aqueous HCl solution (10 mL) and the aqueous layer was extracted with EtOAc (2×40 mL). The combined organics were washed with brine, dried over Na₂SO₄, filtered and evaporated to dryness to give the title compound (0.218 g, 95%) as light yellow amorphous solid. MS: 390.3 (M+H⁺).

Intermediate B-2

(rac)-[4-(4-Cyanophenoxy)-1-tetrahydropyran-2-yl-pyrazol-3-yl] trifluoromethanesulfonate

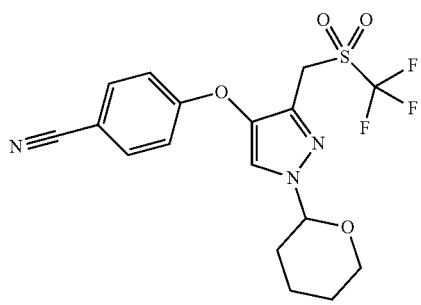 [SMILES: N#Cc1ccc(Oc2cn(C3CCCCO3)nc2CS(=O)(=O)C(F)(F)F)cc1]

[A] Ethyl 2-(4-cyanophenoxy)acetate

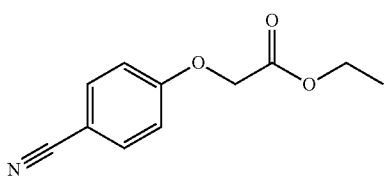

To a solution of 4-hydroxybenzonitrile (0.636 g, 5.34 mmol) in acetone (10 mL) was added K$_2$CO$_3$ (0.738 g, 5.34 mmol), followed by ethyl-2-chloroacetate (0.687 g, 5.61 mmol) and the reaction mixture was heated at reflux overnight. The solvent was evaporated, the residue taken up in EtOAc, then poured into water (20 mL) and the aqueous layer was extracted with EtOAc (50 mL). The combined organics were washed with brine, dried over Na$_2$SO$_4$, filtered and evaporated to dryness to give the title compound (1.046 g, 95%) as white solid, which was used in the next step with no further purification.

[B] Ethyl (E and/or Z)-2-(4-cyanophenoxy)-3-hydroxy-prop-2-enoate

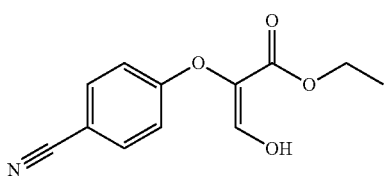 [SMILES: CCOC(=O)/C(=C\O)Oc1ccc(C#N)cc1]

To a suspension of NaH 60% in mineral oil (0.245 g, 6.12 mmol) in THF (3 mL) cooled to 0° C. (ice bath) was added a solution of ethyl 2-(4-cyanophenoxy)acetate (1.046 g, 5.1 mmol) and ethyl formate (0.415 g, 5.61 mmol) in THF (5 mL) and the reaction mixture was stirred at room temperature overnight. The mixture was quenched with MeOH (2.5 mL) and then evaporated to dryness. The residue was triturated in DCM and the solvent was decanted to give a sticky solid. This material was then dissolved in MeOH and evaporated to dryness to give the title compound (1.19 g, 95%) as yellow oil, which was used as crude mixture in the next step. MS: 232.2 (M–H$^+$).

[C] 4-[(3-Hydroxy-1H-pyrazol-4-yl)oxy]benzonitrile

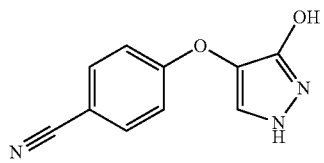 [SMILES: N#Cc1ccc(Oc2c[nH]nc2O)cc1]

To a solution of ethyl (E and/or Z)-2-(4-cyanophenoxy)-3-hydroxy-prop-2-enoate (1.2 g, 5.15 mmol) in MeOH (15 ml) was added hydrazine hydrate (0.309 g, 6.17 mmol) and the reaction mixture was heated to 65° C. for 1 h. The mixture was evaporated to dryness and the residue was purified by silica gel flash chromatography eluting with a 0 to 10% MeOH-DCM gradient to give the title compound (0.637 g, 61%) as orange solid. MS: 202.1 (M+H$^+$).

[D] (rac)-4-(3-Hydroxy-1-tetrahydropyran-2-yl-pyrazol-4-yl)oxybenzonitrile

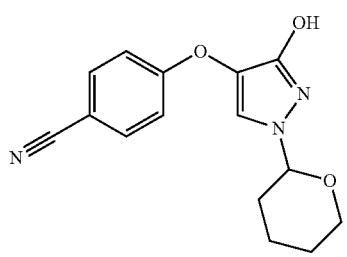 [SMILES: N#Cc1ccc(Oc2cn(C3CCCCO3)nc2O)cc1]

To a suspension of 4-[(3-hydroxy-1H-pyrazol-4-yl)oxy]benzonitrile (0.2 g, 0.994 mmol) in DCM (10 mL) was added p-toluenesulfonic acid monohydrate (0.038 g, 0.199 mmol) followed by 3,4-dihydro-2H-pyran (0.1 g, 1.19 mmol) and the reaction mixture was stirred at room temperature overnight. The solid precipitate was filtered off. The mother liquors were evaporated to dryness; the residue was triturated in DCM, filtered and the residue combined with the first solid precipitate. Both materials were further dried to give the title compound (0.248 g, 85%) as a colorless solid. MS: 286.2 (M+H$^+$).

[E] (rac)-[4-(4-Cyanophenoxy)-1-tetrahydropyran-2-yl-pyrazol-3-yl] trifluoromethanesulfonate

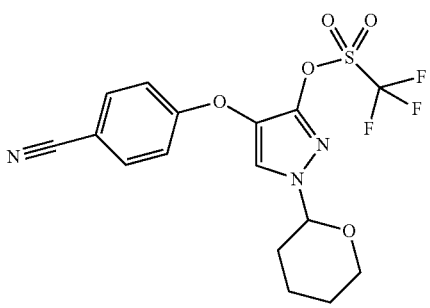 [SMILES: N#Cc1ccc(Oc2cn(C3CCCCO3)nc2OS(=O)(=O)C(F)(F)F)cc1]

To a solution of (rac)-4-(3-hydroxy-1-tetrahydropyran-2-yl-pyrazol-4-yl)oxybenzonitrile (0.115 g, 0.403 mmol) in DCM (1.5 mL) was added TEA (0.061 g, 0.605 mmol) followed by trifluoromethanesulfonic anhydride (0.125 g, 0.443 mmol) and the reaction mixture was stirred at room temperature for 1 h. Then, the mixture was diluted with DCM, poured into water (10 mL) and the aqueous layer was extracted with DCM (2×20 mL). The combined organics were washed with brine, dried over Na$_2$SO$_4$, filtered and evaporated. The residue was purified by silica gel flash chromatography eluting with a 0 to 30% EtOAc-heptane gradient to give the title compound (0.153 g, 91%) as colorless oil. MS: 417.1 (M$^+$).

Intermediate B-3

(rac)-tert-Butyl 4-[[4-(4-cyanophenoxy)-1-tetrahydropyran-2-yl-pyrazol-3-yl]methyl]piperazine-1-carboxylate

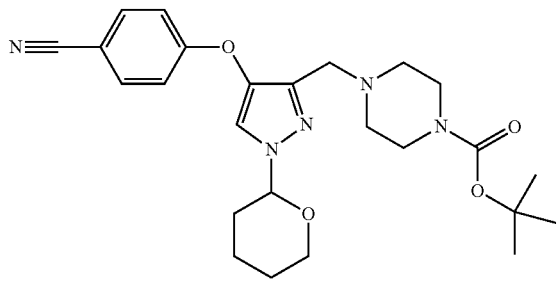 [SMILES: CC(C)(C)OC(=O)N1CCN(Cc2nn(C3CCCCO3)cc2Oc2ccc(C#N)cc2)CC1]

[A] (rac)-1-Tetrahydropyran-2-yl-4-(4,4,5,5-tetramethyl-1,3,2-dioxaborolan-2-yl)pyrazole

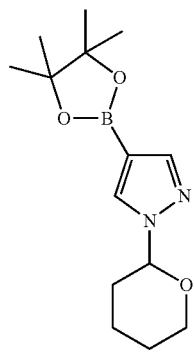 [SMILES: CC1(C)OB(c2cnn(C3CCCCO3)c2)OC1(C)C]

To a solution of 4-(4,4,5,5-tetramethyl-1,3,2-dioxaborolan-2-yl)-1H-pyrazole (1 g, 5.15 mmol) in DCE (25 mL) was added pTsOH (0.098 g, 0.515 mmol) followed by 3,4-dihydro-2H-pyran (0.867 g, 10.3 mmol) and the reaction mixture was heated to 40° C. for 3 h. The mixture was diluted with DCM, poured into a sat. NaHCO$_3$ solution (50 mL) and the aqueous layer extracted with DCM (2×75 mL). The combined organics were washed with brine, dried over Na$_2$SO$_4$, filtered and evaporated. The residue was purified by silica gel flash chromatography eluting with a 0 to 60% EtOAc-heptane gradient to give the title compound (0.818 g, 57%) as colorless solid. MS: 279.2 (M+H$^+$).

[B] (rac)-1-(Tetrahydro-2H-pyran-2-yl)-1H-pyrazol-4-ol

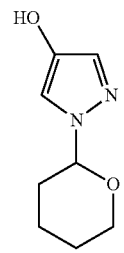

To a solution of (rac)-1-tetrahydropyran-2-yl-4-(4,4,5,5-tetramethyl-1,3,2-dioxaborolan-2-yl)pyrazole (0.818 g, 2.94 mmol) in THF (15 mL) cooled to 0° C. with an ice bath was added acetic acid (0.265 g, 4.41 mmol) followed by H$_2$O$_2$ (0.343 g, 3.53 mmol) drop wise, while keeping the temperature below 5° C. The reaction mixture was allowed to warm up to room temperature and then stirred for 2 h. The mixture was neutralized by addition of a conc. NaOH solution at 0° C., the turbid solution was decanted and evaporated to dryness. The residue was purified by silica gel flash chromatography, eluting with a 0 to 10% MeOH-DCM gradient to give the title compound (0.396 g, 80%) as colorless oil. MS: 169.1 (M+H$^+$).

[C] (rac)-4-Hydroxy-1-tetrahydropyran-2-yl-pyrazole-3-carbaldehyde

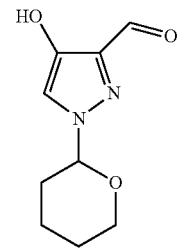

To a solution of (rac)-1-(tetrahydro-2H-pyran-2-yl)-1H-pyrazol-4-ol (0.1 g, 0.595 mmol) in acetonitrile (1 mL) were added manganese (II) chloride (0.15 g, 1.19 mmol) and TEA (0.12 g, 1.19 mmol) followed by paraformaldehyde (0.054 g, 1.78 mmol), then the reaction mixture was heated to 80° C. for 2 h. The mixture was diluted with EtOAc, poured into 1M HCl solution (5 mL) and the aqueous layer extracted with EtOAc (2×20 mL). The combined organics were dried over Na$_2$SO$_4$, filtered and evaporated to dryness to give the title compound (0.045 g, 39%) as light yellow oil. The crude product was used in the next step with no further purification. MS: 195.1 (M−H$^−$).

[D] (rac)-tert-Butyl 4-[(4-hydroxy-1-tetrahydropyran-2-yl-pyrazol-3-yl)methyl]piperazine-1-carboxylate

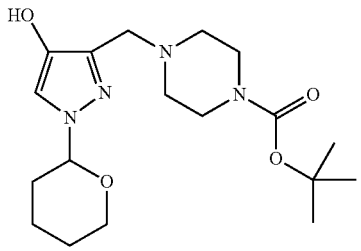 [SMILES: CC(C)(C)OC(=O)N1CCN(Cc2nn(C3CCCCO3)cc2O)CC1]

To a solution of (rac)-4-hydroxy-1-tetrahydropyran-2-yl-pyrazole-3-carbaldehyde (0.045 g, 0.229 mmol) in DCE (1.5 mL) were added tert-butyl piperazine-1-carboxylate (0.064 g, 0.344 mmol) and acetic acid (0.016 g, 0.275 mmol). The reaction mixture was stirred at room temperature for 30 min, then sodium triacetoxyborohydride (0.146 g, 0.688 mmol) was added and stirring was continued for 1.5 h. The mixture was diluted with EtOAc, poured into H$_2$O (10 mL) and the aqueous layer extracted with EtOAc (2×20 mL). The combined organics were washed with brine, dried over Na$_2$SO$_4$, filtered and evaporated. The residue was purified by silica gel flash chromatography, eluting with a 0 to 15% MeOH-DCM gradient to give the title compound (0.032 g, 38%) as light yellow oil. MS: 367.3 (M+H$^+$).

[E] (rac)-tert-Butyl 4-[[4-(4-cyanophenoxy)-1-tetrahydropyran-2-yl-pyrazol-3-yl]methyl]piperazine-1-carboxylate

In a microwave vial, (rac)-tert-butyl 4-[(4-hydroxy-1-tetrahydropyran-2-yl-pyrazol-3-yl)methyl]piperazine-1-carboxylate (0.03 g, 0.082 mmol), 4-fluorobenzonitrile (0.02 g, 0.164 mmol) and K$_2$CO$_3$ (0.025 g, 0.18 mmol) were mixed in NMP (0.6 mL) and heated in the microwave at 150° C. for 20 min. The reaction was evaporated to dryness. The residue purified by silica gel flash chromatography, eluting with a 0 to 40% EtOAc-heptane gradient to give the title compound (0.012 g, 31%) as colorless oil. MS: 468.3 (M+H$^+$).

Example 1

4-(4-Chlorophenoxy)-5-(2,3-difluorophenyl)-1H-pyrazole

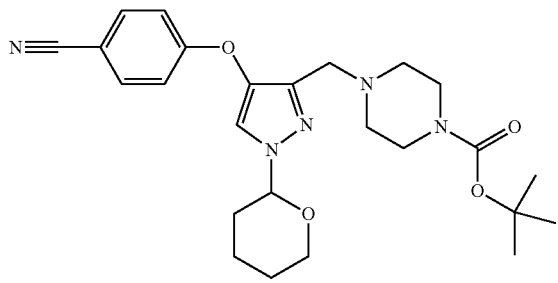 [SMILES: CC(C)(C)OC(=O)N1CCN(Cc2nn(C3CCCCO3)cc2Oc2ccc(C#N)cc2)CC1]

To a solution of (Z and/or E)-2-(4-chlorophenoxy)-1-(2,3-difluorophenyl)-3-(dimethylamino)prop-2-en-1-one (intermediate A-1) (0.034 g, 0.101 mmol) in EtOH (1 mL) was added hydrazine monohydrate (0.01 g, 0.201 mmol) followed by a 4M HCl in dioxane solution (0.028 ml, 0.111 mmol) and the reaction mixture was then heated to 65° C. for 3 h. The mixture was evaporated to dryness and the residue purified by prep-HPLC (Gemini NX 3u column, gradient 1% aq. formic acid/acetonitrile) to give the title compound (0.021 g, 68%) as a colorless waxy solid. MS: 307.4 (M+H$^+$).

The following examples listed in Table 2 were prepared in analogy to the procedure described for the preparation of examples 1 by using the indicated starting materials:

TABLE 2

| Intermediate | Name Aspect | Reactant | MS (M + H$^+$) |
|---|---|---|---|
| 2 | 3-(4-Chlorophenyl)-4-(4-methoxyphenoxy)-1H-pyrazole<br>yellow oil | (Z and/or E)-1-(4-Chlorophenyl)-3-(dimethylamino)-2-(4-methoxyphenoxy)prop-2-en-1-one (Intermediate A-2) | 301.4 |

TABLE 2-continued

| Intermediate | Name Aspect | Reactant | MS (M + H⁺) |
|---|---|---|---|
| 3 | 4-(4-Chlorophenoxy)-3-(4-chlorophenyl)-1H-pyrazole<br>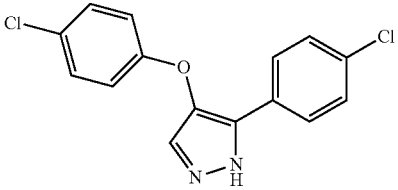<br>light yellow amorphous solid | (Z and/or E)-2-(4-Chlorophenoxy)-1-(4-chlorophenyl)-3-(dimethylamino)prop-2-en-1-one (Intermediate A-3) | 305.3 |
| 4 | 4-(4-Chlorophenoxy)-3-(2-methoxyphenyl)-1H-pyrazole<br>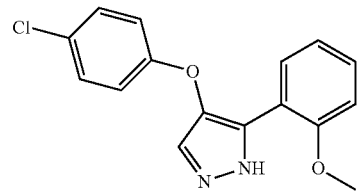<br>colorless solid | (Z and/or E)-2-(4-Chlorophenoxy)-3-(dimethylamino)-1-(2-methoxyphenyl)prop-2-en-1-one (Intermediate A-4) | 301.4 |
| 5 | 4-(4-Chlorophenoxy)-3-(2,4-dimethoxyphenyl)-1H-pyrazole<br>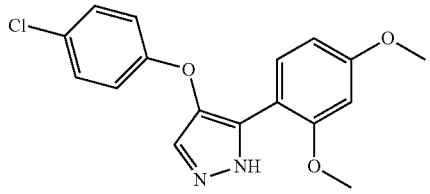<br>colorless solid | (Z and/or E)-2-(4-Chlorophenoxy)-1-(2,4-dimethoxyphenyl)-3-(dimethylamino)prop-2-en-1-one (Intermediate A-5) | 331.4 |
| 6 | 4-(4-Chlorophenoxy)-5-(2-chlorophenyl)-1H-pyrazole<br>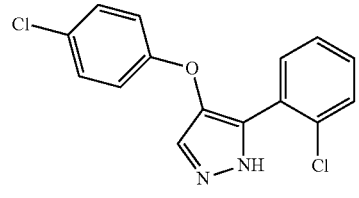<br>orange oil | (Z and/or E)-2-(4-Chlorophenoxy)-1-(2-chlorophenyl)-3-(dimethylamino)prop-2-en-1-one (Intermediate A-6) | 305.4 |
| 7 | 4-(4-Chlorophenoxy)-5-[2-(trifluoromethoxy)phenyl]-1H-pyrazole<br>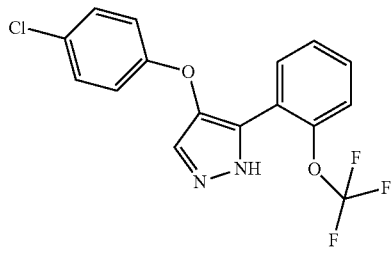<br>yellow oil | (Z and/or E)-2-(4-Chlorophenoxy)-3-(dimethylamino)-1-[2-(trifluoromethoxy)phenyl]prop-2-en-1-one (Intermediate A-7) | 355.3 |

TABLE 2-continued

| Intermediate | Name / Aspect | Reactant | MS (M + H⁺) |
|---|---|---|---|
| 8 | 4-(4-Chlorophenoxy)-5-[2-(difluoromethoxy)phenyl]-1H-pyrazole<br />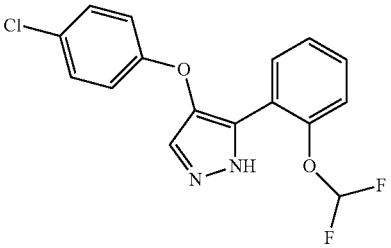<br />light yellow oil | (Z and/or E)-2-(4-Chlorophenoxy)-1-[2-(difluoromethoxy)phenyl]-3-(dimethylamino)prop-2-en-1-one (Intermediate A-8) | 337.4 |
| 9 | 4-(4-Chlorophenoxy)-5-(2-fluorophenyl)-1H-pyrazole<br />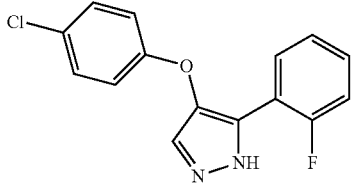<br />yellow oil | (Z and/or E)-2-(4-Chlorophenoxy)-3-(dimethylamino)-1-(2-fluorophenyl)prop-2-en-1-one (Intermediate A-9) | 289.4 |
| 10 | 3-(5-Chloro-2-methoxyphenyl)-4-(4-chlorophenoxy)-1H-pyrazole<br />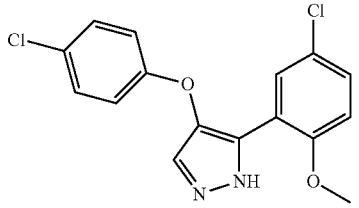<br />light yellow solid | (Z and/or E)-1-(5-Chloro-2-methoxyphenyl)-2-(4-chlorophenoxy)-3-(dimethylamino)prop-2-en-1-one (Intermediate A-10) | 335.4 |
| 11 | 5-(4-Chloro-2-fluorophenyl)-4-(4-chlorophenoxy)-1H-pyrazole<br />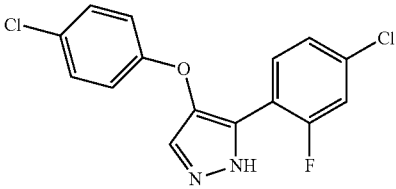<br />yellow solid | (Z and/or E)-1-(4-Chloro-2-fluoro-phenyl)-2-(4-chlorophenoxy)-3-(dimethylamino)prop-2-en-1-one (Intermediate A-11) | 323.4 |
| 12 | 4-(4-Chlorophenoxy)-5-(4-methylsulfonylphenyl)-1H-pyrazole<br />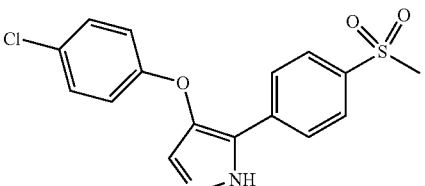<br />colorless amorphous solid | (Z and/or E)-2-(4-Chlorophenoxy)-3-(dimethylamino)-1-(4-methylsulfonylphenyl)prop-2-en-1-one (Intermediate A-12) | 349.2 |

TABLE 2-continued

| Intermediate | Name Aspect | Reactant | MS (M + H+) |
|---|---|---|---|
| 13 | 4-(4-Chlorophenoxy)-5-[2-fluoro-4-(trifluoromethyl)phenyl]-1H-pyrazole<br>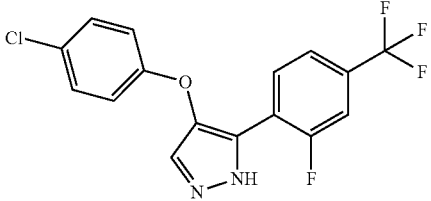<br>light brown amorphous solid | (Z and/or E)-2-(4-Chlorophenoxy)-3-(dimethylamino)-1-[2-fluoro-4-(trifluoromethyl)phenyl]prop-2-en-1-one (Intermediate A-13) | 357.3 |
| 14 | 4-(4-Chlorophenoxy)-5-[4-(trifluoromethyl)phenyl]-1H-pyrazole<br>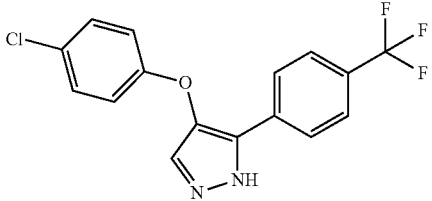<br>off-white solid | (Z and/or E)-2-(4-Chlorophenoxy)-3-(dimethylamino)-1-[4-(trifluoromethyl)phenyl]prop-2-en-1-one (Intermediate A-14) | 339.3 |
| 15 | 4-(4-Chlorophenoxy)-5-(2,4-difluorophenyl)-1H-pyrazole<br>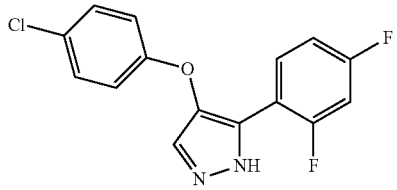<br>light yellow solid | (Z and/or E)-2-(4-Chlorophenoxy)-1-(2,4-difluorophenyl)-3-(dimethylamino)prop-2-en-1-one (Intermediate A-15) | 307.3 |
| 16 | 5-(4-Methylsulfonylphenyl)-4-[4-(trifluoromethyl)phenoxy]-1H-pyrazole<br>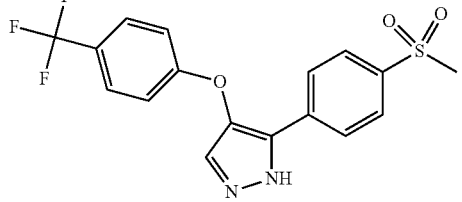<br>light yellow solid | (Z and/or E)-3-(Dimethylamino)-1-(4-methylsulfonylphenyl)-2-[4-(trifluoromethyl)phenoxy]prop-2-en-1-one (Intermediate A-16) | 383.4 |
| 17 | 5-(2-Chloro-4-methylsulfanylphenyl)-4-(4-chlorophenoxy)-1H-pyrazole<br><br>colorless amorphous solid | (Z and/or E)-1-(2-Chloro-4-methylsulfanyl-phenyl)-2-(4-chlorophenoxy)-3-(dimethylamino)prop-2-en-1-one (Intermediate A-17) | 351.2 |

TABLE 2-continued

| Intermediate | Name Aspect | Reactant | MS (M + H+) |
|---|---|---|---|
| 18 | 4-[[5-(4-Methylsulfonylphenyl)-1H-pyrazol-4-yl]oxy]benzonitrile<br />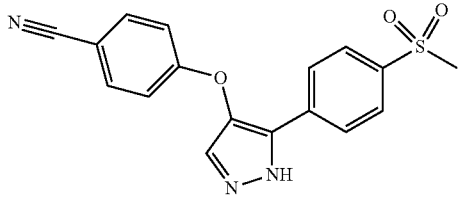<br />light yellow solid | 4-[(Z and/or E)-2-(Dimethylamino)-1-(4-methylsulfonylbenzoyl)vinyloxy]benzonitrile (Intermediate A-18) | 340.5 |
| 19 | 2-Chloro-5-[[5-(2-chlorophenyl)-1H-pyrazol-4-yl]oxy]pyridine<br />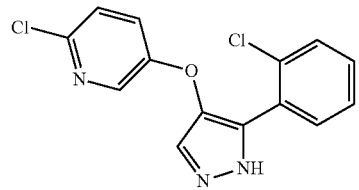<br />yellow amorphous solid | (Z and/or E)-1-(2-Chlorophenyl)-2-[(6-chloro-3-pyridyl)oxy]-3-(dimethylamino)prop-2-en-1-one (Intermediate A-19) | 306.3 |
| 20 | 5-[[5-(2-Chlorophenyl)-1H-pyrazol-4-yl]oxy]-2-methylpyridine<br /><br />colorless amorphous solid | (Z and/or E)-1-(2-Chlorophenyl)-3-(dimethylamino)-2-[(6-methyl-3-pyridyl)oxy]prop-2-en-1-one (Intermediate A-20) | 286.4 |
| 21 | 2-[[5-(2,4-Dichlorophenyl)-1H-pyrazol-4-yl]oxy]-6-fluoropyridine<br />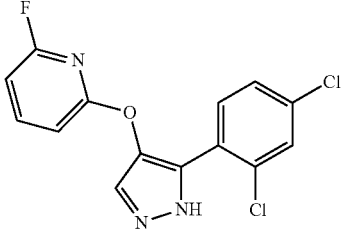<br />colorless amorphous solid | (Z and/or E)-1-(2,4-Dichlorophenyl)-3-(dimethylamino)-2-[(6-fluoro-2-pyridyl)oxy]prop-2-en-1-one (Intermediate A-21) | 324.4 |
| 22 | 2-[[3-(2,4-Dichlorophenyl)-1H-pyrazol-4-yl]oxy]-6-methylpyridine<br />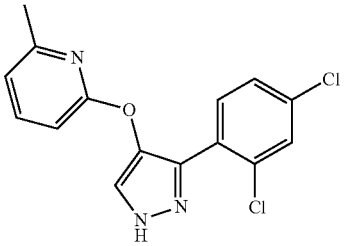<br />light brown amorphous solid | (Z and/or E)-1-(2,4-Dichlorophenyl)-3-(dimethylamino)-2-[(6-methyl-2-pyridyl)oxy]prop-2-en-1-one (Intermediate A-22) | 320.4 |

TABLE 2-continued

| Intermediate | Name Aspect | Reactant | MS (M + H⁺) |
|---|---|---|---|
| 23 | 5-(2-Chlorophenyl)-4-[4-(trifluoromethyl)phenoxy]-1H-pyrazole<br><br>colorless amorphous solid | (Z and/or E)-1-(2-Chlorophenyl)-3-(dimethylamino)-2-[4-(trifluoromethyl)phenoxy]prop-2-en-1-one (Intermediate A-23) | 339.0 |
| 24 | 4-(4-Chloro-2-fluorophenoxy)-5-(2-chlorophenyl)-1H-pyrazole<br><br>colorless amorphous solid | (Z and/or E)-2-(4-Chloro-2-fluoro-phenoxy)-1-(2-chlorophenyl)-3-(dimethylamino)prop-2-en-1-one (Intermediate A-24) | 323.0 |
| 25 | 4-[[5-(2-Chlorophenyl)-1H-pyrazol-4-yl]oxy]benzonitrile<br><br>light brown amorphous solid | 4-[(Z and/or E)-1-(2-Chlorobenzoyl)-2-(dimethylamino)vinyloxy]benzonitrile (Intermediate A-25) | 296.0 |
| 26 | 4-[[5-(2-Chloro-4-methylsulfanylphenyl)-1H-pyrazol-4-yl]oxy]benzonitrile<br><br>colorless oil | 4-[(Z and/or E)-1-(2-Chloro-4-methylsulfanyl-benzoyl)-2-(dimethylamino)vinyloxy]benzonitrile (Intermediate A-26) | 342.3 |
| 27 | 5-(4-Chloro-2-fluorophenyl)-4-[4-(trifluoromethyl)phenoxy]-1H-pyrazole<br><br>off white amorphous solid | (Z and/or E)-1-(4-Chloro-2-fluoro-phenyl)-3-(dimethylamino)-2-[4-(trifluoromethyl)phenoxy]prop-2-en-1-one (Intermediate A-27) | 357.5 |

TABLE 2-continued

| Intermediate | Name / Aspect | Reactant | MS (M + H⁺) |
|---|---|---|---|
| 28 | 4-[[5-(2-Chlorophenyl)-1H-pyrazol-4-yl]oxy]-3-fluorobenzonitrile 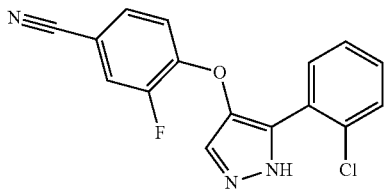 light brown amorphous solid | 4-[(Z and/or E)-1-(2-Chlorobenzoyl)-2-(dimethylamino)vinyloxy]-3-fluoro-benzonitrile (Intermediate A-28) | 314.1 |
| 29 | 4-[[5-(2,3-Difluorophenyl)-1H-pyrazol-4-yl]oxy]benzonitrile 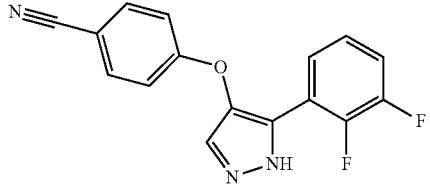 light yellow amorphous solid | 4-[(Z and/or E)-1-(2,3-Difluorobenzoyl)-2-(dimethylamino)vinyloxy]benzonitrile, (Intermediate A-29) | 298.1 |
| 30 | 4-[[5-(3-Chloro-2-fluorophenyl)-1H-pyrazol-4-yl]oxy]benzonitrile  yellow amorphous solid | 4-[(Z and/or E)-1-(3-Chloro-2-fluoro-benzoyl)-2-(dimethylamino)vinyloxy]benzonitrile, (Intermediate A-30) | 314.1 |
| 31 | 5-(3-Chloro-2-fluorophenyl)-4-(4-chlorophenoxy)-1H-pyrazole 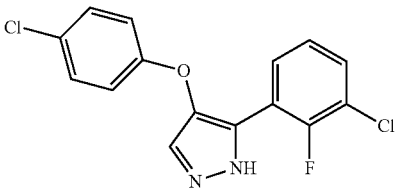 light yellow amorphous solid | (Z and/or E)-1-(3-Chloro-2-fluoro-phenyl)-2-(4-chlorophenoxy)-3-(dimethylamino)prop-2-en-1-one, (Intermediate A-31) | 323.0 |
| 32 | 4-[[5-(3-Chlorophenyl)-1H-pyrazol-4-yl]oxy]benzonitrile 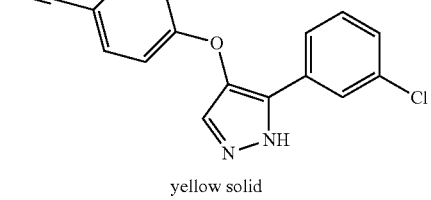 yellow solid | 4-[(Z and/or E)-1-(3-Chlorobenzoyl)-2-(dimethylamino)vinyloxy]benzonitrile, (Intermediate A-32) | 296.1 |

TABLE 2-continued

| Intermediate | Name / Aspect | Reactant | MS (M + H+) |
|---|---|---|---|
| 33 | Methyl 3-[4-(4-cyanophenoxy)-1H-pyrazol-3-yl]benzoate 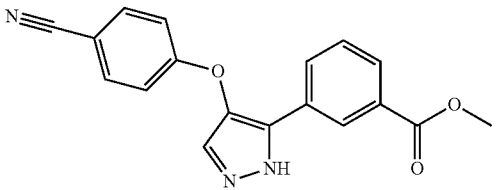 yellow solid | Methyl 3-[(Z and/or E)-2-(4-cyanophenoxy)-3-(dimethylamino)prop-2-enoyl]benzoate, (Intermediate A-33) | 320.2 |
| 34 | 5-(2-Chloro-3-fluorophenyl)-4-(4-chlorophenoxy)-1H-pyrazole 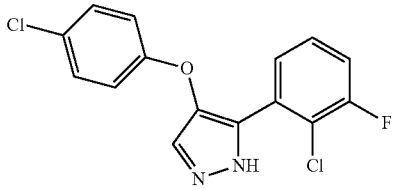 [SMILES: Fc1cccc(-c2[nH]ncc2Oc2ccc(Cl)cc2)c1F] light brown amorphous solid | (Z and/or E)-1-(2-Chloro-3-fluoro-phenyl)-2-(4-chlorophenoxy)-3-(dimethylamino)prop-2-en-1-one, (Intermediate A-34) | 323.1 |
| 35 | 4-[[5-(2-Chloro-3-fluorophenyl)-1H-pyrazol-4-yl]oxy]benzonitrile 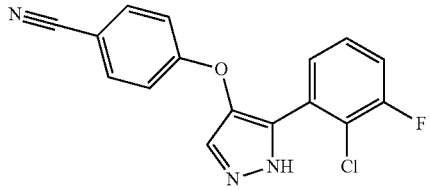 light brown amorphous solid | 4-[(Z and/or E)-1-(2-Chloro-3-fluoro-benzoyl)-(dimethylamino)vinyloxy]benzonitrile, (Intermediate A-35) | 314.1 |
| 36 | 4-[[5-(3-Phenylmethoxyphenyl)-1H-pyrazol-4-yl]oxy]benzonitrile 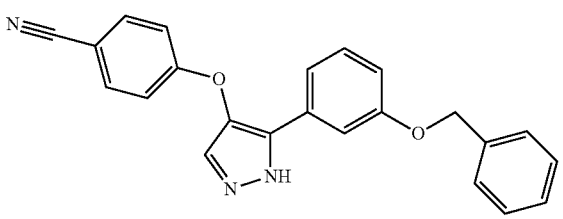 yellow oil | 4-[(Z and/or E)-1-(3-Benzyloxybenzoyl)-2-(dimethylamino)vinyloxy]benzonitrile, (Intermediate A-36) | 368.2 |
| 37 | 4-[[5-(2-Chloro-4-pyridyl)-1H-pyrazol-4-yl]oxy]benzonitrile 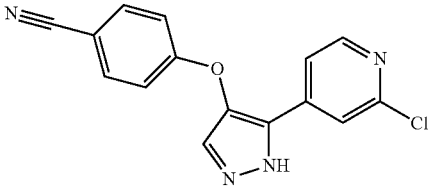 colorless solid | 4-[(Z and/or E)-1-(2-Chloropyridine-4-carbonyl)-2-(dimethylamino)vinyloxy]benzonitrile, (Intermediate A-37) | 297.1 |

TABLE 2-continued

| Intermediate | Name<br>Aspect | Reactant | MS<br>(M + H⁺) |
|---|---|---|---|
| 38 | Methyl 3-[4-(4-cyano-2-fluorophenoxy)-1H-pyrazol-3-yl]benzoate<br>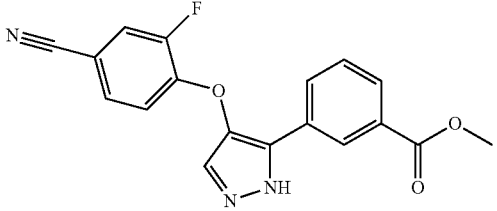<br>light brown amorphous solid | Methyl 3-[(Z and/or E)-2-(4-cyano-2-fluoro-phenoxy)-3-(dimethylamino)prop-2-enoyl]benzoate (Intermediate A-38) | 338.2 |
| 39 | Ethyl 2-[4-(4-cyanophenoxy)-1H-pyrazol-3-yl]benzoate<br>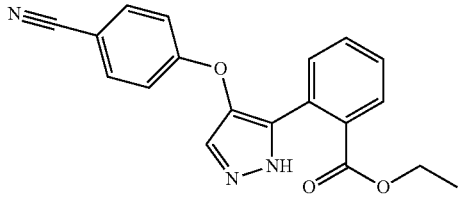<br>yellow amorphous solid | Ethyl 2-[(Z and/or E)-2-(4-cyanophenoxy)-3-(dimethylamino)prop-2-enoyl]benzoate (Intermediate A-39) | 334.2 |
| 40 | 2-[4-(4-Cyanophenoxy)-1H-pyrazol-3-yl]benzoic acid<br>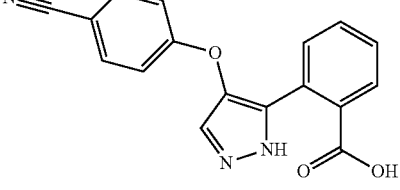<br>yellow amorphous solid | Ethyl 2-[(Z and/or E)-2-(4-cyanophenoxy)-3-(dimethylamino)prop-2-enoyl]benzoate (Intermediate A-39) | 306.2 |
| 41 | 4-[[5-(2-Phenylmethoxyphenyl)-1H-pyrazol-4-yl]oxy]benzonitrile<br>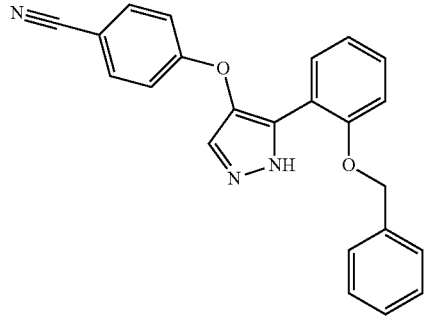<br>light yellow solid | 4-[(Z and/or E)-1-(2-Benzyloxybenzoyl)-2-(dimethylamino)vinyloxy]benzonitrile, (Intermediate A-40) | 368.1 |

Example 42

5-(2-Chloro-4-methylsulfonylphenyl)-4-(4-chlorophenoxy)-1H-pyrazole

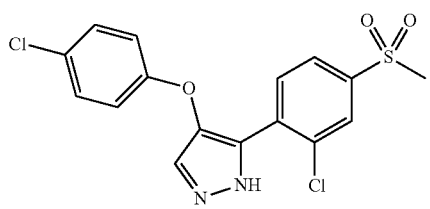 [SMILES: CS(=O)(=O)c1ccc(-c2[nH]ncc2Oc2ccc(Cl)cc2)c(Cl)c1]

Sodium bicarbonate (0.115 g, 1.37 mmol) in water (1 mL) was added at 0° C. (ice bath) to a solution of 5-(2-chloro-4-methyl sulfanylphenyl)-4-(4-chlorophenoxy)-1H-pyrazole (example 17) (0.06 g, 0.171 mmol) in acetone (1 mL). A solution of oxone (0.147 g, 0.239 mmol) in water (1.5 mL) was then added drop wise to the mixture while keeping the temperature below 5° C. and stirring was continued at this temperature for 2 h. The mixture was quenched at 0° C. by addition of a 40% sodium bisulfite solution (2 mL). The resulting suspension was diluted with EtOAc, acidified with a 25% aqueous HCl solution and the resulting aqueous layer was extracted with EtOAc (2×10 mL). The combined organics were washed with brine, dried over $Na_2SO_4$, filtered and evaporated. The residue was purified by silica gel flash chromatography eluting with a 0 to 100% EtOAc-heptane gradient to give the title compound (0.036 g, 55%) as a colorless amorphous solid. MS: 383.3 (M+H$^+$).

Example 43

4-[[5-(2-Chloro-4-methylsulfonylphenyl)-1H-pyrazol-4-yl]oxy]benzonitrile

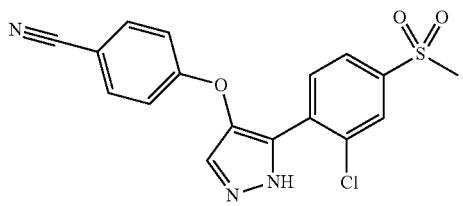 [SMILES: CS(=O)(=O)c1ccc(-c2[nH]ncc2Oc2ccc(C#N)cc2)c(Cl)c1]

In analogy to the procedure described in example 42, 4-[[5-(2-chloro-4-methylsulfanylphenyl)-1H-pyrazol-4-yl]oxy]benzonitrile (example 26) has been oxidized with oxone to give the title compound as a colorless amorphous solid. MS: 374.5 (M+H$^+$).

Example 44

4-[[3-[3-(4-Acetylpiperazine-1-carbonyl)phenyl]-1H-pyrazol-4-yl]oxy]benzonitrile

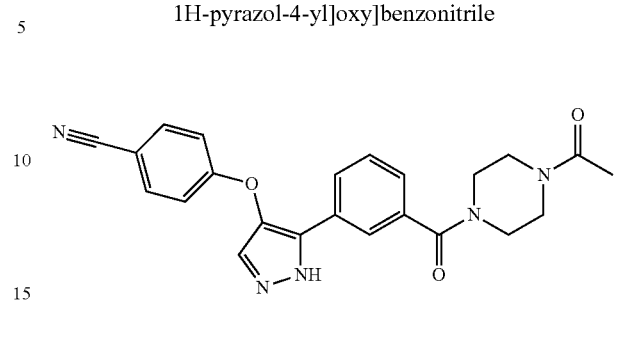

[A] (rac)-4-[3-[3-(4-Acetylpiperazine-1-carbonyl)phenyl]-1-tetrahydropyran-2-yl-pyrazol-4-yl]oxybenzonitrile

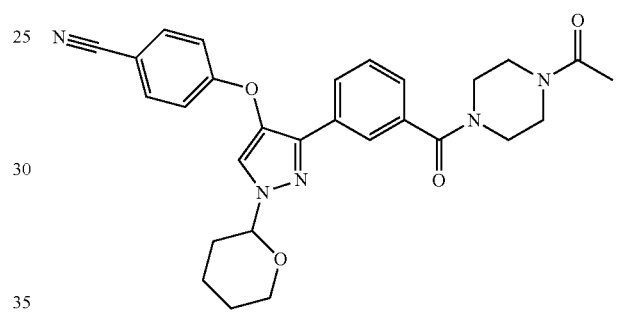

To a solution of (rac)-3-[4-(4-cyanophenoxy)-1-tetrahydropyran-2-yl-pyrazol-3-yl]benzoic acid (intermediate B-1) (0.035 g, 0.09 mmol) in DCM (2 mL) were added 1-(piperazin-1-yl)ethanone (0.011 g, 0.09 mmol), triethylamine (0.027 g, 0.27 mmol) and TBTU (0.035 g, 0.108 mmol). The reaction mixture was then stirred at room temperature for 1.5 h. The mixture was diluted with DCM, poured in water (10 mL) and the aqueous layer was extracted with DCM (2×15 mL). The combined organics were washed with brine, dried over $Na_2SO_4$, filtered and evaporated to dryness to give the title compound (0.048 g) as yellow oil, which was used in the next step with no further purification. MS: 500.3 (M+H$^+$).

[B] 4-[[3-[3-(4-Acetylpiperazine-1-carbonyl)phenyl]-1H-pyrazol-4-yl]oxy]benzonitrile

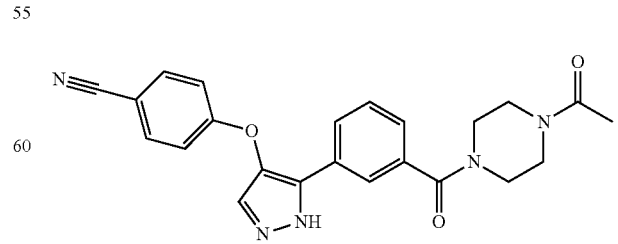

To a solution of (rac)-4-[3-[3-(4-acetylpiperazine-1-carbonyl)phenyl]-1-tetrahydropyran-2-yl-pyrazol-4-yl]oxy benzonitrile (0.048 g, 0.097 mmol) in MeOH (1 mL) was added a 4M HCl in dioxane (0.121 mL, 0.483 mmol) solution and the reaction mixture was stirred at room temperature for 3 h. The mixture was evaporated to dryness, the residue treated with a sat. NaHCO$_3$ solution (2 mL) and then extracted with EtOAc (2×10 mL). The organic layers were dried over Na$_2$SO$_4$, filtered and evaporated. The residue was purified by silica gel flash chromatography eluting with a 0 to 10% MeOH-DCM gradient to give the title compound (0.02 g, 47%) as a colorless solid. MS: 416.3 (M+H$^+$).

The following examples listed in Table 3 were prepared in analogy to the procedure described for the preparation of examples 44 by coupling (rac)-3-[4-(4-cyanophenoxy)-1-tetrahydropyran-2-yl-pyrazol-3-yl]benzoic acid (intermediate B-1) with the amines indicated and subsequent removal of the THP protecting group.

TABLE 3

| Example | Name Aspect | Reactant (amine) | MS (M + H$^+$) |
|---|---|---|---|
| 45 | 4-[[3-[3-(Morpholine-4-carbonyl)phenyl]-1H-pyrazol-4-yl]oxy]benzonitrile<br>light yellow oil | morpholine | 375.3 (M + H$^+$) |
| 46 | 4-[[3-[3-(4-Methylsulfonylpiperazine-1-carbonyl)phenyl]-1H-pyrazol-4-yl]oxy]benzonitrile<br>colorless solid | 4-methylsulfonyl-piperazine | 452.3 |
| 47 | 4-[[3-[3-[3-(Hydroxymethyl)azetidine-1-carbonyl]phenyl]-1H-pyrazol-4-yl]oxy]benzonitrile<br>yellow oil | 3-(hydroxymethyl)-azetidine | 375.3 (M + H$^+$) |

Example 48

4-[[3-(3-Hydroxyphenyl)-1H-pyrazol-4-yl]oxy]benzonitrile

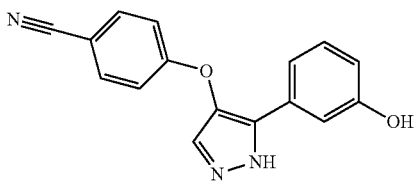 [SMILES: N#Cc1ccc(Oc2cn[nH]c2-c2cccc(O)c2)cc1]

[A] (rac)-4-[3-(3-Benzyloxyphenyl)-1-tetrahydropyran-2-yl-pyrazol-4-yl]oxybenzonitrile

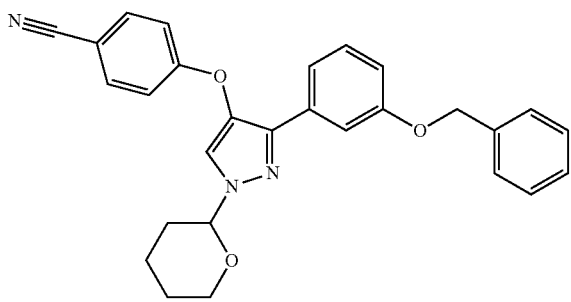 [SMILES: N#Cc1ccc(Oc2cn(C3CCCCO3)nc2-c2cccc(OCc3ccccc3)c2)cc1]

In analogy to the procedure described for the preparation of intermediate B-1 [A], 4-[[5-(3-phenylmethoxyphenyl)-1H-pyrazol-4-yl]oxy]benzonitrile (example 36), has been reacted with dihydro-pyran to give the title compound as light yellow solid. MS: 452.3 (M+H⁺).

[B] (rac)-4-[3-(3-Hydroxyphenyl)-1-tetrahydropyran-2-yl-pyrazol-4-yl]oxybenzonitrile

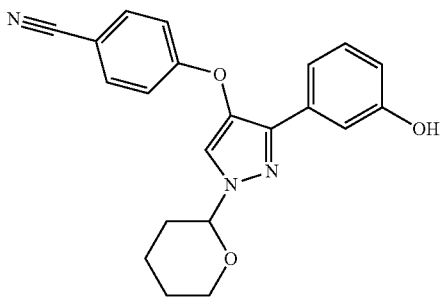 [SMILES: N#Cc1ccc(Oc2cn(C3CCCCO3)nc2-c2cccc(O)c2)cc1]

To a solution of (rac)-4-[3-(3-benzyloxyphenyl)-1-tetrahydropyran-2-yl-pyrazol-4-yl]oxybenzonitrile (0.127 g, 0.282 mmol) in MeOH (20 mL) purged with argon was added 10% Pd/C (0.03 g, 0.028 mmol). The reaction mixture was then stirred under H₂ atmosphere (balloon) for 2 h. The reaction mixture was filtered through a glass microfiber filter and the filtrate was evaporated to dryness. The residue was purified by silica gel flash chromatography eluting with 0% to 40% EtOAc-heptane gradient to give the title compound (0.092 g, 86%) of colorless amorphous solid. MS: 362.3 (M+H⁺).

[C] 4-[[3-(3-Hydroxyphenyl)-1H-pyrazol-4-yl]oxy]benzonitrile

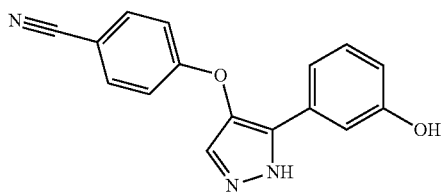 [SMILES: N#Cc1ccc(Oc2cn[nH]c2-c2cccc(O)c2)cc1]

In analogy to the procedure described for the preparation of example 44 [B], (rac)-4-[3-(3-hydroxyphenyl)-1-tetrahydropyran-2-yl-pyrazol-4-yl]oxybenzonitrile has been reacted with HCl (4M dioxane) in MeOH to give the title compound as colorless solid. MS: 278.2 (M+H⁺).

Example 49

4-[[3-[3-(Hydroxymethyl)phenyl]-1H-pyrazol-4-yl]oxy]benzonitrile

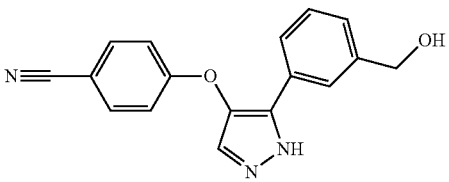 [SMILES: N#Cc1ccc(Oc2cn[nH]c2-c2cccc(CO)c2)cc1]

[A] (rac)-4-[3-[3-(Hydroxymethyl)phenyl]-1-tetrahydropyran-2-yl-pyrazol-4-yl]oxybenzonitrile

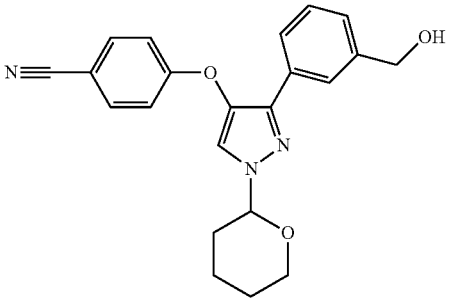 [SMILES: N#Cc1ccc(Oc2cn(C3CCCCO3)nc2-c2cccc(CO)c2)cc1]

To a solution of (rac)-3-[4-(4-cyanophenoxy)-1-tetrahydropyran-2-yl-pyrazol-3-yl]benzoic acid (intermediate B-1 [B]) (0.053 g, 0.123 mmol) in THF (1 mL) cooled to 0° C. (ice bath) was added a 1M solution of borane-THF complex in THF (0.247 mL, 0.247 mmol) drop wise and the reaction mixture was stirred at room temperature overnight. The mixture was quenched by slow addition of a 1M aqueous HCl solution (5 mL) and extracted with EtOAc (2×25 mL). The combined organics were washed with brine, dried over Na₂SO₄, filtered and evaporated to dryness. The residue was purified by silica gel flash chromatography eluting with a 0% to 10% MeOH-DCM gradient to give the title compound (0.048 g, 93%) as light yellow oil. MS: 376.3 (M+H⁺).

[B] 4-[[3-[3-(Hydroxymethyl)phenyl]-1H-pyrazol-4-yl]oxy]benzonitrile

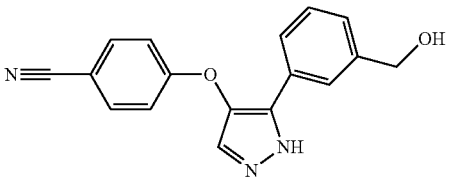 [SMILES: N#Cc1ccc(Oc2cn[nH]c2-c2cccc(CO)c2)cc1]

In analogy to the procedure described for the preparation of example 44 [B], (rac)-4-[3-[3-(hydroxymethyl)phenyl]-1-tetrahydropyran-2-yl-pyrazol-4-yl]oxybenzonitrile has been reacted with HCl (4M dioxane) in MeOH to give the title compound as yellow oil. MS: 292.2 (M+H⁺).

Example 50

4-[[3-[3-(Pyridin-2-ylmethoxy)phenyl]-1H-pyrazol-4-yl]oxy]benzonitrile

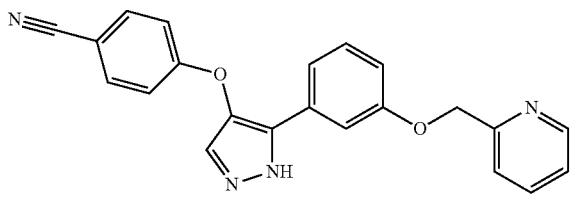 [SMILES: N#Cc1ccc(Oc2cn[nH]c2-c2cccc(OCc3ccccn3)c2)cc1]

[A] (rac)-4-[3-[3-(2-Pyridylmethoxy)phenyl]-1-tetrahydropyran-2-yl-pyrazol-4-yl]oxybenzonitrile

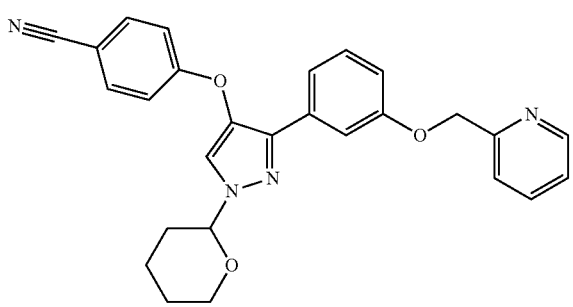 [SMILES: N#Cc1ccc(Oc2cn(C3CCCCO3)nc2-c2cccc(OCc3ccccn3)c2)cc1]

To a solution of (rac)-4-[3-(3-hydroxyphenyl)-1-tetrahydropyran-2-yl-pyrazol-4-yl]oxybenzonitrile (example 48 [B]) (0.033 g, 0.091 mmol) in DMF (1 mL) were added 2-(bromomethyl)pyridine hydrobromide (0.023 g, 0.091 mmol) and K₂CO₃ (0.038 g, 0.272 mmol). The reaction mixture was then stirred at room temperature for 8 h. The mixture was diluted with EtOAc, poured into a 1M aqueous HCl solution (5 mL) and the aqueous layer was extracted with EtOAc (2×15 mL). The combined organics were washed with brine, dried over Na₂SO₄, filtered and evaporated to dryness to give the title compound (0.047 g) as light yellow oil, which was used in the next step with no further purification. MS: 453.3 (M+H⁺).

[B] 4-[[3-[3-(Pyridin-2-ylmethoxy)phenyl]-1H-pyrazol-4-yl]oxy]benzonitrile

In analogy to the procedure described for the preparation of example 44 [B], (rac)-4-[3-[3-(2-pyridylmethoxy)phenyl]-1-tetrahydropyran-2-yl-pyrazol-4-yl]oxybenzonitrile has been reacted with HCl (4M dioxane) in MeOH to give the title compound as yellow solid. MS: 369.2 (M+H⁺).

The following examples listed in Table 4 were prepared in analogy to the procedure described for the preparation of example 50 by reacting (rac)-4-[3-(3-hydroxyphenyl)-1-tetrahydropyran-2-yl-pyrazol-4-yl]oxybenzonitrile (example 48 [B]) with a halo-methyl heterocyclic compounds and subsequently with acid.

TABLE 4

| Example | Name Aspect | Reactant | MS (M + H⁺) |
|---|---|---|---|
| 51 | 4-[[3-[3-(Pyridin-3-ylmethoxy)phenyl]-1H-pyrazol-4-yl]oxy]benzonitrile<br>brown solid | 3-(bromomethyl)pyridine | 369.2 |
| 52 | 4-[[3-[3-[(3-Methyl-1,2-oxazol-5-yl)methoxy]phenyl]-1H-pyrazol-4-yl]oxy]benzonitrile<br>yellow oil | 5-(bromomethyl)-3-methylisoxazole | 373.2 |

TABLE 4-continued

| Example | Name / Aspect | Reactant | MS (M + H⁺) |
|---|---|---|---|
| 53 | 4-[[3-[3-[(3-Methyltriazol-4-yl)methoxy]phenyl]-1H-pyrazol-4-yl]oxy]benzonitrile<br>brown oil | 5-(chloromethyl)-1-methyl-triazole | 373.2 |
| 54 | 4-[[3-[3-(Pyridin-4-ylmethoxy)phenyl]-1H-pyrazol-4-yl]oxy]benzonitrile<br>colorless solid | 4-(bromomethyl)pyridine hydrobromide | 369.2 |
| 55 | 4-[[3-[3-[(2-Chloropyridin-4-yl)methoxy]phenyl]-1H-pyrazol-4-yl]oxy]benzonitrile<br>orange amorphous solid | 2-chloro-4-(chloromethyl)pyridine | 403.2 |
| 56 | 4-[[3-[3-[(1-Methylpyrazol-4-yl)methoxy]phenyl]-1H-pyrazol-4-yl]oxy]benzonitrile<br>colorless amorphous solid | 4-(chloromethyl)-1-methyl-pyrazole | 372.2 |

Example 57

(rac)-4-[[3-(3-Pyrrolidin-3-yloxyphenyl)-1H-pyrazol-4-yl]oxy]benzonitrile

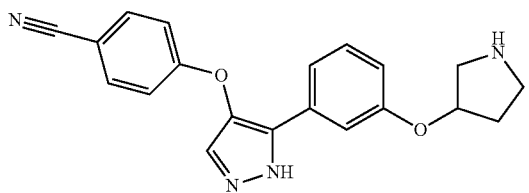 [SMILES: N#Cc1ccc(Oc2cn[nH]c2-c2cccc(OC3CCNC3)c2)cc1]

[A] (rac, diast)-tert-Butyl 3-[3-[4-(4-cyanophenoxy)-1-tetrahydropyran-2-yl-pyrazol-3-yl]phenoxy]pyrrolidine-1-carboxylate

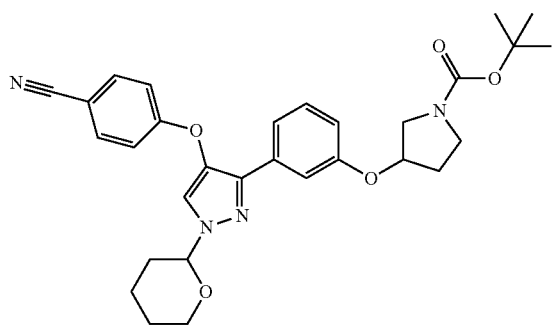 [SMILES: CC(C)(C)OC(=O)N1CCC(Oc2cccc(-c3nn(C4CCCCO4)cc3Oc3ccc(C#N)cc3)c2)C1]

To a mixture of (rac)-4-[3-(3-hydroxyphenyl)-1-tetrahydropyran-2-yl-pyrazol-4-yl]oxybenzonitrile (example 48 [B]) (0.1 g, 0.277 mmol) and tert-butyl 3-hydroxypyrrolidine-1-carboxylate (0.062 g, 0.332 mmol) in THF (2 mL) cooled to 0° C. (ice bath) were added (E)-diazene-1,2-diylbis(piperidin-1-ylmethanone) (0.14 g, 0.553 mmol) followed by tri-n-butylphosphine (0.073 g, 0.089 mmol) drop wise. The reaction mixture was then stirred at room temperature overnight. The mixture was diluted with EtOAc, poured into water (5 mL) and the aqueous layer was extracted with EtOAc (2×20 mL). The combined organics were washed with brine, dried over Na$_2$SO$_4$, filtered and evaporated to dryness. The crude material was triturated with Et$_2$O, the solid filtered off and the mother liquors were evaporated. The residue was purified by silica gel flash chromatography eluting with a 0% to 100% EtOAc-heptane gradient to give the title compound (0.043 g, 28%) as yellow oil (two racemic diastereomers). MS: 529.5 (M−H⁺).

[B] (rac)-4-[[3-(3-Pyrrolidin-3-yloxyphenyl)-1H-pyrazol-4-yl]oxy]benzonitrile

In analogy to the procedure described for the preparation of example 44 [B], (rac, diast)-tert-butyl 3-[3-[4-(4-cyanophenoxy)-1-tetrahydropyran-2-yl-pyrazol-3-yl]phenoxy]pyrrolidine-1-carboxylate, has been reacted with HCl (4M dioxane) in MeOH to give the title compound as colorless oil. MS: 347.2 (M+H⁺).

Example 58

(rac)-4-[[3-[3-(1-Acetylpyrrolidin-3-yl)oxyphenyl]-1H-pyrazol-4-yl]oxy]benzonitrile

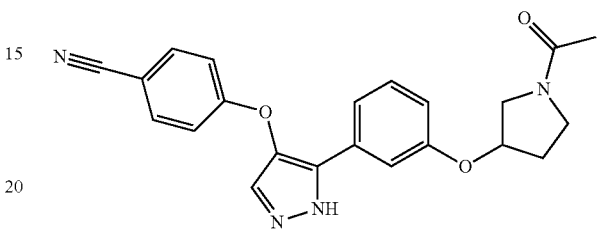

To a solution of 4-[[3-(3-pyrrolidin-3-yloxyphenyl)-1H-pyrazol-4-yl]oxy]benzonitrile (example 57) (0.022 g, 0.057 mmol) in DCM (2 mL) were added triethylamine (0.017 g, 0.172 mmol), acetic acid (0.003 g, 0.057 mmol) and TBTU (0.022 g, 0.069 mmol). The reaction mixture was stirred at room temperature for 1 h. The mixture was then evaporated to dryness, the residue dissolved in water (5 mL) and extracted with EtOAc (2×10 mL). The residue was purified by prep-HPLC (Gemini NX 3u column, gradient 1% aq. formic acid/acetonitrile) to give the title compound (0.012 g, 43%) as a colorless amorphous solid. MS: 389.3 (M+H⁺).

Example 59

4-[[5-(3-Butoxyphenyl)-1H-pyrazol-4-yl]oxy]benzonitrile

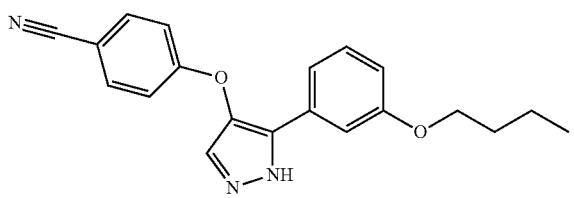 [SMILES: CCCCOc1cccc(-c2[nH]ncc2Oc2ccc(C#N)cc2)c1]

[A] (rac)-4-[3-(3-Butoxyphenyl)-1-tetrahydropyran-2-yl-pyrazol-4-yl]oxybenzonitrile

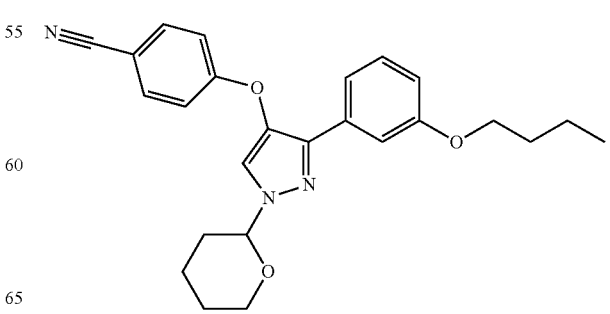

In analogy to the procedure described in example 57 [A], (rac)-4-[3-(3-hydroxyphenyl)-1-tetrahydropyran-2-yl-pyrazol-4-yl]oxybenzonitrile (example 48 [B]) and tert-butyl 3-hydroxyazetidine-1-carboxylate was reacted with (E)-diazene-1,2-diylbis(piperidin-1-ylmethanone) and tri-n-butylphosphine in THF to give the title compound as colorless oil. MS: 418.4 (M+H+).

[B] 4-[[5-(3-Butoxyphenyl)-1H-pyrazol-4-yl]oxy] benzonitrile

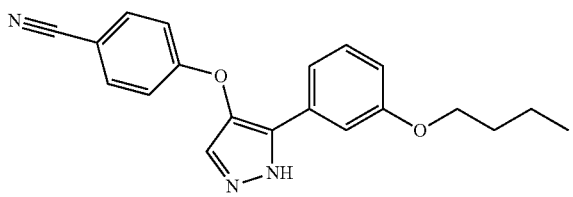 [SMILES: CCCCOc1cccc(-c2[nH]ncc2Oc2ccc(C#N)cc2)c1]

In analogy to the procedure described for the preparation of example 44 [B], (rac)-4-[3-(3-butoxyphenyl)-1-tetrahydropyran-2-yl-pyrazol-4-yl]oxybenzonitrile, has been reacted with HCl (4M dioxane) in MeOH to give the title compound as colorless oil. MS: 334.2 (M+H+).

Example 60

4-[[3-[2-(2-Methoxyphenyl)ethyl]-1H-pyrazol-4-yl] oxy]benzonitrile

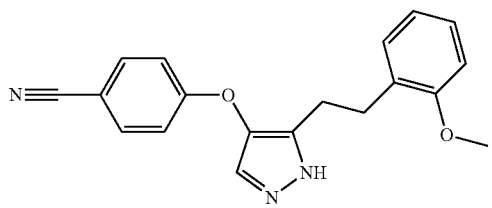 [SMILES: COc1ccccc1CCc1[nH]ncc1Oc1ccc(C#N)cc1]

[A] (rac)-4-[3-[2-(2-Methoxyphenyl)ethynyl]-1-tetrahydropyran-2-yl-pyrazol-4-yl]oxybenzonitrile

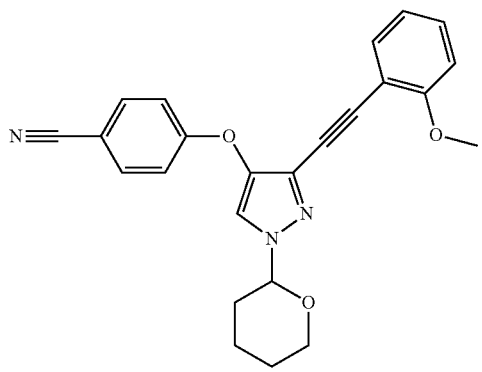 [SMILES: COc1ccccc1C#Cc1nn(C2CCCCO2)cc1Oc1ccc(C#N)cc1]

In a sealed tube, (rac)-[4-(4-cyanophenoxy)-1-tetrahydropyran-2-yl-pyrazol-3-yl] trifluoromethanesulfonate (intermediate B-2) (0.075 g, 0.180 mmol), 1-ethynyl-2-methoxybenzene (0.028 g, 0.216 mmol) and TEA (0.091 g, 0.899 mmol) were mixed in DMF (1.5 mL). Then, bis(triphenylphosphine)palladium (II) chloride (0.013 g, 0.018 mmol) and copper (I) iodide (0.007 g, 0.036 mmol) were added and the reaction mixture was heated to 80° C. for 2 h. The mixture was diluted with EtOAc, poured into water (5 mL) and the aqueous layer was extracted with EtOAc (2×10 mL). The combined organics were washed with brine, dried over Na2SO4, filtered and evaporated. The residue was purified by silica gel flash chromatography, eluting with a 0 to 40% EtOAc-heptane gradient to give the title compound (0.01 g, 14%) as colorless oil. MS: 316.2 (M-THP+H+).

[B] (rac)-4-[3-[2-(2-Methoxyphenyl)ethyl]-1-tetrahydropyran-2-yl-pyrazol-4-yl]oxybenzonitrile

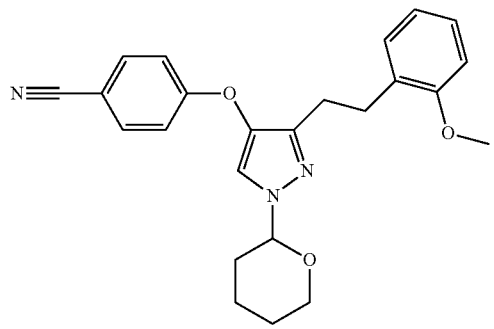 [SMILES: COc1ccccc1CCc1nn(C2CCCCO2)cc1Oc1ccc(C#N)cc1]

To a solution of (rac)-4-[3-[2-(2-methoxyphenyl)ethynyl]-1-tetrahydropyran-2-yl-pyrazol-4-yl]oxybenzonitrile (0.01 g, 0.025 mmol) in EtOH (2 mL) purged with Argon was added 10% Pd/C (0.003 g, 0.0025 mmol). The reaction mixture was then stirred under H2 (balloon) for 5 h. The mixture was diluted with MeOH, filtered over a glass microfiber filter and the filtrate was evaporated to dryness to give the title compound (0.007 g, 69%) as yellow oil, which was used in the next step with no further purification. MS: 404.3 (M+H+).

[C] 4-[[3-[2-(2-Methoxyphenyl)ethyl]-1H-pyrazol-4-yl]oxy]benzonitrile

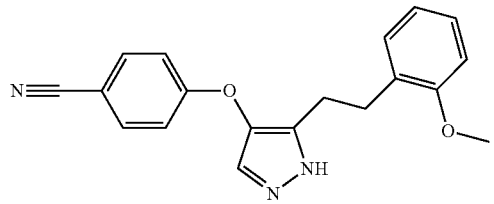 [SMILES: COc1ccccc1CCc1[nH]ncc1Oc1ccc(C#N)cc1]

In analogy to the procedure described for the preparation of example 44 [B], (rac) 4-[3-[2-(2-methoxyphenyl)ethyl]-1-tetrahydropyran-2-yl-pyrazol-4-yl]oxybenzonitrile has been reacted with HCl (4M dioxane) in MeOH to give the title compound yellow oil. MS: 320.2 (M+H+).

Example 61

(rac)-4-[[5-(3-Piperidyl)-1H-pyrazol-4-yl]oxy]benzonitrile

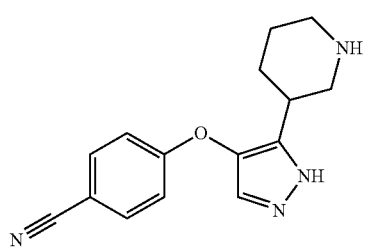 [SMILES: N#Cc1ccc(Oc2cn[nH]c2C2CCCNC2)cc1]

[A] (rac)-tert-Butyl 5-[4-(4-cyanophenoxy)-1-tetrahydropyran-2-yl-pyrazol-3-yl]-3,6-dihydro-2H-pyridine-1-carboxylate

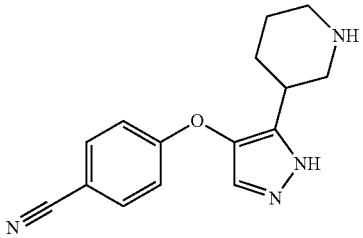

In a microwave vial, (rac)-[4-(4-cyanophenoxy)-1-tetrahydropyran-2-yl-pyrazol-3-yl] trifluoromethanesulfonate (intermediate B-2) (0.125 g, 0.3 mmol) and tert-butyl 3-(4,4,5,5-tetramethyl-1,3,2-dioxaborolan-2-yl)-5,6-dihydropyridine-1(2H)-carboxylate (0.102 g, 0.329 mmol) were mixed in DMF (2 mL). The vial was purged with argon, then bis(triphenylphosphine)palladium (II) chloride (0.021 g, 0.03 mmol) and a 1M aqueous $Na_2CO_3$ solution (0.749 mL, 0.749 mmol) were added and the reaction mixture was then heated to 120° C. for 15 min under microwave irradiation. The mixture was diluted with EtOAc, poured into water (10 mL) and the aqueous layer was extracted with EtOAc (2×15 mL). The combined organics were washed with brine, dried over $Na_2SO_4$, filtered and evaporated. The residue was purified by silica gel flash chromatography eluting with a 0 to 70% EtOAc-heptane gradient to give the title compound (0.095 g, 70%) as light yellow oil. MS: 451.4 (M+H$^+$).

[B] (rac, diast)-tert-Butyl 3-[4-(4-cyanophenoxy)-1-tetrahydropyran-2-yl-pyrazol-3-yl]piperidine-1-carboxylate

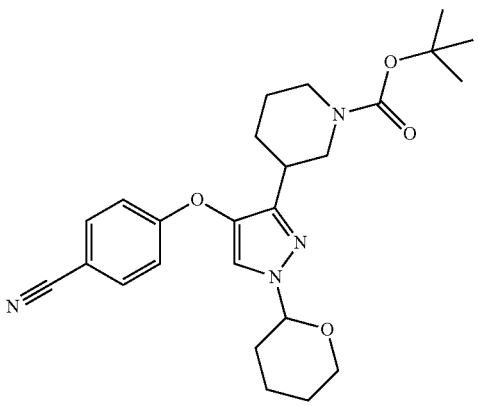 [SMILES: CC(C)(C)OC(=O)N1CCCC(c2nn(C3CCCCO3)cc2Oc2ccc(C#N)cc2)C1]

In analogy to the procedures described for example 60 [B], (rac)-tert-butyl 5-[4-(4-cyanophenoxy)-1-tetrahydropyran-2-yl-pyrazol-3-yl]-3,6-dihydro-2H-pyridine-1-carboxylate has been hydrogenated to give the title compound as colorless oil. MS: 453.4 (M+H$^+$).

[C] (rac)-4-[[5-(3-Piperidyl)-1H-pyrazol-4-yl]oxy]benzonitrile

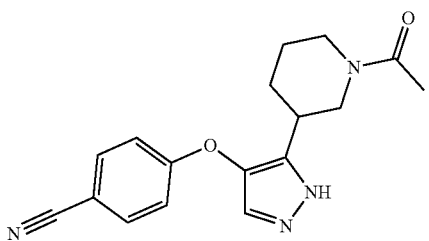 [SMILES: CC(=O)N1CCCC(c2[nH]ncc2Oc2ccc(C#N)cc2)C1]

In analogy to the procedure described for the preparation of example 44 [B], (rac, diast)-tert-butyl 3-[4-(4-cyanophenoxy)-1-tetrahydropyran-2-yl-pyrazol-3-yl]piperidine-1-carboxylate has been reacted with HCl (4M dioxane) in MeOH to give the title compound as light yellow oil. MS: 269.2 (M+H$^+$).

Example 62

(rac)-4-[[3-(1-Acetylpiperidin-3-yl)-1H-pyrazol-4-yl]oxy]benzonitrile

[A] (rac)-4-[1-Acetyl-3-(1-acetyl-3-piperidyl)pyrazol-4-yl]oxybenzonitrile

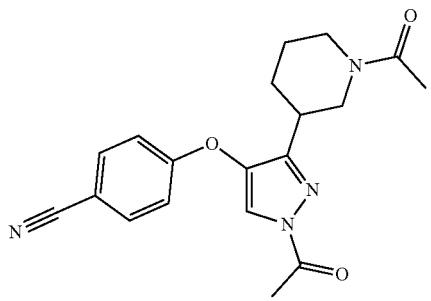 [SMILES: CC(=O)N1CCCC(c2nn(C(C)=O)cc2Oc2ccc(C#N)cc2)C1]

To a solution of (rac)-4-[[5-(3-piperidyl)-1H-pyrazol-4-yl]oxy]benzonitrile (example 61) (0.04 g, 0.149 mmol) in DMF (0.6 mL) cooled to 0° C. (ice bath) was added TEA (0.07 g, 0.745 mmol) followed by acetyl chloride (0.035 g, 0.447 mmol) and the reaction mixture was stirred at room temperature for 1 h. The mixture was diluted in EtOAc, poured into H$_2$O (2.5 mL) and the aqueous layer was extracted with EtOAc (2×10 mL). The combined organics were washed with brine, dried over Na$_2$SO$_4$, filtered and evaporated to give the title compound (0.052 g) as yellow oil, which was used in the next step with no further purification. MS: 353.2 (M+H$^+$).

[B] (rac)-4-[[3-(1-Acetylpiperidin-3-yl)-1H-pyrazol-4-yl]oxy]benzonitrile

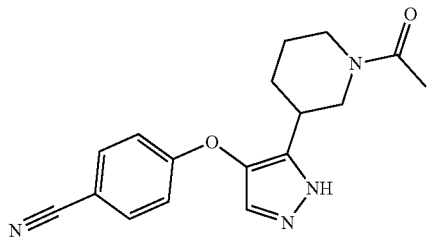 [SMILES: CC(=O)N1CCCC(c2[nH]ncc2Oc2ccc(C#N)cc2)C1]

To a solution of (rac)-4-[1-acetyl-3-(1-acetyl-3-piperidyl) pyrazol-4-yl]oxybenzonitrile (0.05 g, 0.142 mmol) in dioxane (0.5 mL) was added a 4M aqueous NaOH solution (0.177 mL, 0.709 mmol) and the reaction mixture was stirred at room temperature for 1 h. The mixture was evaporated to dryness and the residue purified by silica gel flash chromatography eluting with a 0 to 10% MeOH-DCM gradient to give the title compound (0.006 g, 16%) as colorless solid. MS: 311.2 (M+H$^+$).

Example 63

(rac)-4-[[3-[1-(1-Methylpyrazole-4-carbonyl)piperidin-3-yl]-1H-pyrazol-4-yl]oxy]benzonitrile

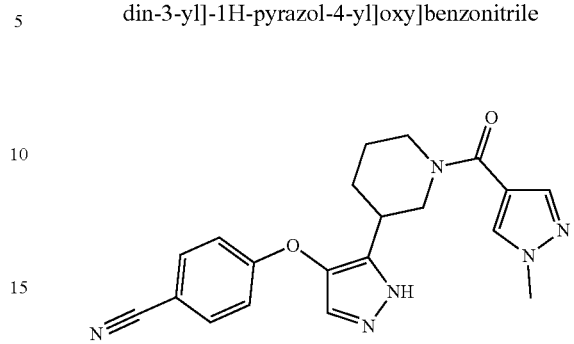

To a solution of (rac)-4-[[5-(3-piperidyl)-1H-pyrazol-4-yl]oxy]benzonitrile (example 61) (0.04 g, 0.149 mmol) in DMF (0.6 mL) were added 1-methyl-1H-pyrazole-4-carboxylic acid (0.021 g, 0.164 mmol) and TEA (0.06 g, 0.596 mmol) followed by HATU (0.068 g, 0.179 mmol) and the reaction mixture was stirred at room temperature for 5 h. The mixture was diluted with EtOAc, poured into water (5 mL) and the aqueous layer was extracted with EtOAc (2×15 mL). The combined organics were washed with brine, dried over Na$_2$SO$_4$, filtered and evaporated. The residue was purified by silica gel flash chromatography eluting with a 0 to 10% MeOH-DCM gradient to give the title compound (0.015 g, 27%) as a colorless amorphous solid. MS: 377.3 (M+H$^+$).

Example 64

(rac)-4-[[3-[1-(Pyridine-3-carbonyl)piperidin-3-yl]-1H-pyrazol-4-yl]oxy]benzonitrile

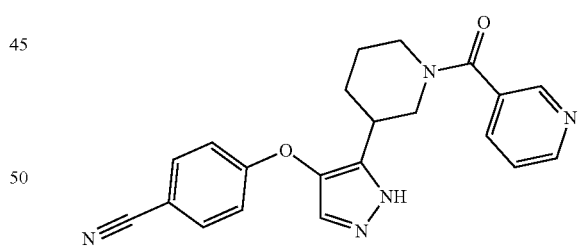

To a solution of (rac)-4-[[5-(3-piperidyl)-1H-pyrazol-4-yl]oxy]benzonitrile (example 61) (0.029 g, 0.087 mmol) in DMF (0.5 mL) were added nicotinic acid (0.011 g, 0.087 mmol) and TEA (0.026 g, 0.262 mmol) followed by TBTU (0.034 g, 0.105 mmol) and the reaction mixture was stirred at room temperature for 2 h. The mixture was diluted with EtOAc, poured into water (5 mL) and the aqueous layer was extracted with EtOAc (2×15 mL). The combined organics were washed with brine, dried over Na$_2$SO$_4$, filtered and evaporated. The residue was purified by prep-HPLC (Gemini NX 3u column, gradient 1% aq. formic acid/acetonitrile) to give the title compound (0.004 g, 10%) as orange oil. MS: 374.3 (M+H$^+$).

Example 65

(rac)-4-[[3-[1-(Pyridine-2-carbonyl)piperidin-3-yl]-1H-pyrazol-4-yl]oxy]benzonitrile

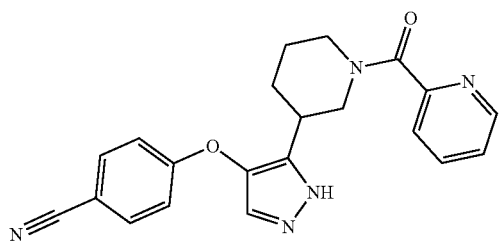 [SMILES: N#Cc1ccc(Oc2cn[nH]c2C2CCCN(C(=O)c3ccccn3)C2)cc1]

In analogy to the procedure described for the preparation of example 64, (rac)-4-[[5-(3-piperidyl)-1H-pyrazol-4-yl]oxy]benzonitrile (example 61) has been reacted with pyridine-2-carboxylic acid and TBTU to give the title compound as colorless solid. MS: 374.2 (M+H$^+$).

Example 66

4-[[3-(2-Methyl-1,3-thiazol-5-yl)-1H-pyrazol-4-yl]oxy]benzonitrile

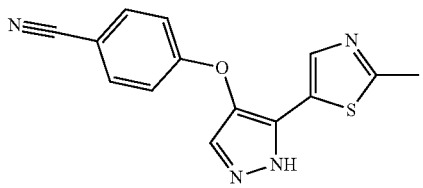 [SMILES: Cc1ncc(-c2[nH]ncc2Oc2ccc(C#N)cc2)s1]

In analogy to the procedures described in example 61 [A] and example 44 [B], (rac)-[4-(4-cyanophenoxy)-1-tetrahydropyran-2-yl-pyrazol-3-yl] trifluoromethanesulfonate (intermediate B-2) has been reacted with 2-methyl-5-(4,4,5,5-tetramethyl-1,3,2-dioxaborolan-2-yl)thiazole and subsequently with HCl (4M dioxane) in MeOH to give the title compound as light yellow oil. MS: 283.1 (M+H$^+$).

Example 67

4-[[3-(1-Methylpyrazol-4-yl)-1H-pyrazol-4-yl]oxy]benzonitrile

In analogy to the procedures described in example 61 [A] and example 44 [B], (rac)-[4-(4-cyanophenoxy)-1-tetrahydropyran-2-yl-pyrazol-3-yl] trifluoromethanesulfonate (intermediate B-2) has been reacted with 1-methyl-4-(4,4,5,5-tetramethyl-1,3,2-dioxaborolan-2-yl)-1H-pyrazole and subsequently with HCl (4M dioxane) in MeOH to give the title compound as colorless oil. MS: 266.2 (M+H$^+$).

Example 68

4-[[5-(1-Benzylpyrazol-4-yl)-1H-pyrazol-4-yl]oxy]benzonitrile

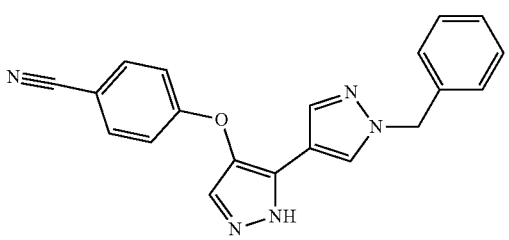 [SMILES: N#Cc1ccc(Oc2cn[nH]c2-c2cnn(Cc3ccccc3)c2)cc1]

In analogy to the procedures described in example 61 [A] and example 44 [B], (rac)-[4-(4-cyanophenoxy)-1-tetrahydropyran-2-yl-pyrazol-3-yl] trifluoromethanesulfonate (intermediate B-2) has been reacted with 1-benzyl-4-(4,4,5,5-tetramethyl-1,3,2-dioxaborolan-2-yl)-1H-pyrazole and subsequently with HCl (4M dioxane) in MeOH to give the title compound as colorless oil. MS: 342.1 (M+H$^+$).

Example 69

4-[[3-[3-[(6-Fluoropyridin-2-yl)oxymethyl]phenyl]-1H-pyrazol-4-yl]oxy]benzonitrile

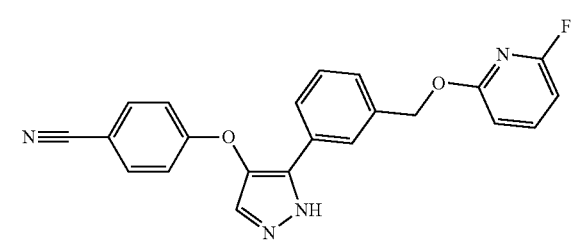 [SMILES: N#Cc1ccc(Oc2cn[nH]c2-c2cccc(COc3cccc(F)n3)c2)cc1]

[A] (rac)-4-[3-[3-(Chloromethyl)phenyl]-1-tetrahydropyran-2-yl-pyrazol-4-yl]oxybenzonitrile

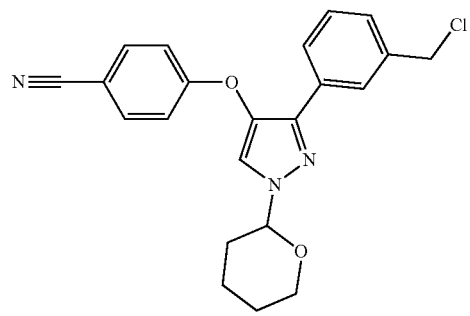 [SMILES: N#Cc1ccc(Oc2cn(C3CCCCO3)nc2-c2cccc(CCl)c2)cc1]

To a solution of (rac)-4-[3-[3-(hydroxymethyl)phenyl]-1-tetrahydropyran-2-yl-pyrazol-4-yl]oxybenzonitrile (example 49 [A]) (0.13 g, 0.329 mmol) in DMF (2 mL) cooled to 0° C. were added 2,4,6-trimethylpyridine (0.064 g, 0.527 mmol), methanesulfonyl chloride (0.64 g, 0.56 mmol) and lithium chloride (0.028 g, 0.658 mmol). The reaction mixture was stirred at 0° C. for 10 min and then at room temperature for 1 h. The mixture was diluted with EtOAc, poured into a sat. NaHCO₃ solution (5 mL) and the aqueous layer extracted with EtOAc (2×10 mL). The combined organics were washed with brine, dried over Na₂SO₄, filtered and evaporated to give the title compound (0.144 g, 100%) as colorless oil. The crude product was used in the next step with no further purification. MS: 394.2 (M+H⁺).

[B] (rac)-4-[3-[3-[(6-Fluoro-2-pyridyl)oxymethyl]phenyl]-1-tetrahydropyran-2-yl-pyrazol-4-yl]oxy-benzonitrile

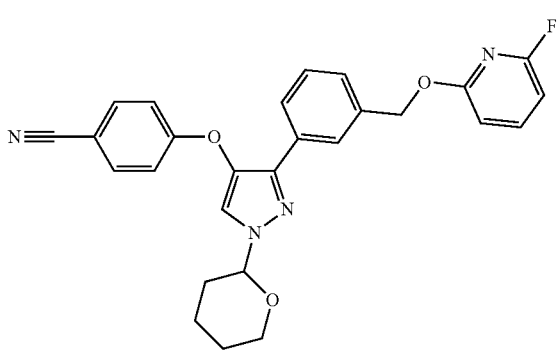 [SMILES: N#Cc1ccc(Oc2cn(C3CCCCO3)nc2-c2cccc(COc3cccc(F)n3)c2)cc1]

To a solution of (rac)-4-[3-[3-(chloromethyl)phenyl]-1-tetrahydropyran-2-yl-pyrazol-4-yl]oxybenzonitrile (0.038 g, 0.088 mmol) in DMF (1 mL) were added 6-fluoropyridin-2-ol (0.01 g, 0.088 mmol) and K₂CO₃ (30.4 mg, 0.22 mmol).

The reaction mixture was heated to 60° C. overnight. The mixture was diluted EtOAc, poured into a 1M HCl solution and the aqueous layer extracted with EtOAc (2×10 mL). The combined organics were washed with brine, dried over Na₂SO₄, filtered and evaporated. The residue was purified by silica gel flash chromatography, eluting with 0% to 40% EtOAc-heptane gradient to give the title compound (0.047 g, 85%) as colorless oil. MS: 471.2 (M+H⁺).

[C] 4-[[3-[3-[(6-Fluoropyridin-2-yl)oxymethyl]phenyl]-1H-pyrazol-4-yl]oxy]benzonitrile

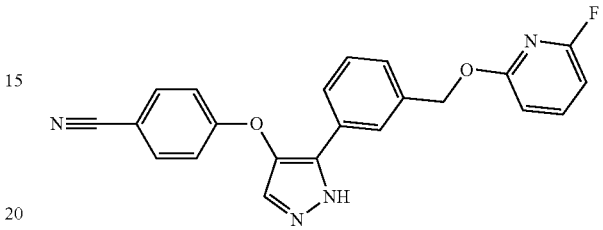

In analogy to the procedure described for the preparation of example 44 [B], (rac)-4-[3-[3-[(6-fluoro-2-pyridyl)oxymethyl]phenyl]-1-tetrahydropyran-2-yl-pyrazol-4-yl]oxybenzonitrile has been reacted with HCl (4M dioxane) in MeOH to give the title compound as colorless amorphous solid. MS: 387.2 (M+H⁺).

The following examples listed in Table 5 were prepared in analogy to the procedures described for the preparation of examples 69 [B] and [C] by reacting (rac)-4-[3-[3-(chloromethyl)phenyl]-1-tetrahydropyran-2-yl-pyrazol-4-yl]oxybenzonitrile with the heterocycles indicated and subsequent treatment with acid.

TABLE 5

| Example | Name / Aspect | Reactant | MS (M + H⁺) |
|---|---|---|---|
| 70 | 4-[[3-[3-(Pyridin-3-yloxymethyl)phenyl]-1H-pyrazol-4-yl]oxy]benzonitrile colorless oil | pyridin-3-ol | 369.2 |
| 71 | 1-[[3-[4-(4-Cyanophenoxy)-1H-pyrazol-3-yl]phenyl]methyl]pyridin-1-ium-3-olate brown oil | pyridin-3-ol | 369.2 |

TABLE 5-continued

| Example | Name Aspect | Reactant | MS (M + H+) |
|---|---|---|---|
| 72 | 4-[[3-[3-[(4-Oxopyridin-1-yl)methyl]phenyl]-1H-pyrazol-4-yl]oxy]benzonitrile | pyridin-4-ol | 369.2 |

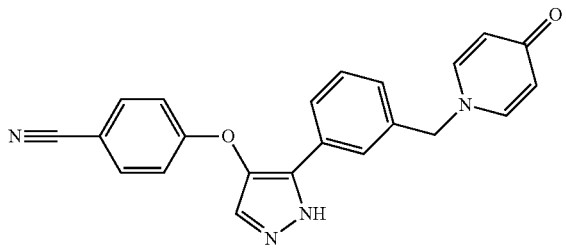

colorless oil

| 73 | 4-[[3-[3-[(6-Chloropyridin-2-yl)oxymethyl]phenyl]-1H-pyrazol-4-yl]oxy]benzonitrile | 6-chloropyridin-2-ol | 403.1 |

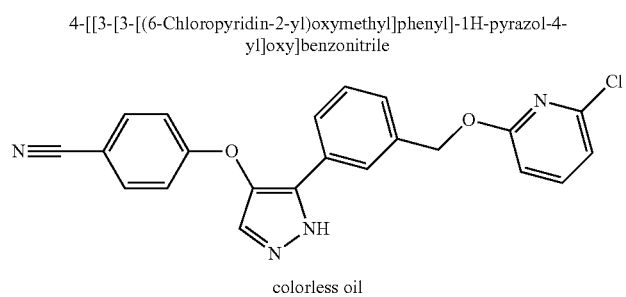 [SMILES: N#Cc1ccc(Oc2cn[nH]c2-c2cccc(COc3cccc(Cl)n3)c2)cc1]

colorless oil

Example 74

4-[[3-[3-[[3-Fluoro-3-(hydroxymethyl)azetidin-1-yl]methyl]phenyl]-1H-pyrazol-4-yl]oxy]benzonitrile

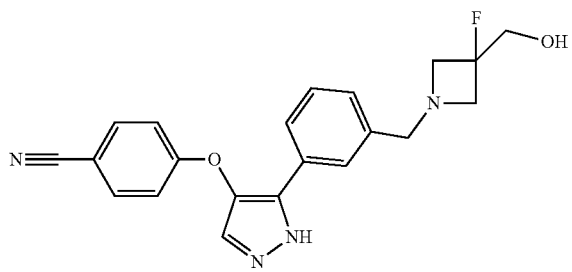 [SMILES: N#Cc1ccc(Oc2cn[nH]c2-c2cccc(CN3CC(F)(CO)C3)c2)cc1]

[A] (rac)-4-[3-(3-Formylphenyl)-1-tetrahydropyran-2-yl-pyrazol-4-yl]oxybenzonitrile

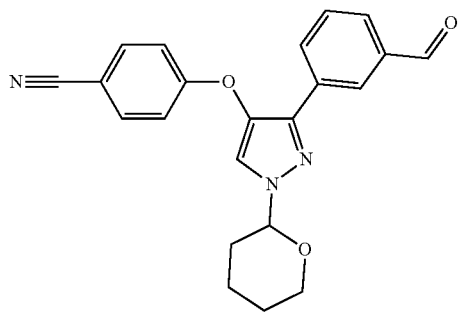 [SMILES: N#Cc1ccc(Oc2cn(C3CCCCO3)nc2-c2cccc(C=O)c2)cc1]

To a solution of (rac)-4-[3-[3-(hydroxymethyl)phenyl]-1-tetrahydropyran-2-yl-pyrazol-4-yl]oxybenzonitrile (example 49 [A]) (0.159 g, 0.403 mmol) in dioxane (5 mL) was added manganese dioxide (0.421 g, 4.84 mmol) and the reaction mixture was heated to 60° C. for 3 h. The mixture was diluted with EtOAc, filtered through Dicalite and washed with EtOAc. The solvent was evaporated and the residue purified by silica gel flash chromatography, eluting with a 0% to 20% EtOAc-heptane gradient to give the title compound (0.115 g, 73%) as colorless oil. MS: 290.1 (M+H-THP+).

[B] (rac)-4-[3-[3-[[3-Fluoro-3-(hydroxymethyl)azetidin-1-yl]methyl]phenyl]-1-tetrahydropyran-2-yl-pyrazol-4-yl]oxybenzonitrile

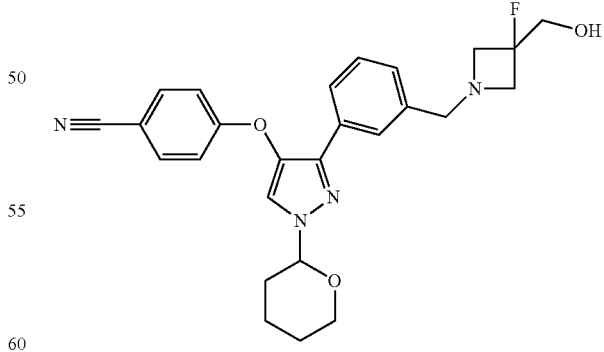

To a solution of (rac)-4-[3-(3-formylphenyl)-1-tetrahydropyran-2-yl-pyrazol-4-yl]oxybenzonitrile (0.065 g, 0.164 mmol) in DCE (1 mL) were added 3-fluoroazetidin-3-yl) methanol (0.017 g, 0.164 mmol) and acetic acid (0.012 mg, 0.197 mmol). The reaction mixture was stirred at room temperature for 30 min, then sodium triacetoxyborohydride (0.104 g, 0.493 mmol) was added and stirring was continued for 2 h. The mixture was diluted with EtOAc, poured into water (5 mL) and the aqueous layer extracted with EtOAc (2×10 mL). Combined organics were washed with brine, dried over $Na_2SO_4$, filtered and evaporated. The residue was purified by silica gel flash chromatography, eluting with a 0% to 15% MeOH-DCM gradient to give the title compound (0.019 g, 20%) as colorless oil. MS: 463.3 (M+H⁺).

[C] 4-[[3-[3-[[3-Fluoro-3-(hydroxymethyl)azetidin-1-yl]methyl]phenyl]-1H-pyrazol-4-yl]oxy]benzonitrile

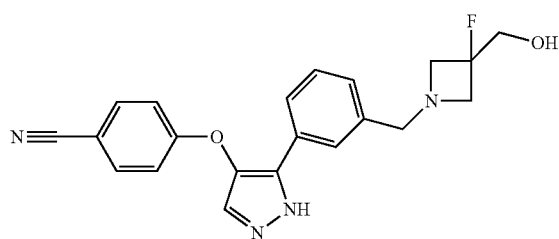 [SMILES: N#Cc1ccc(Oc2cn[nH]c2-c2cccc(CN3CC(F)(CO)C3)c2)cc1]

In analogy to the procedure described for the preparation of example 44 [B], (rac)-4-[3-[3-[[3-fluoro-3-(hydroxymethyl)azetidin-1-yl]methyl]phenyl]-1-tetrahydropyran-2-yl-pyrazol-4-yl]oxybenzonitrile has been reacted with HCl (4M dioxane) in MeOH to give the title compound as brown solid. MS: 379.2 (M+H⁺).

Example 75

4-[[3-[3-(Morpholin-4-ylmethyl)phenyl]-1H-pyrazol-4-yl]oxy]benzonitrile

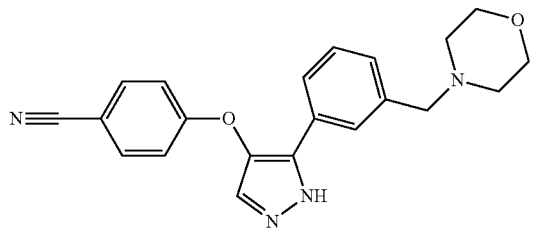 [SMILES: N#Cc1ccc(Oc2cn[nH]c2-c2cccc(CN3CCOCC3)c2)cc1]

In analogy to the procedures described for the preparation of example 74, (rac)-4-[3-(3-formylphenyl)-1-tetrahydropyran-2-yl-pyrazol-4-yl]oxybenzonitrile has been reacted with morpholine and subsequently HCl (4M dioxane) in MeOH to give the title compound as yellow oil. MS: 361.2 (M+H⁺).

Example 76

4-[[3-[2-(Pyridin-4-ylmethoxy)phenyl]-1H-pyrazol-4-yl]oxy]benzonitrile

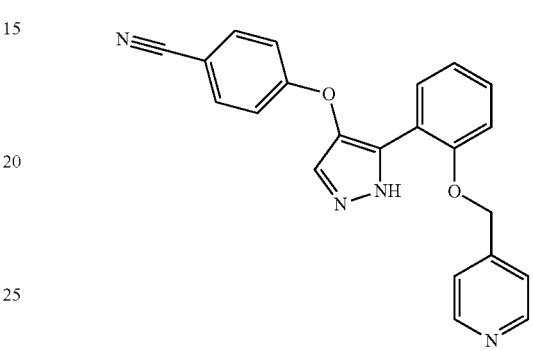

In analogy to the procedures described in examples 48 [A] and 48 [B], and in examples 50 [A] and 50 [B], the title compound has been prepared from 4-[[5-(2-phenylmethoxyphenyl)-1H-pyrazol-4-yl]oxy]benzonitrile (example 41) by the following reaction sequence: i) reaction with dihydropyran; ii) removal of the benzyl group by catalytic hydrogenation; iii) alkylation with 4-(bromomethyl)pyridine hydrobromide, potassium carbonate; iv) removal of the protecting group; it was obtained as colorless amorphous solid. MS: 369.1 (M+H⁺).

The following examples listed in Table 6 were prepared in analogy to the procedure described for the preparation of example 50 by reacting (rac)-4-[3-(2-hydroxyphenyl)-1-tetrahydropyran-2-yl-pyrazol-4-yl]oxybenzonitrile (example 76, step ii) reaction product) with a halo-methyl heterocyclic compounds and subsequently with acid.

TABLE 6

| Example | Name Aspect | Reactant | MS (M + H⁺) |
|---|---|---|---|
| 77 | 4-[[3-[2-(Pyridin-3-ylmethoxy)phenyl]-1H-pyrazol-4-yl]oxy]benzonitrile<br />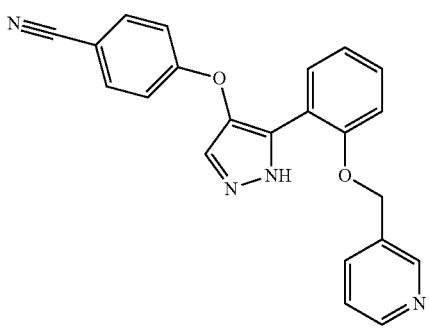<br />brown amorphous solid | 3-(bromomethyl)pyridine hydrobromide | 369.1 |

TABLE 6-continued

| Example | Name Aspect | Reactant | MS (M + H⁺) |
|---|---|---|---|
| 78 | 4-[[3-(2-Hydroxyphenyl)-1H-pyrazol-4-yl]oxy]benzonitrile<br />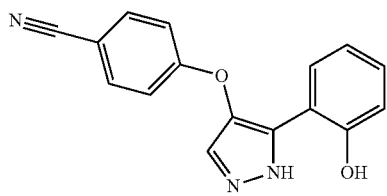<br />colorless amorphous solid | deprotection only (no alkylation) | 278.1 |
| 79 | 4-[[3-[2-(Pyridin-2-ylmethoxy)phenyl]-1H-pyrazol-4-yl]oxy]benzonitrile<br />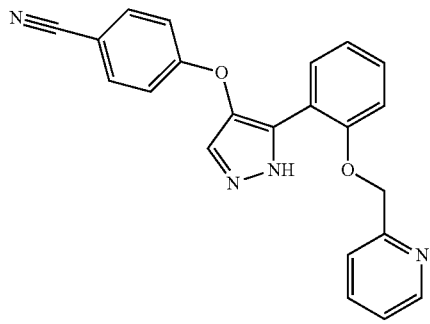<br />colorless amorphous solid | 2-(bromomethyl)pyridine hydrobromide | 369.1 |
| 80 | 4-[[3-[2-[(1-Methylpyrazol-4-yl)methoxy]phenyl]-1H-pyrazol-4-yl]oxy]benzonitrile<br />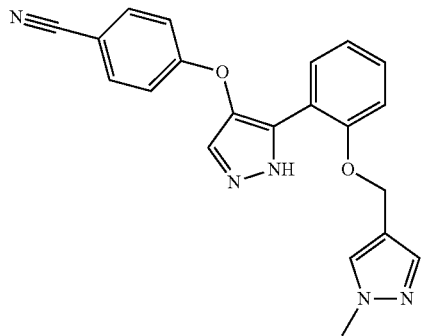<br />colorless amorphous solid | 4-(chloromethyl)-1-methyl-1H-pyrazole hydrochloride | 372.2 |

TABLE 6-continued

| Example | Name<br>Aspect | Reactant | MS<br>(M + H+) |
|---|---|---|---|
| 81 | 4-[[3-[2-[(3-Methyltriazol-4-yl)methoxy]phenyl]-1H-pyrazol-4-yl]oxy]benzonitrile<br>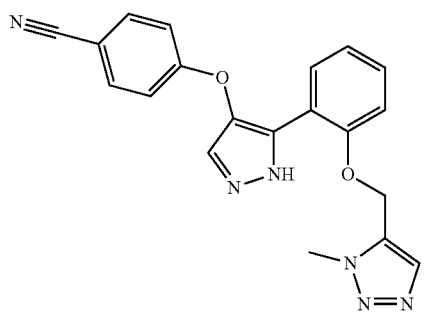<br>colorless solid | 5-(chloromethyl)-1-methyl-1H-1,2,3-triazole | 373.1 |

The following examples listed in Table 7 were prepared in analogy to the procedures described for the preparation of examples 69 [B] and [C] by reacting (rac)-4-[3-[2-(chloromethyl)phenyl]-1-tetrahydropyran-2-yl-pyrazol-4-yl]oxybenzonitrile (prepared from 2-[4-(4-cyanophenoxy)-1H-pyrazol-3-yl]benzoic acid (example 40) by i) reaction with dihydro-pyran; ii) reduction with borane tetrahydrofuran complex; iii) treatment with methanesulfonyl chloride, LiCl, 2,4,6-trimethylpyridine, DMF) with the heterocycles indicated and subsequent treatment with acid.

TABLE 7

| Example | Name<br>Aspect | Reactant | MS<br>(M + H+) |
|---|---|---|---|
| 82 | 4-[[3-[2-(Pyridin-3-yloxymethyl)phenyl]-1H-pyrazol-4-yl]oxy]benzonitrile<br>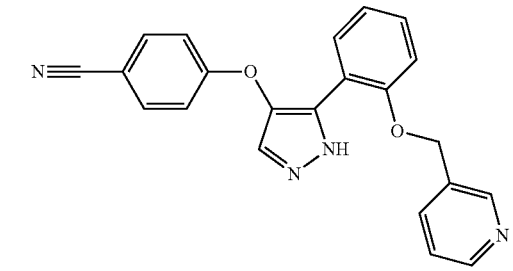<br>light brown amorphous solid | pyridin-3-ol | 369.1 |
| 83 | 4-[[3-[2-[(4-Oxopyridin-1-yl)methyl]phenyl]-1H-pyrazol-4-yl]oxy]benzonitrile<br>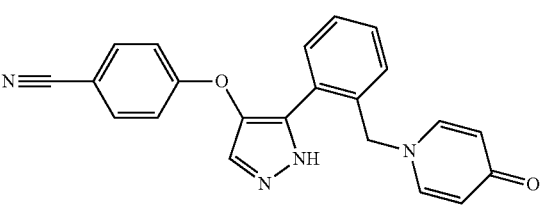<br>colorless amorphous solid | pyridin-4-ol | 369.1 |

Example 84

4-[[3-(2-Fluoro-3-hydroxyphenyl)-1H-pyrazol-4-yl]oxy]benzonitrile

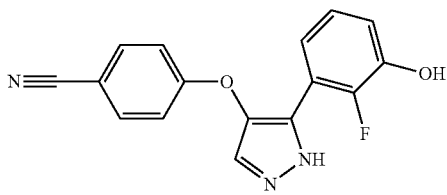 [SMILES: N#Cc1ccc(Oc2cn[nH]c2-c2cccc(O)c2F)cc1]

[A] (rac)-[4-[3-(2-Fluoro-3-hydroxy-phenyl)-1-tetrahydropyran-2-yl-pyrazol-4-yl]oxybenzonitrile

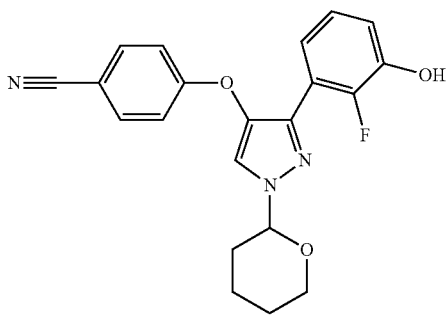 [SMILES: N#Cc1ccc(Oc2cn(C3CCCCO3)nc2-c2cccc(O)c2F)cc1]

In a microwave vial, (rac)-[4-(4-cyanophenoxy)-1-tetrahydropyran-2-yl-pyrazol-3-yl] trifluoromethanesulfonate (intermediate B-2) (0.296 g, 0.674 mmol) and 2-fluoro-3-hydroxyphenylboronic acid (0.105 g, 0.674 mmol) were mixed in DMF (3.0 mL). The mixture was purged with argon, then, bis(triphenylphosphine)palladium(II)dichloride (0.047 g, 0.067 mmol) followed by a 1M aqueous solution of $Na_2CO_3$ (2 mL, 2.02 mmol) were added. The reaction mixture was then immediately heated to 80° C. in the microwave for 5 min. The mixture was diluted with EtOAc, poured into a 1M aqueous HCl solution and the aqueous layer extracted with EtOAc (2×15 mL). The combined organics were washed with brine, dried over $Na_2SO_4$, filtered and evaporated. The residue was purified by prep-HPLC (Gemini NX 3u column, gradient 1% aq. formic acid/acetonitrile) to give the title compound (0.031 g, 10%) as colorless oil. MS: 380.2 (M+H$^+$).

[B] 4-[[3-(2-Fluoro-3-hydroxyphenyl)-1H-pyrazol-4-yl]oxy]benzonitrile

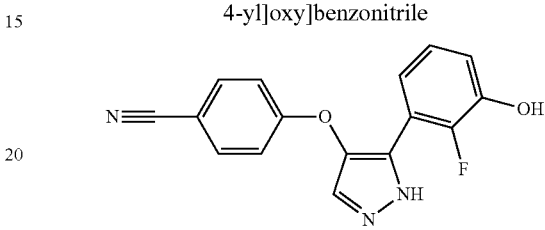

In analogy to the procedure described for the preparation of example 44 [B], (rac)-[4-[3-(2-fluoro-3-hydroxy-phenyl)-1-tetrahydropyran-2-yl-pyrazol-4-yl]oxybenzonitrile has been reacted with HCl (4M dioxane) in MeOH to give the title compound as colorless solid. MS: 296.1 (M+H$^+$).

The following examples listed in Table 8 were prepared in analogy to the procedure described for the preparation of example 50 by reacting (rac)-[4-[3-(2-fluoro-3-hydroxy-phenyl)-1-tetrahydropyran-2-yl-pyrazol-4-yl]oxybenzonitrile (example 84 [A]) with a halo-methyl heterocyclic compounds and subsequently with acid.

TABLE 8

| Example | Name Aspect | Reactant | MS (M + H$^+$) |
|---|---|---|---|
| 85 | 4-[[3-[2-Fluoro-3-(pyridin-4-ylmethoxy)phenyl]-1H-pyrazol-4-yl]oxy]benzonitrile<br>colorless oil | 4-(bromomethyl)pyridine hydrobromide | 387.1 |
| 86 | 4-[[3-[3-[(2-Chloropyridin-4-yl)methoxy]-2-fluorophenyl]-1H-pyrazol-4-yl]oxy]benzonitrile<br>yellow oil | 2-chloro-4-(chloromethyl)pyridine | 421.1 |

Example 87

4-[[5-(Piperazin-1-ylmethyl)-1H-pyrazol-4-yl]oxy]benzonitrile

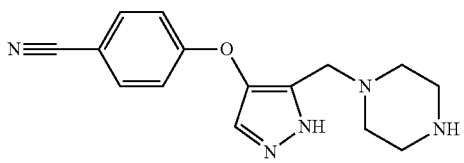 [SMILES: N#Cc1ccc(Oc2cn[nH]c2CN2CCNCC2)cc1]

In analogy to the procedure described for the preparation of example 44 [B], (rac)-tert-butyl 4-[[4-(4-cyanophenoxy)-1-tetrahydropyran-2-yl-pyrazol-3-yl]methyl]piperazine-1-carboxylate (intermediate B-3) has been reacted with HCl (4M dioxane) in MeOH to give the title compound as colorless oil. MS: 284.2 (M+H$^+$).

Example 88

4-[[5-[[4-(1-Methylpyrazole-4-carbonyl)piperazin-1-yl]methyl]-1H-pyrazol-4-yl]oxy]benzonitrile

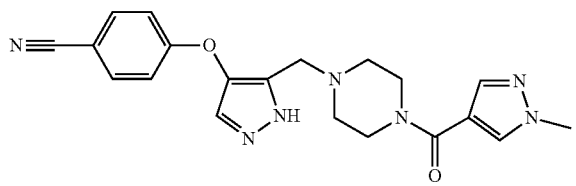 [SMILES: Cn1cc(C(=O)N2CCN(Cc3[nH]ncc3Oc3ccc(C#N)cc3)CC2)cn1]

In analogy to the procedure described for the preparation of example 64, 4-[[5-(piperazin-1-ylmethyl)-1H-pyrazol-4-yl]oxy]benzonitrile (example 87) has been reacted with 1-methyl-1H-pyrazole-4-carboxylic acid and TBTU to give the title compound as colorless amorphous solid. MS: 392.2 (M+H$^+$).

Example 89

(rac)-3-Fluoro-4-[[5-[1-(1-methylpyrazole-4-carbonyl)piperidin-3-yl]-1H-pyrazol-4-yl]oxy]benzonitrile

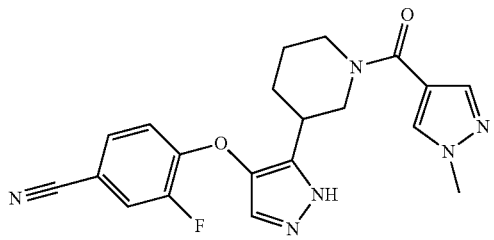 [SMILES: Cn1cc(C(=O)N2CCCC(c3[nH]ncc3Oc3ccc(C#N)cc3F)C2)cn1]

The title compound has been prepared by the following reaction sequence i) reaction of (rac)-[4-(4-cyano-2-fluorophenoxy)-1-tetrahydropyran-2-yl-pyrazol-3-yl] trifluoromethanesulfonate (prepared in analogy to the procedures described for the preparation of intermediate B-2, but replacing 4-hydroxybenzonitrile by 3-fluoro-4-hydroxy-benzonitrile) with tert-butyl 3-(4,4,5,5-tetramethyl-1,3,2-dioxaborolan-2-yl)-5,6-dihydropyridine-1(2H)-carboxylate in analogy to the procedure described for the preparation of example 61 [A]; ii) catalytic hydrogenation in analogy to the procedure described for the preparation of example 60 [B]; iii) removal of the protecting groups in analogy to the procedures described for the preparation of example 44 [B]; iv) coupling with 1-methyl-1H-pyrazole-4-carboxylic acid with the help of TBTU in analogy to the procedure described for the preparation of example 64; to give the title compound as colorless amorphous solid. MS: 395.2 (M+H$^+$).

Example 90

4-[[3-[3-Chloro-2-[(3-methyltriazol-4-yl)methoxy]phenyl]-1H-pyrazol-4-yl]oxy]benzonitrile

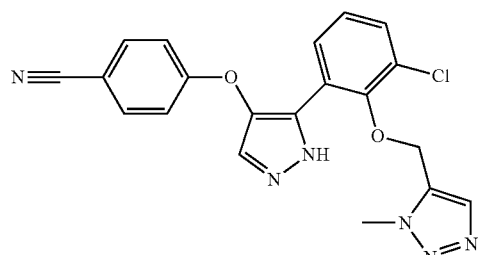

In analogy to the procedures described in example 61 [A], example 50 [A] and example 44 [B], (rac)-[4-(4-cyanophenoxy)-1-tetrahydropyran-2-yl-pyrazol-3-yl] trifluoromethanesulfonate (intermediate B-2) has been reacted with 3-chloro-2-hydroxyphenylboronic acid, followed by reaction with 5-(chloromethyl)-1-methyl-1H-1,2,3-triazole and subsequently with HCl (4M dioxane) in MeOH to give the title compound as colorless amorphous solid. MS: 407.1 (M+H$^+$).

Example 91

(rac)-3-Fluoro-4-[[3-[1-(pyridine-3-carbonyl)piperidin-3-yl]-1H-pyrazol-4-yl]oxy]benzonitrile

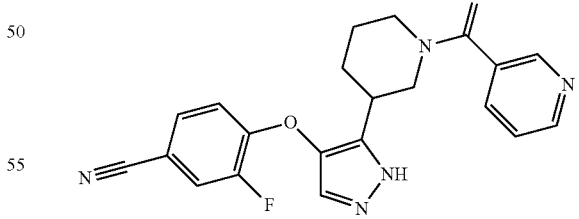

The title compound has been prepared by the following reaction sequence i) reaction of (rac)-[4-(4-cyano-2-fluorophenoxy)-1-tetrahydropyran-2-yl-pyrazol-3-yl] trifluoromethanesulfonate (prepared in analogy to the procedures described for the preparation of intermediate B-2, but replacing 4-hydroxybenzonitrile by 3-fluoro-4-hydroxy-benzonitrile) with tert-butyl 3-(4,4,5,5-tetramethyl-1,3,2-dioxaborolan-2-yl)-5,6-dihydropyridine-1(2H)-carboxylate in analogy to the procedure described for the preparation of example 61

[A]; ii) catalytic hydrogenation in analogy to the procedure described for the preparation of example 60 [B]; iii) removal of the protecting groups in analogy to the procedures described for the preparation of example 44 [B]; iv) coupling with nicotinic acid with the help of TBTU in analogy to the procedure described for the preparation of example 64; to give the title compound as brown oil. MS: 392.2 (M+H$^+$).

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

We claim:

1. A compound of formula (I) wherein

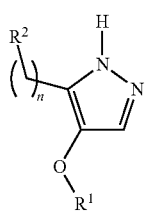

(I)

R$^1$ is substituted phenyl or substituted pyridinyl, wherein substituted phenyl and substituted pyridinyl are substituted with one to three substituents independently selected from cyano, halogen, haloalkyl, alkoxy and alkyl;

R$^2$ is a ring system selected from group A, B, C, D, E, F, G and H:

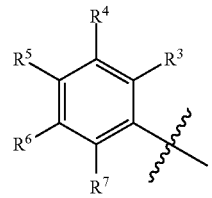

A

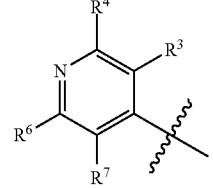

B

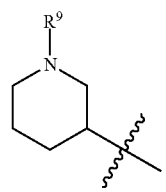

C

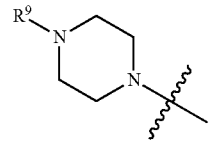

D

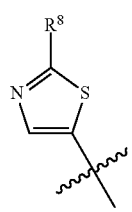

E

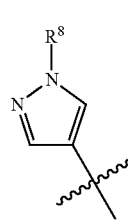

F

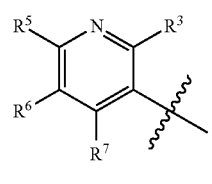

G

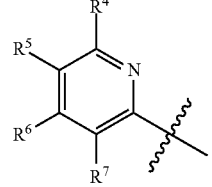

H

R$^3$ and R$^7$ are independently selected from H, alkyl, alkoxy, halogen, haloalkoxy, carboxy, alkoxycarbonyl, optionally substituted phenylalkoxy, optionally substituted heteroarylalkoxy, optionally substituted heteroarylalkyl, optionally substituted heteroaryloxyalkyl or optionally substituted heterocycloalkoxy, wherein the optionally substituted moieties are substituted with one to three substituents independently selected from alkyl or halogen;

$R^4$ is (i) H, (ii) hydroxy, (iii) hydroxyalkyl, (iv) alkoxy, (v) alkoxycarbonyl, (vi) halogen, (vii) phenylalkoxy, (viii) heterocycloalkylcarbonyl optionally substituted by one to three substituents independently selected from alkylcarbonyl, alkylsulfonyl or hydroxyalkyl, (ix) heteroarylalkoxy optionally substituted by one to three substituents independently selected from alkyl and halogen, (x) heteroaryloxyalkyl optionally substituted by one to three halogen(s), (xi) heteroarylalkyl optionally substituted by one to three substituents hydroxy, (xii) heterocycloalkoxy optionally substituted by one to three alkylcarbonyl, or (xiii) heterocycloalkylalkyl optionally substituted by one to three substituents independently selected from halogen and hydroxyalkyl;

$R^6$ is H or halogen;

$R^5$ is H, halogen, alkoxy, alkylsulfonyl, alkylsulfanyl or haloalkyl;

$R^8$ is alkyl or phenylalkyl;

$R^9$ is H, alkylcarbonyl or heteroarylcarbonyl optionally substituted by one to three alkyl groups;

n is zero, 1 or 2; or a pharmaceutically acceptable salt thereof.

2. The compound according to claim 1, wherein $R^1$ is phenyl substituted with substituted with one to three substituents independently selected from cyano and halogen.

3. The compound according to claim 1 wherein $R^2$ is a ring system selected from group A, B, C, D, E and F.

4. The compound according to claim 3, wherein $R^2$ is a ring system selected from group A, B and C.

5. The compound according claim 4 wherein one of $R^2$ is the ring system group A.

6. The compound according to claim 1 wherein n is zero.

7. The compound according claim 1 wherein $R^7$ is H.

8. The compound according to claim 1 wherein $R^3$ is H, alkoxy, halogen, haloalkoxy or heteroarylalkoxy optionally independently substituted with one to three alkyl substituents.

9. The compound according to claim 1, wherein $R^4$ is H, hydroxy, heteroarylalkoxy or heterocycloalkylalkyl.

10. The compound according to claim 1, wherein $R^4$ is H.

11. The compound according to claim 1 wherein $R^5$ is H.

12. The compound according to claim 1 wherein $R^6$ is H.

13. The compound according to claim 1 wherein $R^7$ is H.

14. The compound of claim 1 wherein $R^3$ is H, alkoxy, halogen, haloalkoxy or heteroarylalkoxy optionally independently substituted with one to three alkyl substituents, and $R^4$, $R^5$, $R^6$ and $R^7$ are hydrogen.

15. The compound according to claim 1 wherein $R^2$ is C or D and $R^9$ is heteroarylcarbonyl substituted by one alkyl.

16. The compound according to claim 1 which compound is selected from the group consisting of:

4-(4-Chlorophenoxy)-5-(2,3-difluorophenyl)-1H-pyrazole;
3-(4-Chlorophenyl)-4-(4-methoxyphenoxy)-1H-pyrazole;
4-(4-Chlorophenoxy)-3-(4-chlorophenyl)-1H-pyrazole;
4-(4-Chlorophenoxy)-3-(2-methoxyphenyl)-1H-pyrazole;
4-(4-Chlorophenoxy)-3-(2,4-dimethoxyphenyl)-1H-pyrazole;
4-(4-Chlorophenoxy)-5-(2-chlorophenyl)-1H-pyrazole;
4-(4-Chlorophenoxy)-5-[2-(trifluoromethoxy)phenyl]-1H-pyrazole;
4-(4-Chlorophenoxy)-5-[2-(difluoromethoxy)phenyl]-1H-pyrazole;
4-(4-Chlorophenoxy)-5-(2-fluorophenyl)-1H-pyrazole;
3-(5-Chloro-2-methoxyphenyl)-4-(4-chlorophenoxy)-1H-pyrazole;
5-(4-Chloro-2-fluorophenyl)-4-(4-chlorophenoxy)-1H-pyrazole;
4-(4-Chlorophenoxy)-5-(4-methylsulfonylphenyl)-1H-pyrazole;
4-(4-Chlorophenoxy)-5-[2-fluoro-4-(trifluoromethyl)phenyl]-1H-pyrazole;
4-(4-Chlorophenoxy)-5-[4-(trifluoromethyl)phenyl]-1H-pyrazole;
4-(4-Chlorophenoxy)-5-(2,4-difluorophenyl)-1H-pyrazole;
5-(4-Methylsulfonylphenyl)-4-[4-(trifluoromethyl)phenoxy]-1H-pyrazole;
5-(2-Chloro-4-methyl sulfanylphenyl)-4-(4-chlorophenoxy)-1H-pyrazole;
4-[[5-(4-Methylsulfonylphenyl)-1H-pyrazol-4-yl]oxy]benzonitrile;
2-Chloro-5-[[5-(2-chlorophenyl)-1H-pyrazol-4-yl]oxy]pyridine;
5-[[5-(2-Chlorophenyl)-1H-pyrazol-4-yl]oxy]-2-methylpyridine;
2-[[5-(2,4-Dichlorophenyl)-1H-pyrazol-4-yl]oxy]-6-fluoropyridine;
2-[[3-(2,4-Dichlorophenyl)-1H-pyrazol-4-yl]oxy]-6-methylpyridine;
5-(2-Chlorophenyl)-4-[4-(trifluoromethyl)phenoxy]-1H-pyrazole;
4-(4-Chloro-2-fluorophenoxy)-5-(2-chlorophenyl)-1H-pyrazole;
4-[[5-(2-Chlorophenyl)-1H-pyrazol-4-yl]oxy]benzonitrile;
4-[[5-(2-Chloro-4-methylsulfanylphenyl)-1H-pyrazol-4-yl]oxy]benzonitrile;
5-(4-Chloro-2-fluorophenyl)-4-[4-(trifluoromethyl)phenoxy]-1H-pyrazole;
4-[[5-(2-Chlorophenyl)-1H-pyrazol-4-yl]oxy]-3-fluorobenzonitrile;
4-[[5-(2,3-Difluorophenyl)-1H-pyrazol-4-yl]oxy]benzonitrile;
4-[[5-(3-Chloro-2-fluorophenyl)-1H-pyrazol-4-yl]oxy]benzonitrile;
5-(3-Chloro-2-fluorophenyl)-4-(4-chlorophenoxy)-1H-pyrazole;
4-[[5-(3-Chlorophenyl)-1H-pyrazol-4-yl]oxy]benzonitrile;
Methyl 3-[4-(4-cyanophenoxy)-1H-pyrazol-3-yl]benzoate;
5-(2-Chloro-3-fluorophenyl)-4-(4-chlorophenoxy)-1H-pyrazole;
4-[[5-(2-Chloro-3-fluorophenyl)-1H-pyrazol-4-yl]oxy]benzonitrile;
4-[[5-(3-Phenylmethoxyphenyl)-1H-pyrazol-4-yl]oxy]benzonitrile;
4-[[5-(2-Chloropyridin-4-yl)-1H-pyrazol-4-yl]oxy]benzonitrile;
Methyl 3-[4-(4-cyano-2-fluorophenoxy)-1H-pyrazol-3-yl]benzoate;
Ethyl 2-[4-(4-cyanophenoxy)-1H-pyrazol-3-yl]benzoate;
2-[4-(4-Cyanophenoxy)-1H-pyrazol-3-yl]benzoic acid;
4-[[5-(2-Phenylmethoxyphenyl)-1H-pyrazol-4-yl]oxy]benzonitrile;

5-(2-Chloro-4-methylsulfonylphenyl)-4-(4-chlorophenoxy)-1H-pyrazole;
4-[[5-(2-Chloro-4-methylsulfonylphenyl)-1H-pyrazol-4-yl]oxy]benzonitrile;
4-[[3-[3-(4-Acetylpiperazine-1-carbonyl)phenyl]-1H-pyrazol-4-yl]oxy]benzonitrile;
4-[[3-[3-(Morpholine-4-carbonyl)phenyl]-1H-pyrazol-4-yl]oxy]benzonitrile;
4-[[3-[3-(4-Methylsulfonylpiperazine-1-carbonyl)phenyl]-1H-pyrazol-4-yl]oxy]benzonitrile;
4-[[3-[3-[3-(Hydroxymethyl)azetidine-1-carbonyl]phenyl]-1H-pyrazol-4-yl]oxy]benzonitrile;
4-[[3-(3-Hydroxyphenyl)-1H-pyrazol-4-yl]oxy]benzonitrile;
4-[[3-[3-(Hydroxymethyl)phenyl]-1H-pyrazol-4-yl]oxy]benzonitrile;
4-[[3-[3-(Pyridin-2-ylmethoxy)phenyl]-1H-pyrazol-4-yl]oxy]benzonitrile;
4-[[3-[3-(Pyridin-3-ylmethoxy)phenyl]-1H-pyrazol-4-yl]oxy]benzonitrile;
4-[[3-[3-[(3-Methyl-1,2-oxazol-5-yl)methoxy]phenyl]-1H-pyrazol-4-yl]oxy]benzonitrile;
4-[[3-[3-[(3-Methyltriazol-4-yl)methoxy]phenyl]-1H-pyrazol-4-yl]oxy]benzonitrile;
4-[[3-[3-(Pyridin-4-ylmethoxy)phenyl]-1H-pyrazol-4-yl]oxy]benzonitrile;
4-[[3-[3-[(2-Chloropyridin-4-yl)methoxy]phenyl]-1H-pyrazol-4-yl]oxy]benzonitrile;
4-[[3-[3-[(1-Methylpyrazol-4-yl)methoxy]phenyl]-1H-pyrazol-4-yl]oxy]benzonitrile;
(rac)-4-[[3-[3-(3-Pyrrolidin-3-yloxyphenyl)-1H-pyrazol-4-yl]oxy]benzonitrile;
(rac)-4-[[3-[3-(1-Acetylpyrrolidin-3-yl)oxyphenyl]-1H-pyrazol-4-yl]oxy]benzonitrile;
4-[[3-(3-Butoxyphenyl)-1H-pyrazol-4-yl]oxy]benzonitrile;
4-[[3-[2-(2-Methoxyphenyl)ethyl]-1H-pyrazol-4-yl]oxy]benzonitrile;
(rac)-4-[[5-(3-Piperidyl)-1H-pyrazol-4-yl]oxy]benzonitrile;
(rac)-4-[[3-(1-Acetylpiperidin-3-yl)-1H-pyrazol-4-yl]oxy]benzonitrile;
(rac)-4-[[3-[1-(1-Methylpyrazole-4-carbonyl)piperidin-3-yl]-1H-pyrazol-4-yl]oxy]benzonitrile;
(rac)-4-[[3-[1-(Pyridine-3-carbonyl)piperidin-3-yl]-1H-pyrazol-4-yl]oxy]benzonitrile;
(rac)-4-[[3-[1-(Pyridine-2-carbonyl)piperidin-3-yl]-1H-pyrazol-4-yl]oxy]benzonitrile;
4-[[3-(2-Methyl-1,3-thiazol-5-yl)-1H-pyrazol-4-yl]oxy]benzonitrile;
4-[[3-(1-Methylpyrazol-4-yl)-1H-pyrazol-4-yl]oxy]benzonitrile;
4-[[3-(1-Benzylpyrazol-4-yl)-1H-pyrazol-4-yl]oxy]benzonitrile;
4-[[3-[3-[(6-Fluoropyridin-2-yl)oxymethyl]phenyl]-1H-pyrazol-4-yl]oxy]benzonitrile;
4-[[3-[3-(Pyridin-3-yloxymethyl)phenyl]-1H-pyrazol-4-yl]oxy]benzonitrile;
1-[[3-[4-(4-Cyanophenoxy)-1H-pyrazol-3-yl]phenyl]methyl]pyridin-1-ium-3-olate;
4-[[3-[3-[(4-Oxopyridin-1-yl)methyl]phenyl]-1H-pyrazol-4-yl]oxy]benzonitrile;
4-[[3-[3-[(6-Chloropyridin-2-yl)oxymethyl]phenyl]-1H-pyrazol-4-yl]oxy]benzonitrile;
4-[[3-[3-[[3-Fluoro-3-(hydroxymethyl)azetidin-1-yl]methyl]phenyl]-1H-pyrazol-4-yl]oxy]benzonitrile;
4-[[3-[3-(Morpholin-4-ylmethyl)phenyl]-1H-pyrazol-4-yl]oxy]benzonitrile;
4-[[3-[2-(Pyridin-4-ylmethoxy)phenyl]-1H-pyrazol-4-yl]oxy]benzonitrile;
4-[[3-[2-(Pyridin-3-ylmethoxy)phenyl]-1H-pyrazol-4-yl]oxy]benzonitrile;
4-[[3-(2-Hydroxyphenyl)-1H-pyrazol-4-yl]oxy]benzonitrile;
4-[[3-[2-(Pyridin-2-ylmethoxy)phenyl]-1H-pyrazol-4-yl]oxy]benzonitrile;
4-[[3-[2-[(1-Methylpyrazol-4-yl)methoxy]phenyl]-1H-pyrazol-4-yl]oxy]benzonitrile;
4-[[3-[2-[(3-Methyltriazol-4-yl)methoxy]phenyl]-1H-pyrazol-4-yl]oxy]benzonitrile;
4-[[3-[2-(Pyridin-3-yloxymethyl)phenyl]-1H-pyrazol-4-yl]oxy]benzonitrile;
4-[[3-[2-[(4-Oxopyridin-1-yl)methyl]phenyl]-1H-pyrazol-4-yl]oxy]benzonitrile;
4-[[3-(2-Fluoro-3-hydroxyphenyl)-1H-pyrazol-4-yl]oxy]benzonitrile;
4-[[3-[2-Fluoro-3-(pyridin-4-ylmethoxy)phenyl]-1H-pyrazol-4-yl]oxy]benzonitrile;
4-[[3-[3-[(2-Chloropyridin-4-yl)methoxy]-2-fluorophenyl]-1H-pyrazol-4-yl]oxy]benzonitrile;
4-[[5-(Piperazin-1-ylmethyl)-1H-pyrazol-4-yl]oxy]benzonitrile;
4-[[5-[[4-(1-Methylpyrazole-4-carbonyl)piperazin-1-yl]methyl]-1H-pyrazol-4-yl]oxy]benzonitrile;
(rac)-3-Fluoro-4-[[5-[1-(1-methylpyrazole-4-carbonyl)piperidin-3-yl]-1H-pyrazol-4-yl]oxy]benzonitrile;
4-[[3-[3-Chloro-2-[(3-methyltriazol-4-yl)methoxy]phenyl]-1H-pyrazol-4-yl]oxy]benzonitrile; and,
(rac)-3-Fluoro-4-(3-(1-nicotinoylpiperidin-3-yl)-1H-pyrazol-4-yloxy)benzonitrile; or,
a pharmaceutically acceptable salt thereof.

17. A compound according claim 16 wherein said compound is selected from the group consisting of:
4-(4-Chlorophenoxy)-3-(2-methoxyphenyl)-1H-pyrazole;
4-(4-Chlorophenoxy)-5-[2-(difluoromethoxy)phenyl]-1H-pyrazole;
4-[[5-(2-Chlorophenyl)-1H-pyrazol-4-yl]oxy]benzonitrile;
4-[[5-(2-Chlorophenyl)-1H-pyrazol-4-yl]oxy]-3-fluorobenzonitrile;
4-[[3-[2-(2-Methoxyphenyl)ethyl]-1H-pyrazol-4-yl]oxy]benzonitrile;
(rac)-4-[[3-[1-(1-Methylpyrazole-4-carbonyl)piperidin-3-yl]-1H-pyrazol-4-yl]oxy]benzonitrile;
4-[[3-[3-(Morpholin-4-ylmethyl)phenyl]-1H-pyrazol-4-yl]oxy]benzonitrile;
4-[[3-[2-[(3-Methyltriazol-4-yl)methoxy]phenyl]-1H-pyrazol-4-yl]oxy]benzonitrile;
4-[[3-(2-Fluoro-3-hydroxyphenyl)-1H-pyrazol-4-yl]oxy]benzonitrile;
4-[[3-[2-Fluoro-3-(pyridin-4-ylmethoxy)phenyl]-1H-pyrazol-4-yl]oxy]benzonitrile;
4-[[5-[[4-(1-Methylpyrazole-4-carbonyl)piperazin-1-yl]methyl]-1H-pyrazol-4-yl]oxy]benzonitrile; and,
(rac)-3-Fluoro-4-[[5-[1-(1-methylpyrazole-4-carbonyl)piperidin-3-yl]-1H-pyrazol-4-yl]oxy]benzonitrile; or,
a pharmaceutically acceptable salt thereof.

18. A process to prepare a compound according to claim 1 comprising the reaction of a compound of formula (II) or (III with hydrazine hydrate;

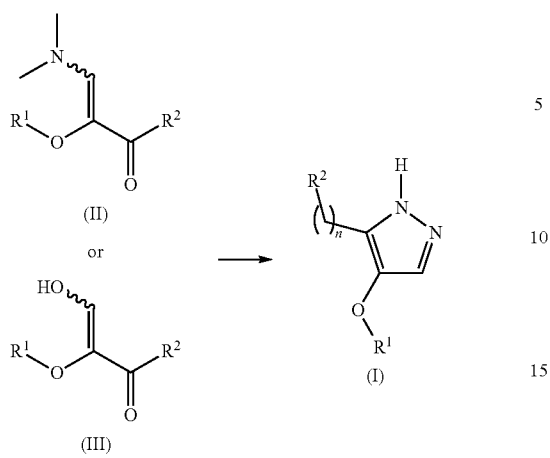

wherein R[1] and R[2] are as defined in claim 1.

19. A pharmaceutical composition comprising a compound according claim 1 and at least one pharmaceutically acceptable carrier, diluent or excipient.

20. A method for the treatment of chronic kidney disease, congestive heart failure, hypertension, primary aldosteronism and Cushing syndrome, which method comprises administering to a patient in need thereof a therapeutically effective amount of a compound according to claim 1.

* * * * *